(12) United States Patent
Skarsgard

(10) Patent No.: US 11,963,874 B2
(45) Date of Patent: Apr. 23, 2024

(54) APPARATUS FOR USE IN REPAIRING MITRAL VALVES AND METHOD OF USE THEREOF

(71) Applicant: Vesalius Cardiovascular Inc., Vancouver (CA)

(72) Inventor: Peter Skarsgard, Vancouver (CA)

(73) Assignee: Vesalius Cardiovascular Inc., Vancouver (CA)

( * ) Notice: Subject to any disclaimer, the term of this patent is extended or adjusted under 35 U.S.C. 154(b) by 0 days.

(21) Appl. No.: 18/299,644

(22) Filed: Apr. 12, 2023

(65) Prior Publication Data

US 2023/0240848 A1     Aug. 3, 2023

Related U.S. Application Data

(63) Continuation of application No. 17/426,046, filed as application No. PCT/CA2020/050095 on Jan. 27, 2020.

(Continued)

(51) Int. Cl.
*A61F 2/24* (2006.01)
*A61B 17/04* (2006.01)

(52) U.S. Cl.
CPC ........ *A61F 2/2445* (2013.01); *A61B 17/0401* (2013.01); *A61F 2/2466* (2013.01);
(Continued)

(58) Field of Classification Search
CPC ............ A61F 2/2445; A61F 2250/0007; A61F 2/2454; A61F 2250/0037; A61F 2/2487; A61F 2/2457
See application file for complete search history.

(56) References Cited

U.S. PATENT DOCUMENTS

2004/0044350 A1   3/2004 Martin et al.
2004/0049262 A1   3/2004 Obermiller et al.
(Continued)

FOREIGN PATENT DOCUMENTS

EP    3028668 A1    6/2016
WO    2011072084 A2    6/2011
(Continued)

*Primary Examiner* — Matthew J Lawson
*Assistant Examiner* — Cassidy N Stuhlsatz
(74) *Attorney, Agent, or Firm* — Oyen Wiggs Green & Mutala LLP

(57) ABSTRACT

Apparatus for repairing a heart valve and methods for implanting anchors and repairing a heart valve are provided. The apparatus comprises a body, a member attached to the body at a first end and having a plurality of positioning cords spaced laterally across the member and extending away from a second end of the member opposed to the first end, a tube suspended from the plurality of positioning cords, and an adjustment cord extending through the tube. The method comprises implanting at least one annular anchor in a mitral annulus of the heart valve, implanting a papillary anchor through each papillary muscle of the heart, delivering and positioning an apparatus for repairing a heart valve inside the heart valve using the at least one annular anchor and the papillary anchors, and adjusting the apparatus to adjust the extent of atrial displacement of the heart's mitral leaflets during ventricular contraction.

17 Claims, 74 Drawing Sheets

Related U.S. Application Data

(60) Provisional application No. 62/797,778, filed on Jan. 28, 2019.

(52) U.S. Cl.
CPC ............. *A61F 2210/0014* (2013.01); *A61F 2220/0016* (2013.01); *A61F 2230/0019* (2013.01); *A61F 2230/0021* (2013.01)

(56) References Cited

U.S. PATENT DOCUMENTS

| | | |
|---|---|---|
| 2004/0143323 A1 | 7/2004 | Chawla |
| 2005/0075727 A1* | 4/2005 | Wheatley ............. A61F 2/2457 623/902 |
| 2006/0178700 A1 | 8/2006 | Quinn |
| 2007/0112425 A1 | 5/2007 | Schaller et al. |
| 2007/0270943 A1 | 11/2007 | Solem et al. |
| 2008/0086164 A1* | 4/2008 | Rowe ................. A61F 2/2466 606/191 |
| 2008/0125861 A1* | 5/2008 | Webler ................. A61B 17/064 623/2.36 |
| 2008/0195126 A1 | 8/2008 | Solem |
| 2009/0240326 A1 | 9/2009 | Wilson et al. |
| 2010/0023117 A1* | 1/2010 | Yoganathan .......... A61F 2/2457 623/2.37 |
| 2010/0082094 A1 | 4/2010 | Quadri et al. |
| 2011/0071626 A1* | 3/2011 | Wright ................. A61F 2/2445 623/2.37 |
| 2012/0290077 A1 | 11/2012 | Aklog et al. |
| 2013/0172978 A1 | 7/2013 | Vidlund et al. |
| 2014/0142689 A1 | 5/2014 | De Canniere et al. |
| 2014/0358224 A1 | 12/2014 | Tegels et al. |
| 2017/0065418 A1* | 3/2017 | Skarsgard ............ A61F 2/2487 |
| 2017/0216023 A1* | 8/2017 | Lane .................... A61F 2/2418 |
| 2017/0258589 A1 | 9/2017 | Pham et al. |
| 2018/0049871 A1* | 2/2018 | Zeng ................... A61F 2/2418 |
| 2018/0071098 A1 | 3/2018 | Alon |
| 2018/0289474 A1* | 10/2018 | Rajagopal ............ A61F 2/2418 |
| 2018/0289480 A1 | 10/2018 | D'ambra et al. |
| 2018/0289483 A1 | 10/2018 | Speziali et al. |

FOREIGN PATENT DOCUMENTS

| | | |
|---|---|---|
| WO | 2013028387 A2 | 2/2013 |
| WO | 2015152980 A1 | 10/2015 |
| WO | 2016209970 A1 | 12/2016 |
| WO | 2018057716 A1 | 3/2018 |

* cited by examiner

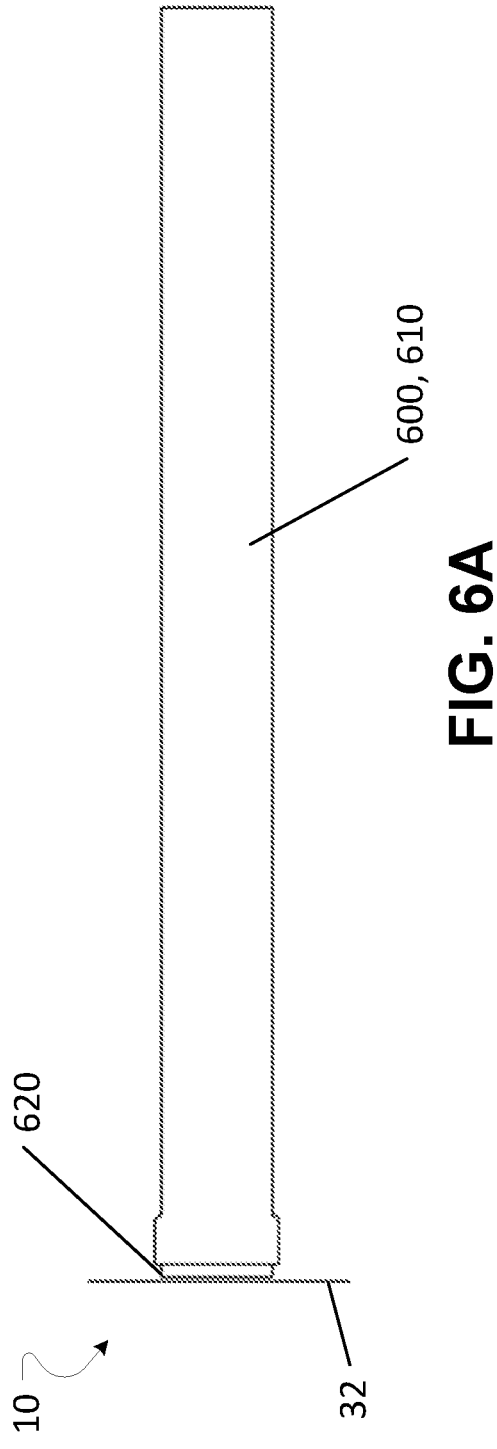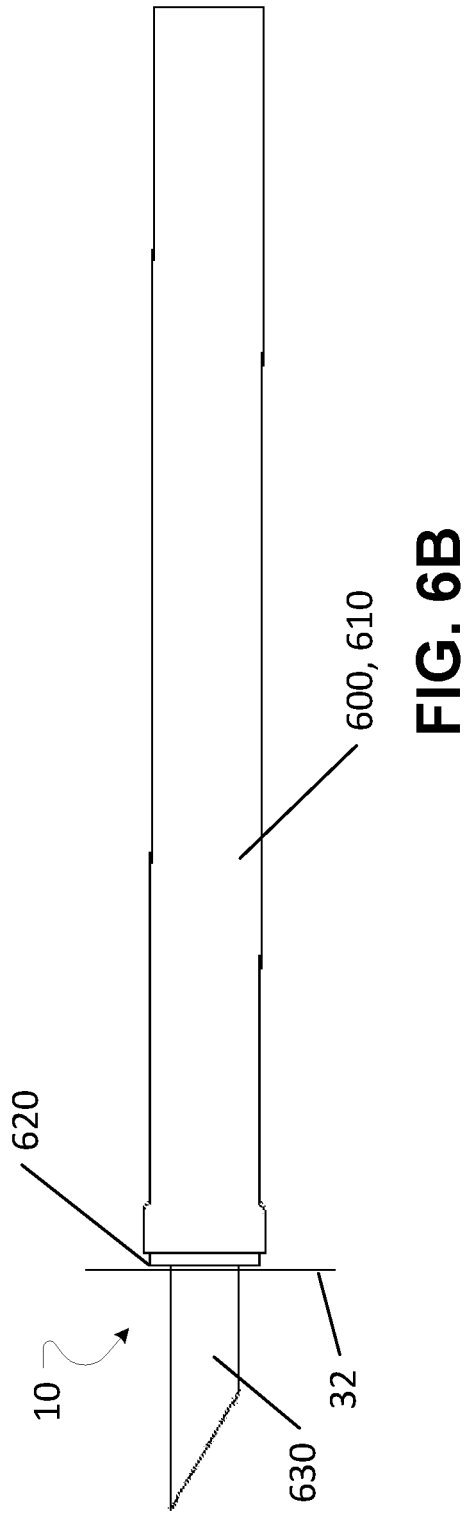

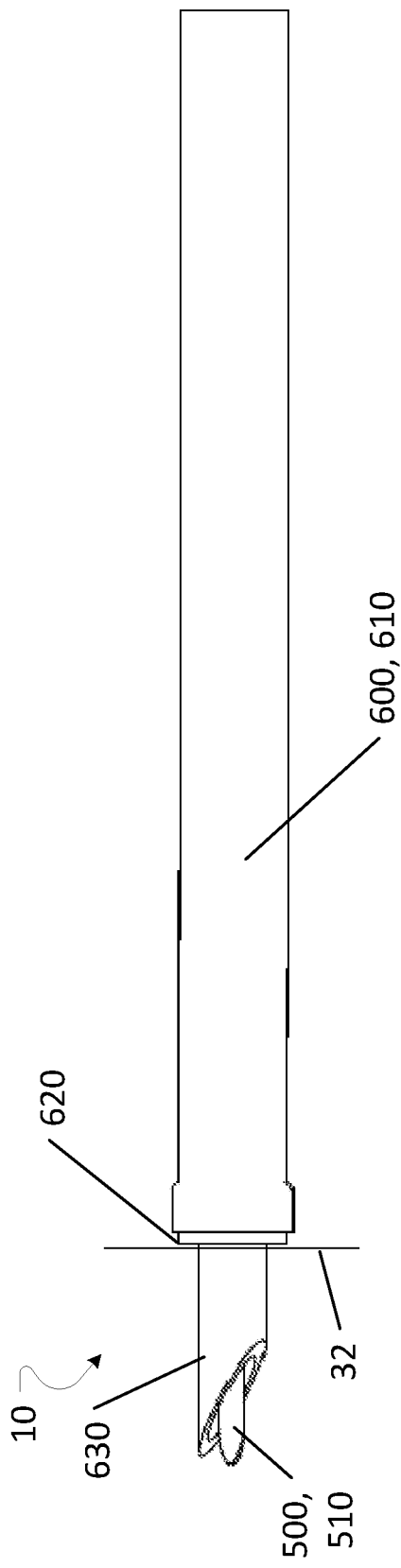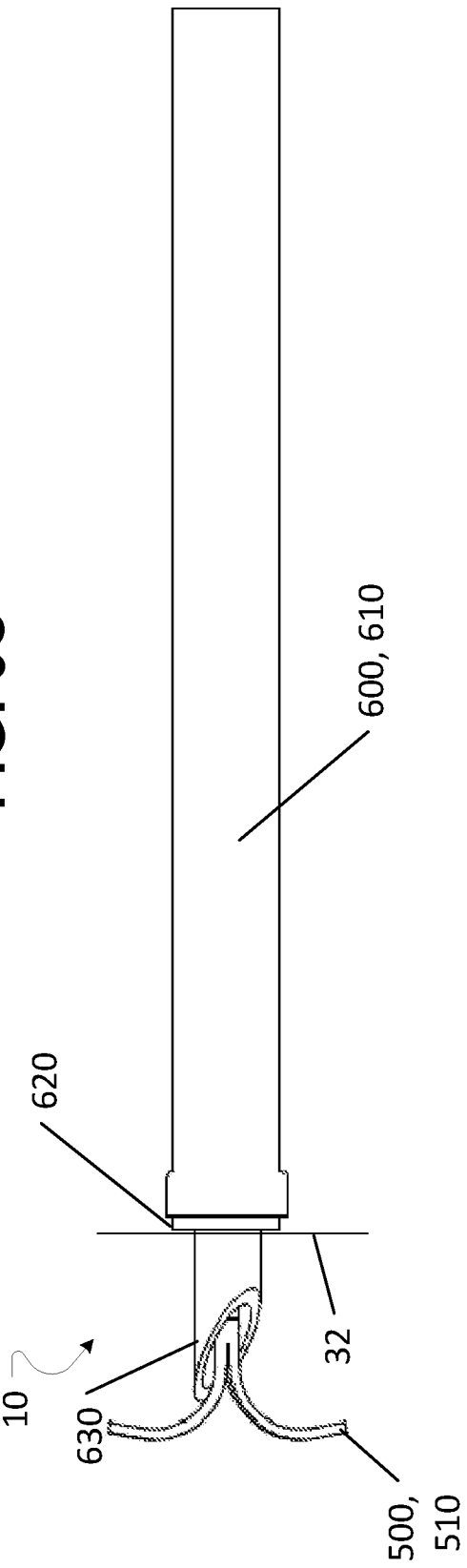

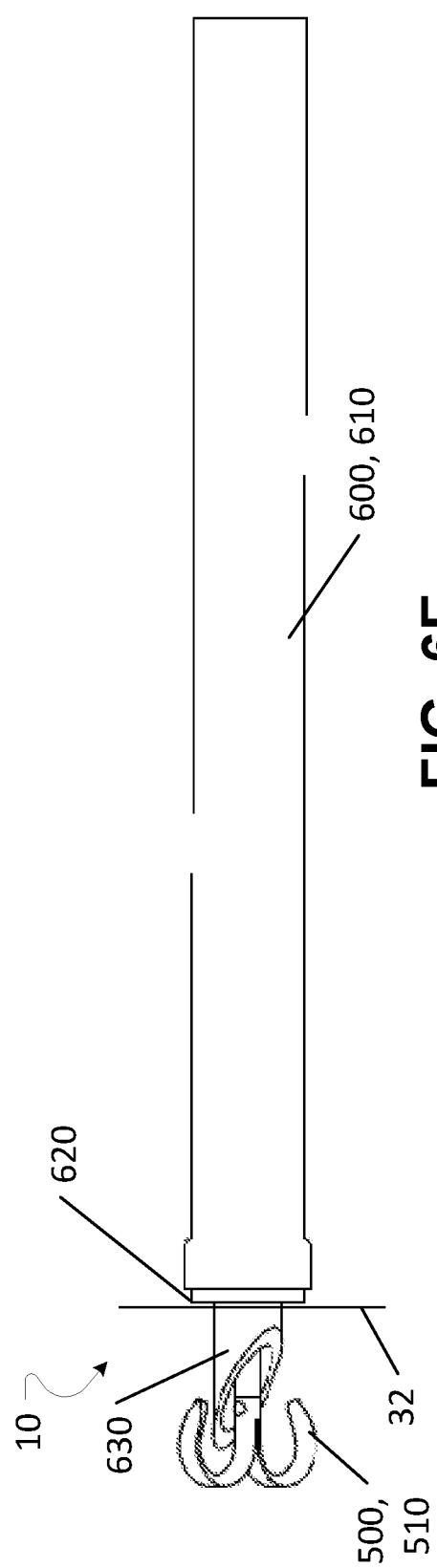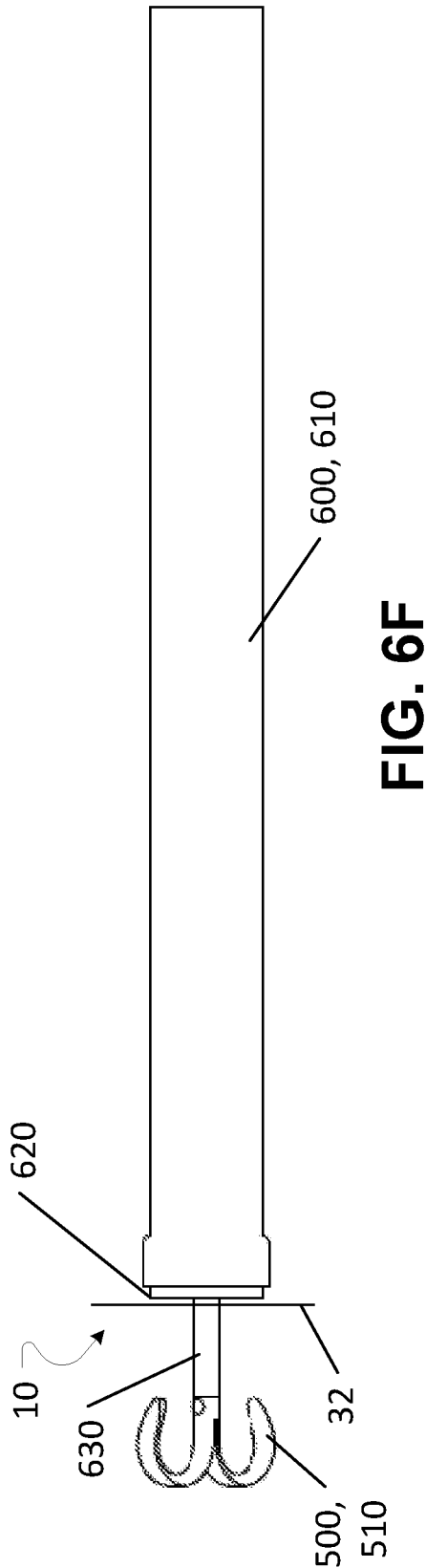

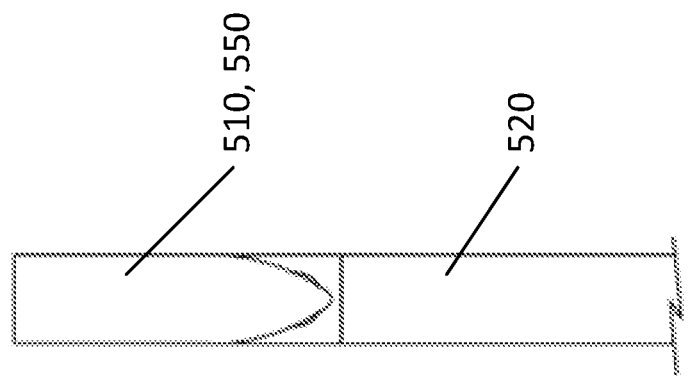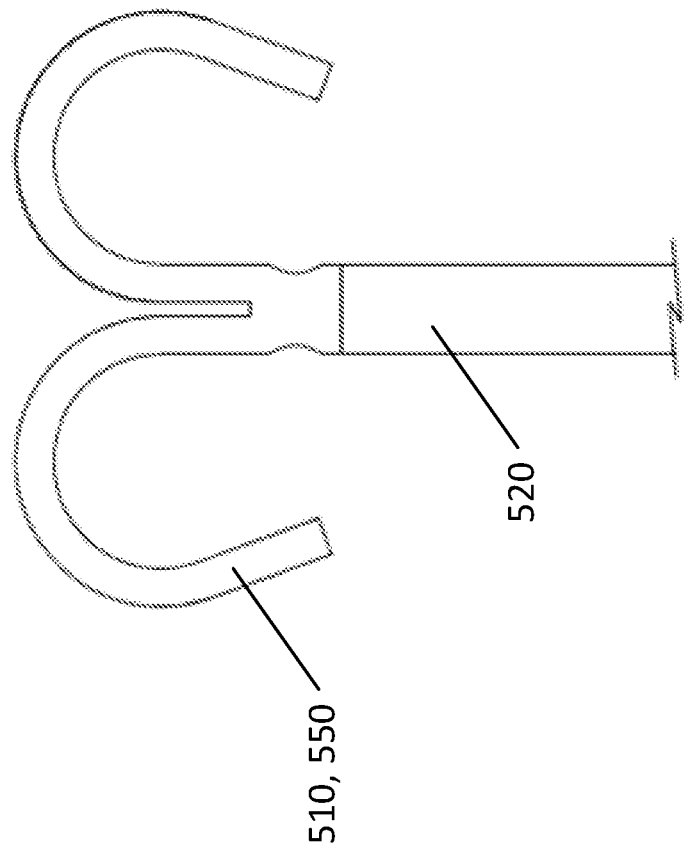

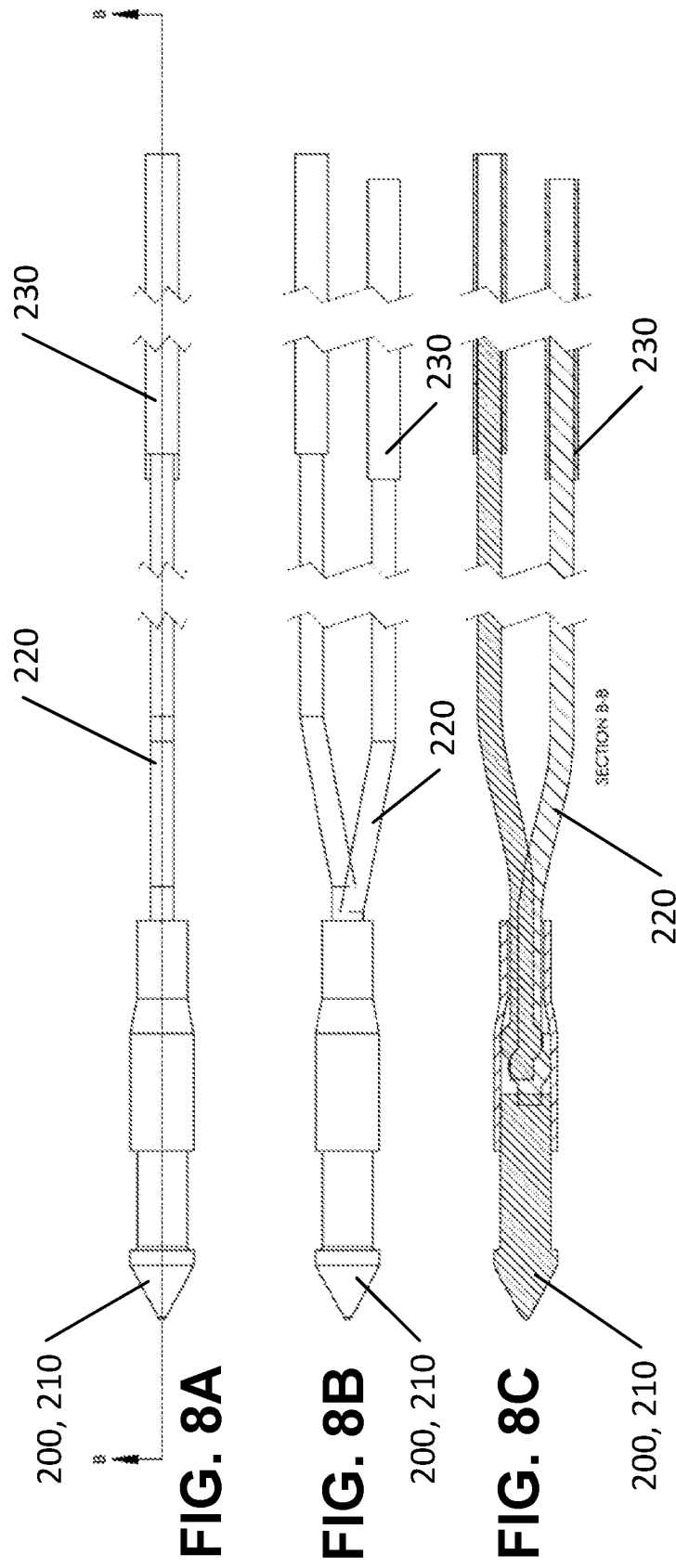

200, 210A 200, 210B 200, 210C 200, 210D

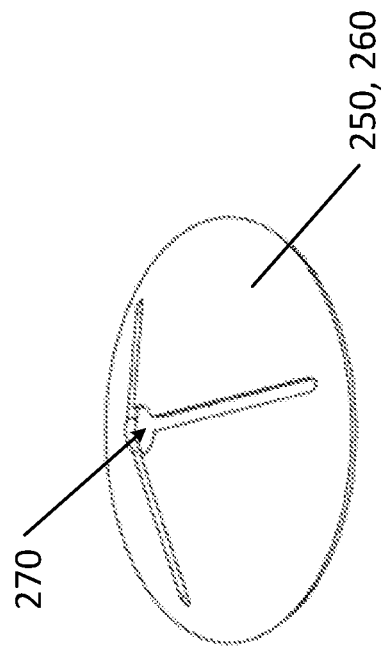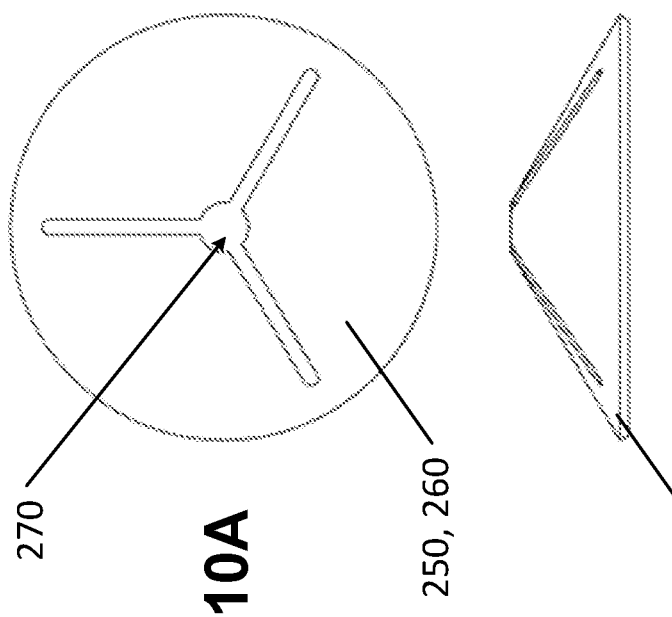
FIG. 10A
FIG. 10B
FIG. 10C

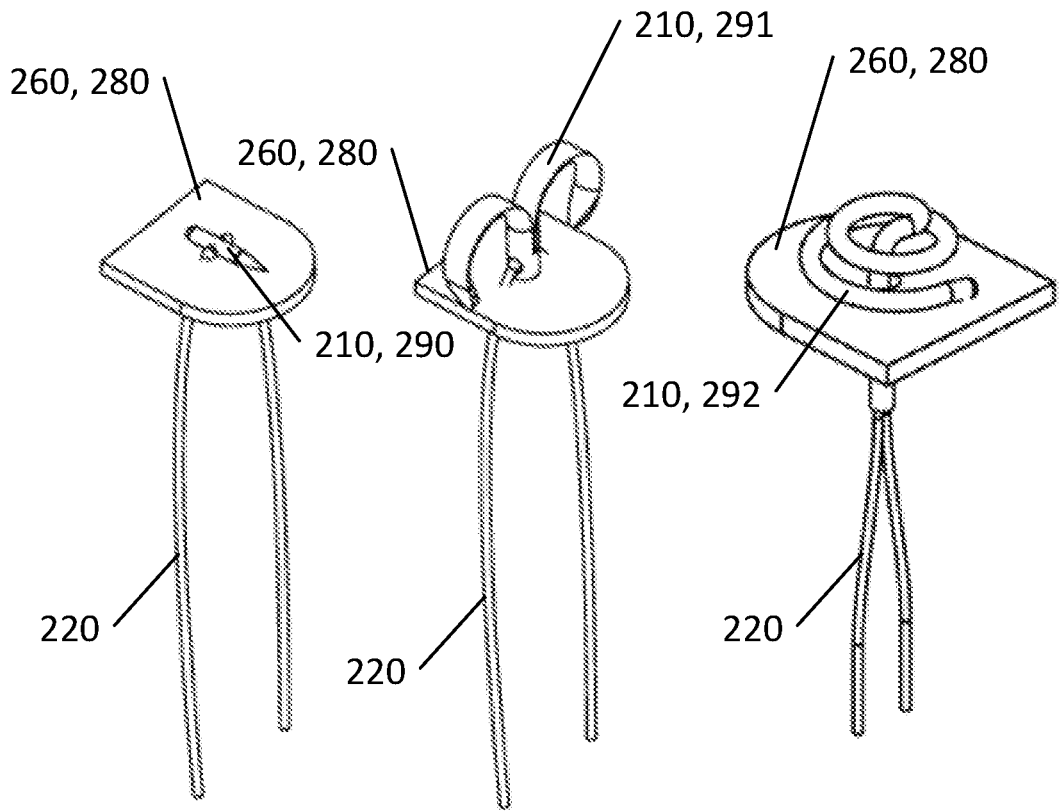
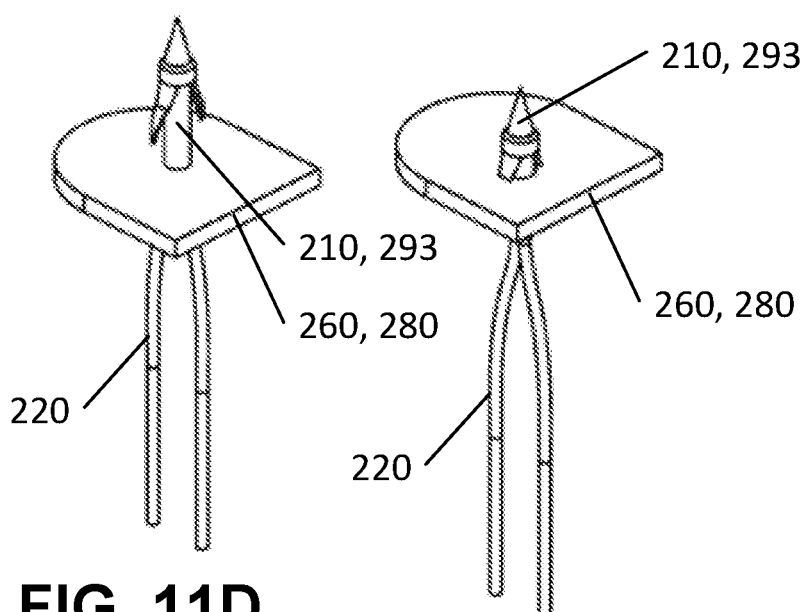

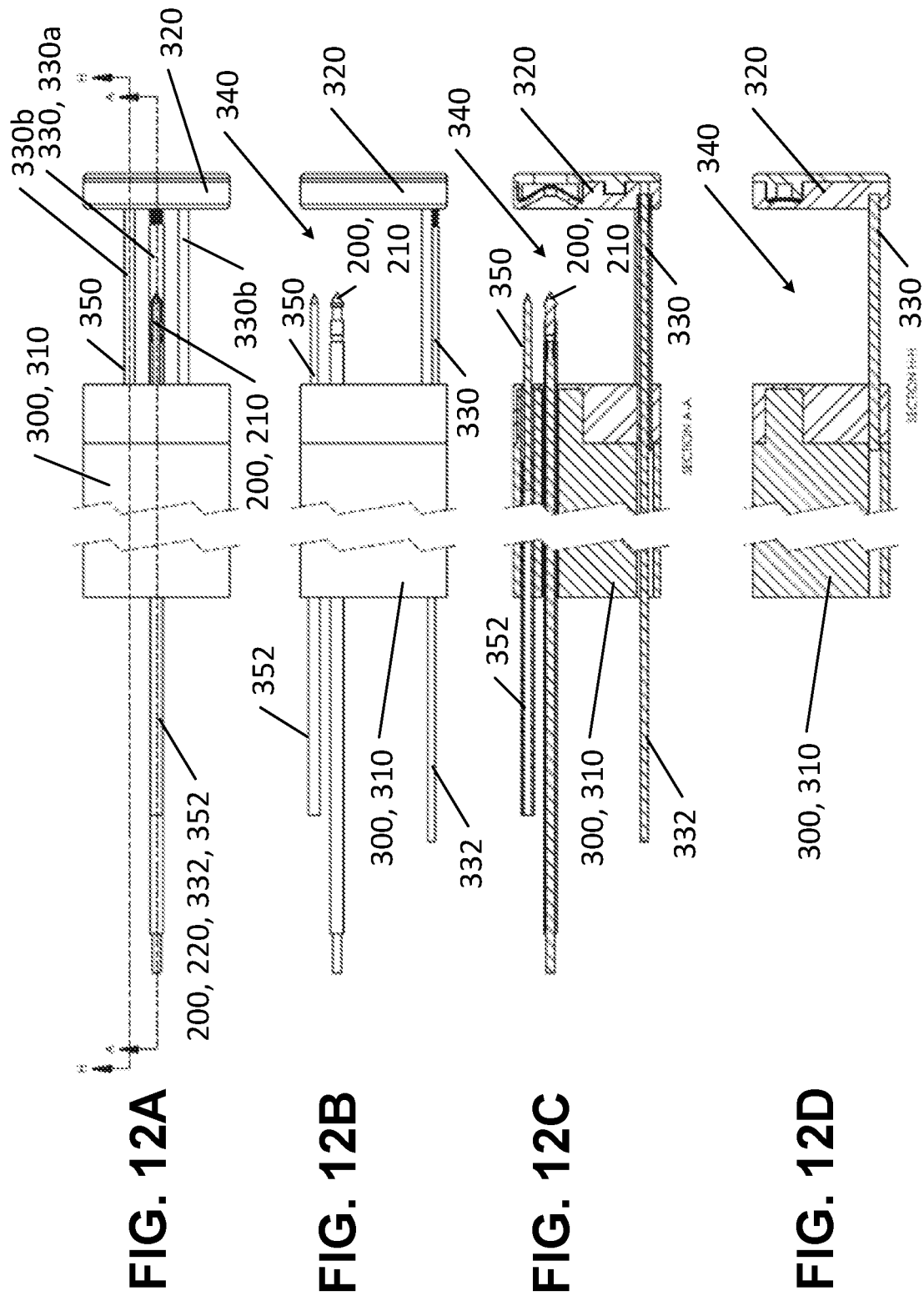

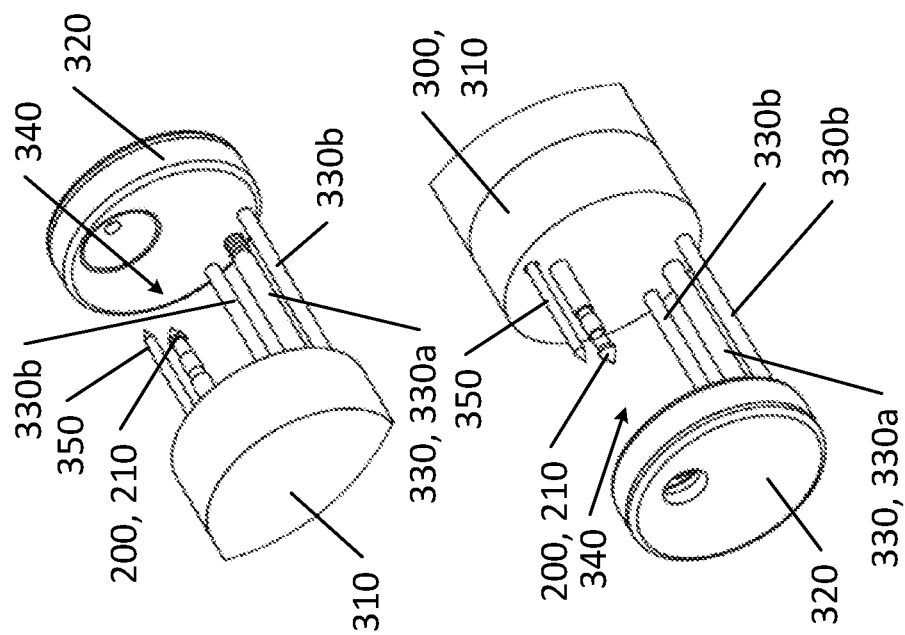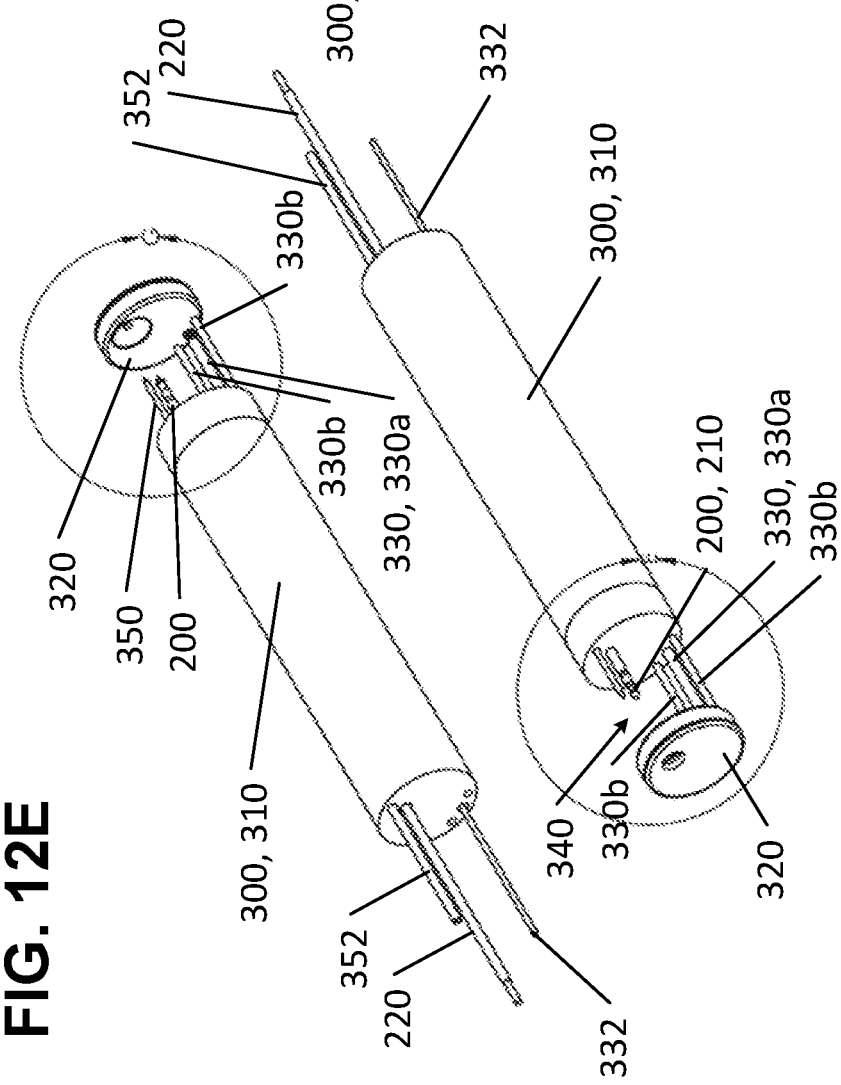

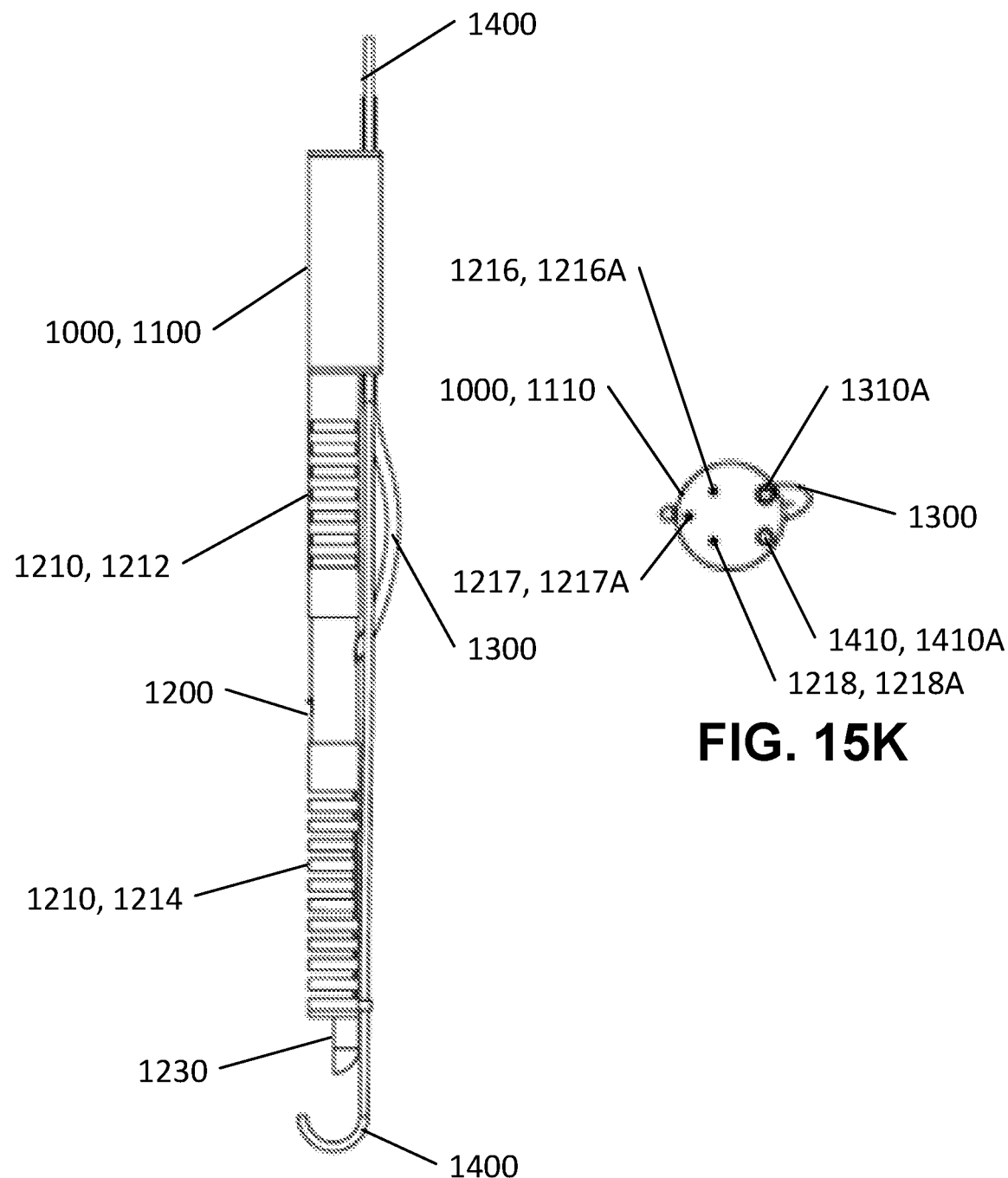

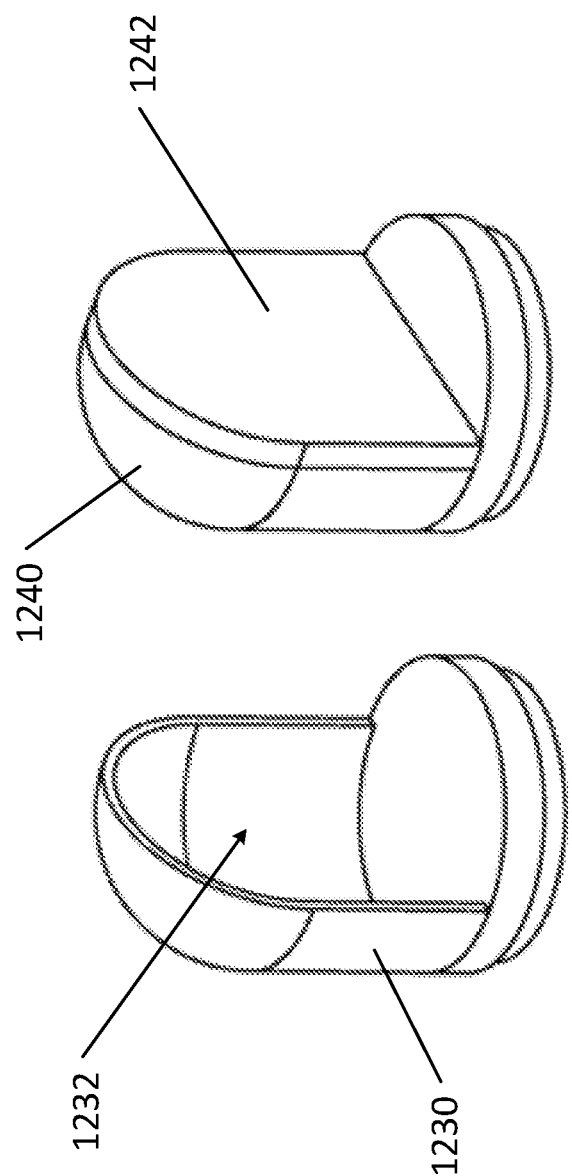

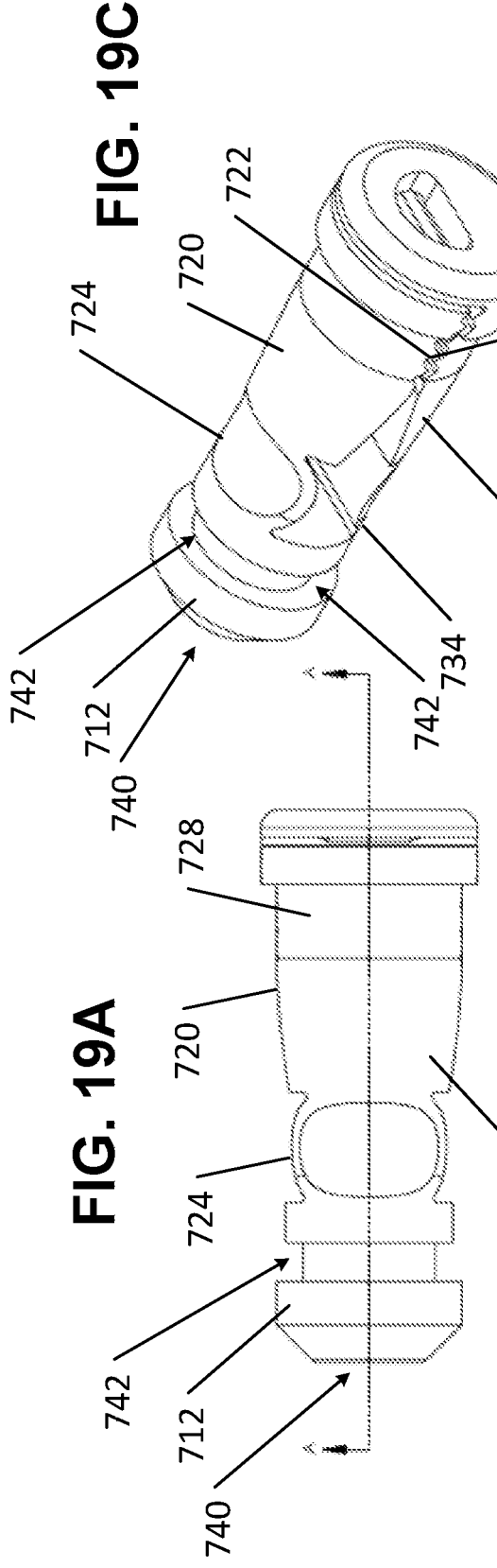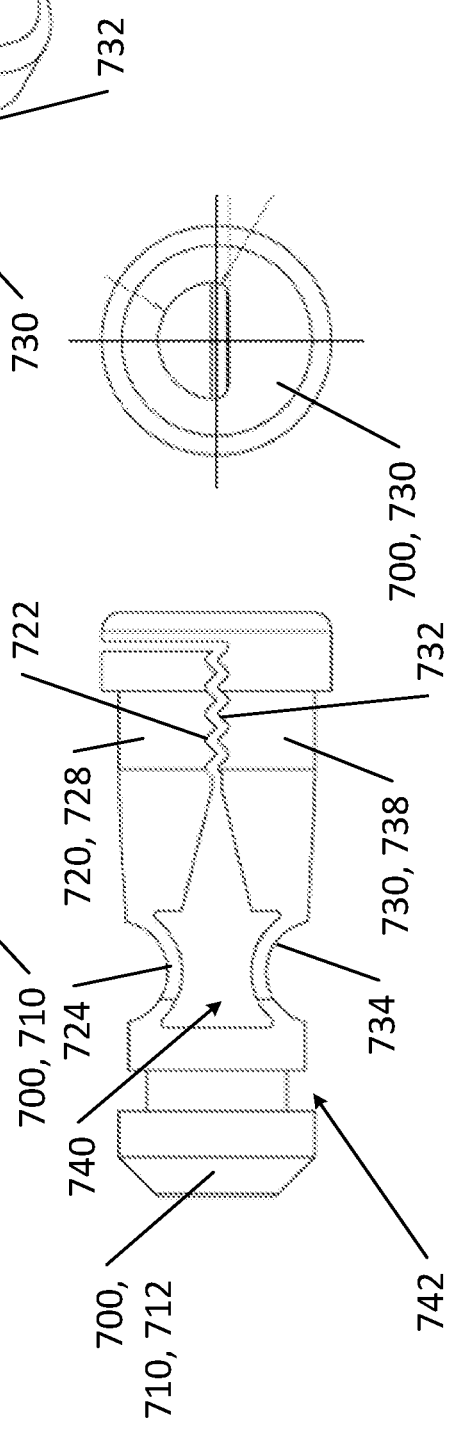

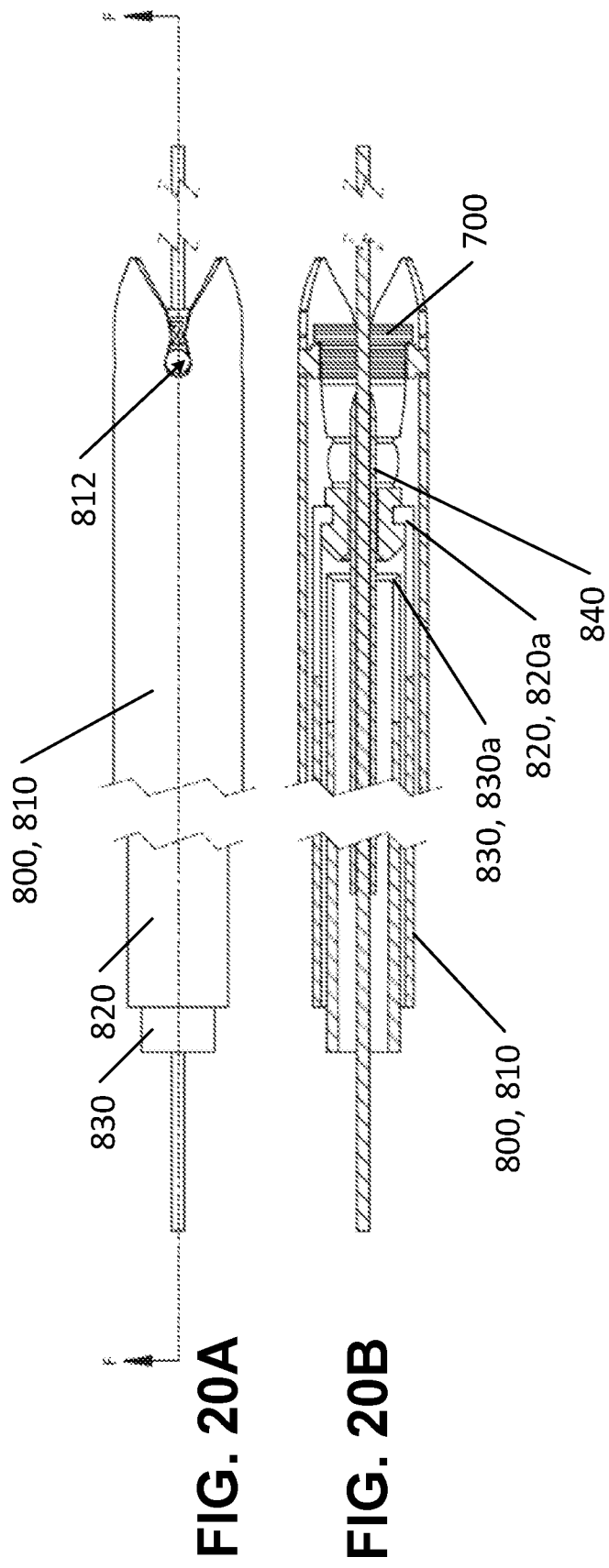

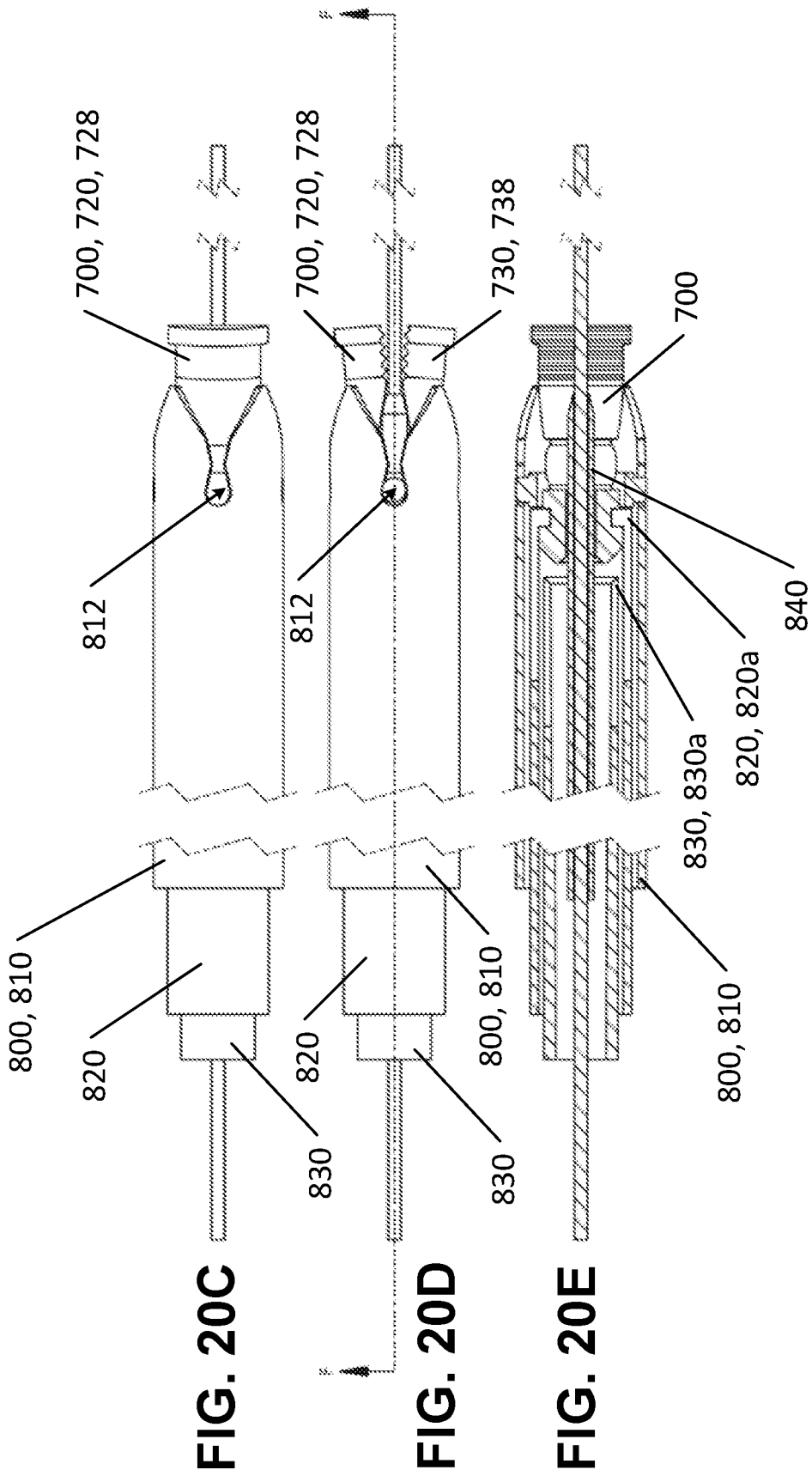

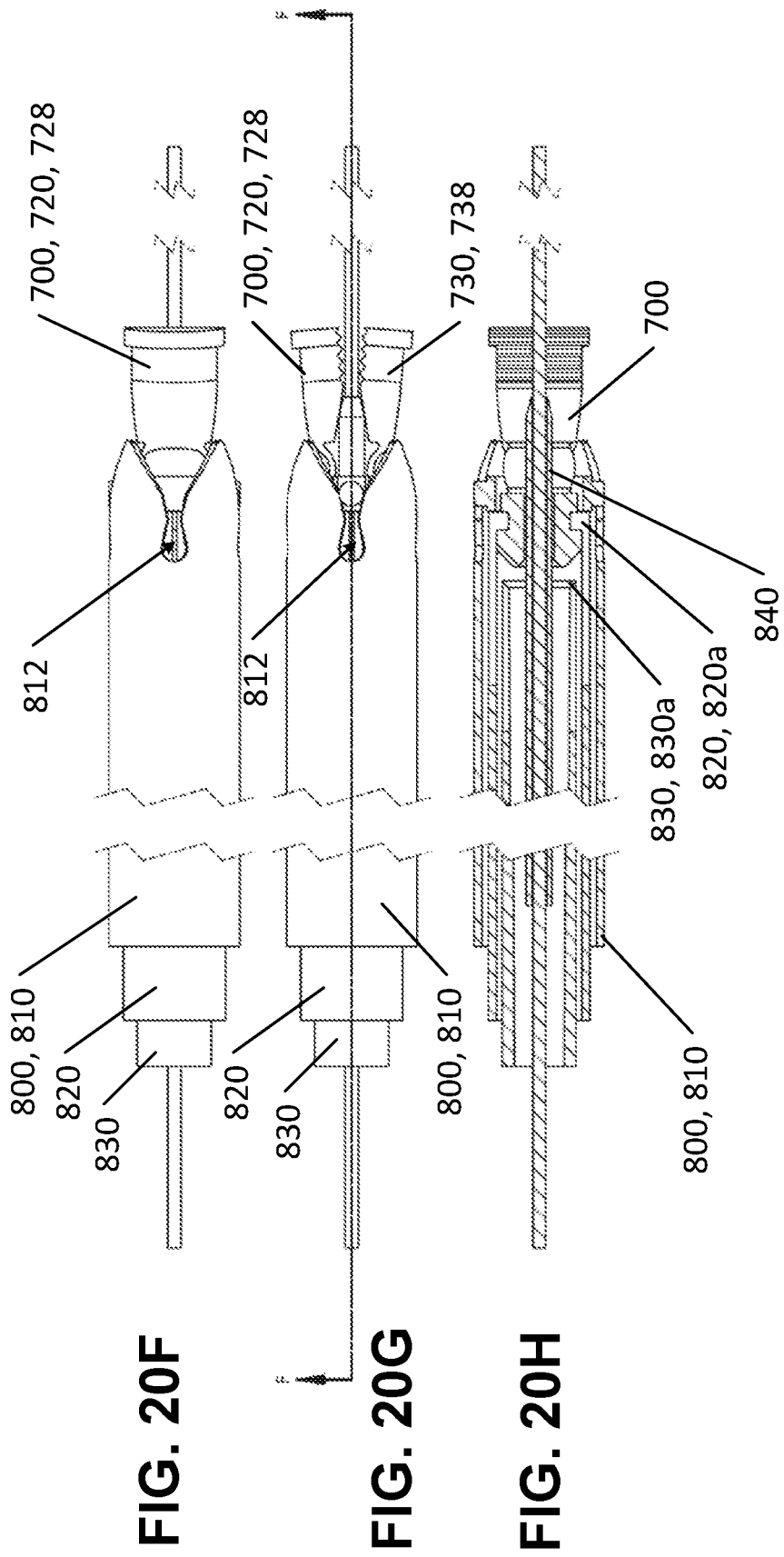

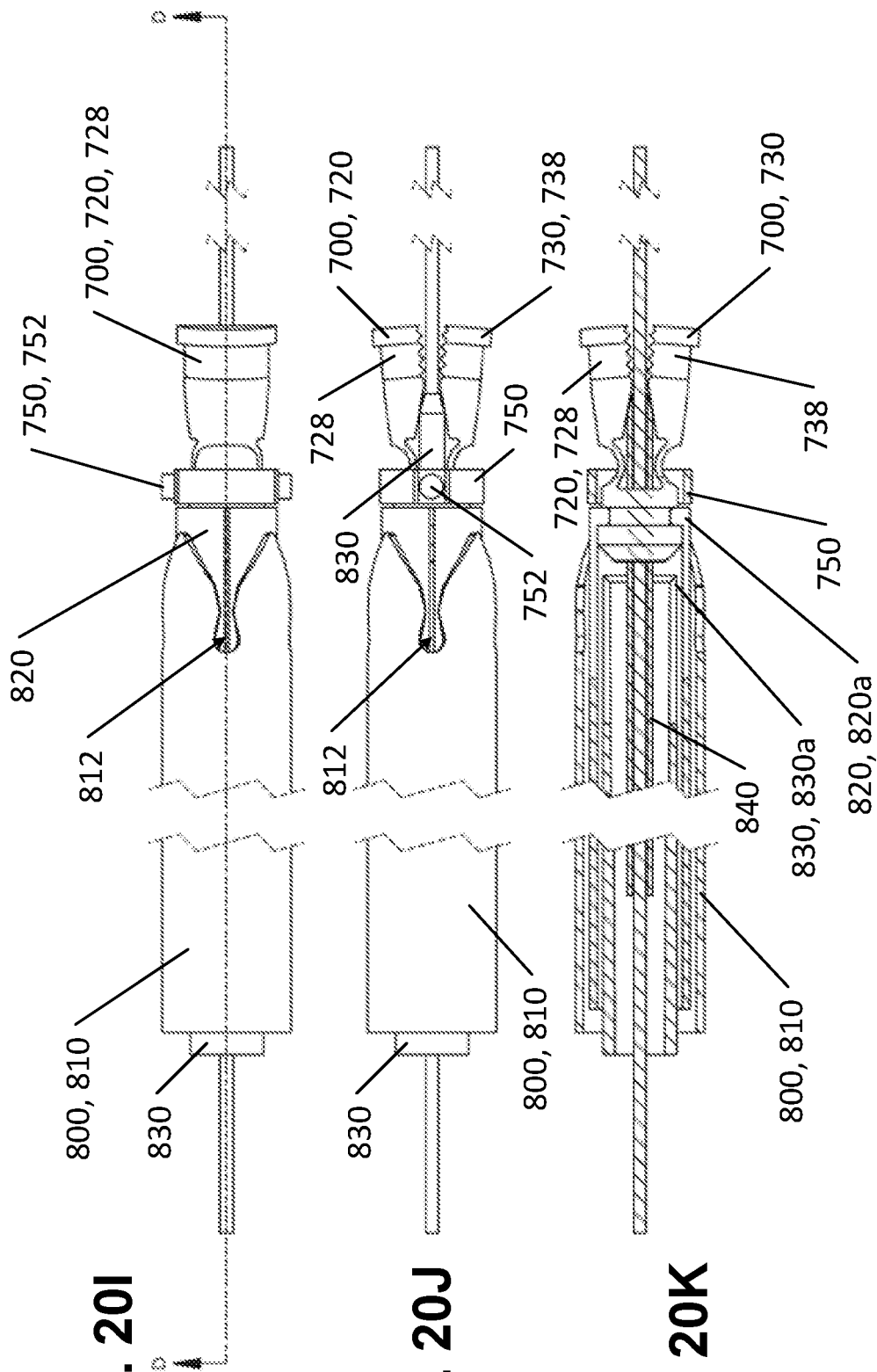

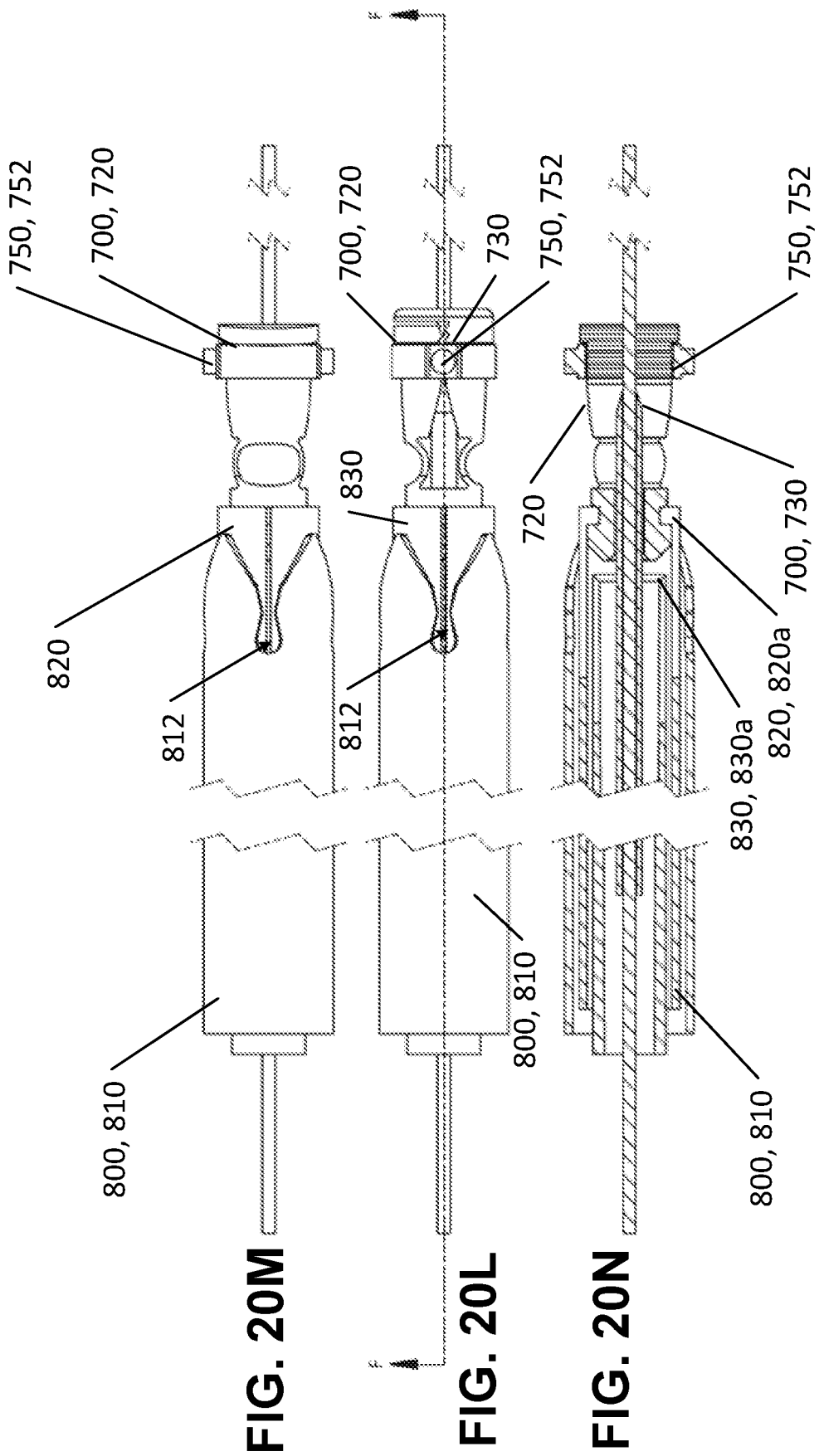

APPARATUS FOR USE IN REPAIRING MITRAL VALVES AND METHOD OF USE THEREOF

CROSS-REFERENCE TO RELATED APPLICATIONS

This application is a continuation of U.S. application Ser. No. 17/426,046 entitled APPARATUS FOR USE IN REPAIRING MITRAL VALVES AND METHOD OF USE THEREOF, which is a 371 of PCT application No. PCT/CA2020/050095 filed 27 Jan. 2020, which claims the benefit of U.S. application No. 62/797,778 filed 28 Jan. 2019, all of which are hereby incorporated herein by reference for all purposes. For purposes of the United States of America, this application claims the benefit under 35 U.S.C. § 119 of U.S. application No. 62/797,778 filed 28 Jan. 2019 entitled APPARATUS FOR USE IN REPAIRING MITRAL VALVES AND METHOD OF USE THEREOF which is hereby incorporated herein by reference for all purposes.

TECHNICAL FIELD

The present invention relates to apparatus for use in repairing heart valves and methods of use thereof. In particular, the present invention relates to apparatus for use in repairing mitral valves and methods of use thereof.

BACKGROUND

The mitral valve is the most complex of the human heart's valves and is commonly associated with disease. Conditions affecting the normal functioning of the mitral valve include, for example, mitral valve regurgitation, mitral valve prolapse, and mitral valve stenosis. Mitral valve regurgitation refers to the condition whereby the leaflets of the mitral valve fail to coapt into apposition during ventricular contraction, resulting in abnormal leaking of blood from the left ventricle into the left atrium. Mitral valve prolapse refers to the condition where the mitral leaflets bulge abnormally up into the left atrium causing irregular behaviour of the mitral valve. Mitral valve stenosis refers to the narrowing of the heart's mitral valve obstructing blood flow. A number of factors may affect the normal functioning of the mitral leaflets.

Although intermediate grades of impaired functioning of the mitral valve may not require treatment, severely impaired mitral valve function may result in symptoms (for example, breathlessness, fatigue, exercise intolerance), and may represent a threat to life expectancy. Often, invasive surgery must be performed to repair or replace an abnormal mitral valve.

Traditionally, repairing or replacing a mitral valve involves an open heart procedure. Open heart procedures present patients with morbidity and mortality risks and require a post-op period of convalescence that is typically several months in duration. Open heart surgery may pose prohibitive risks, or may otherwise not be ideal for some patients, including some elderly patients and patients with other health issues. Repairing or replacing the mitral valve without invasive open heart procedures may be attractive therapy for such patients.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides an apparatus for repairing a heart valve. The apparatus comprises a body, a member attached to the body at a first end and having a plurality of positioning cords spaced laterally across the member and extending away from a second end of the member opposed to the first end, a tube suspended from the plurality of positioning cords, and an adjustment cord extending through the tube. The plurality of positioning cords is spaced laterally across the tube. The tube may be lengthened or shortened by tensioning the adjustment cord.

In some embodiments, the member has a net-like structure. The net-like structure can be defined by a plurality of cells. The plurality of cells extends radially and longitudinally from the body to the positioning cords. In some embodiments, the plurality of cells has a diamond shape. In some embodiments, the plurality of cells has a square or rectangular shape.

In some embodiment tensioning the adjustment cord lengthens or shortens the tube consequently displacing the tube towards or away from the body causing corresponding displacement of the member.

In some embodiment the length of each positioning cord is selected to suspend the tube from the member in a parabolic or parabolic-like shape.

In some embodiment lengthening the tube consequently displaces a vertex of the parabolic or parabolic-like shaped tube towards the body.

In some embodiments shortening the tube consequently displaces a vertex of the parabolic or parabolic-like shaped tube away from the body.

In some embodiments the apparatus comprises an encircling member connectable to the body for radially compressing and/or radially expanding the body.

In some embodiments the body comprises a plurality of peaks and a plurality of troughs, the peaks and troughs defined interchangeably along the diameter of the body.

In some embodiments the body comprises a plurality of ring members, each ring member positioned on a corresponding peak.

In some embodiments the encircling member passes through the plurality of ring members.

In some embodiments the body defines at least one anchoring site.

In some embodiments the body comprises a skirt.

In some embodiments the skirt defines at least one anchoring site.

In some embodiments the apparatus is configured to extend from an atrial wall and a mitral annulus to an anterior-lateral papillary muscle and a posterior-medial papillary muscle of the heart valve when the apparatus is implanted in the heart valve.

In some embodiments the member comprises an anterior member attached to an anterior end of the body.

In some embodiments the member comprises a posterior member attached to a posterior end of the body.

In some embodiments the anterior member is configured to cover an anterior mitral leaflet of the heart valve when the apparatus is implanted in the heart valve.

In some embodiments the posterior member is configured to cover a posterior mitral leaflet of the heart valve when the apparatus is implanted in the heart valve.

In some embodiments the member comprises a biocompatible, blood-permeable material that permits the passage of blood therethrough.

Another aspect of the invention provides an annular anchor comprising an anchor pin, a tether connected to the anchor pin, and a guidewire connected to the tether. The length of the guidewire is at least sufficient to traverse a patient's circulatory system from a mitral annulus to an access site of the patient's circulatory system.

In some embodiments the anchor pin comprises a shape-memory material.

In some embodiments the anchor pin comprises a deformed configuration for advancing the anchor through a patient's circulatory system within a catheter.

In some embodiments the anchor pin comprises a pre-deformed configuration for anchoring the anchor in an annular tissue of a heart.

Another aspect of the invention provides an annular anchor catheter comprising a catheter body and a sensor attached to the body for detecting contact between the catheter and an annular wall of a mitral annulus of a heart.

In some embodiment the catheter comprises a needle housed within the catheter body and configured to retain an annular anchor.

Another aspect of the invention provides a method for implanting an annular anchor. The method comprises advancing a catheter to an anchor site located at an annular wall of a mitral annulus of a heart, detecting contact between the catheter and the anchor site, and advancing an annular anchor from the catheter and embedding the annular anchor in the mitral annulus.

In some embodiments advancing the annular anchor comprises advancing a needle housing the annular anchor through the annular wall and advancing the annular anchor from the needle to embed the annular anchor in the mitral annulus.

Another aspect of the invention provides a papillary anchor comprising an anchor pin, at least one tether connected to the anchor pin, and a guidewire connected to each tether. The length of each guidewire is at least sufficient to traverse a patient's circulatory system from a papillary muscle to an access site of the patient's circulatory system.

In some embodiments the anchor pin comprises a shape-memory material.

In some embodiments the anchor pin comprises a deformed configuration for advancing the anchor through a patient's circulatory system within a catheter.

In some embodiments the anchor pin comprises a pre-deformed configuration for securing the anchor through a papillary muscle of a heart.

Another aspect of the invention provides a papillary anchor catheter comprising a body configured to house a papillary anchor, an arm extending away from the body, and a receiver connected to the arm for receiving the papillary anchor. The body, arm, and receiver define an opening configured to receive a papillary muscle.

In some embodiments the receiver is detachable from the arm.

In some embodiments the arm is retractable inside the body.

In some embodiments the body comprises a retaining pin extendable from the body to close the opening.

In some embodiments the retaining pin is retractable inside the body to open the opening.

In some embodiments the catheter comprises a controller for operating one or more of the retaining pin and the arm externally.

Another aspect of the invention provides a method for implanting a papillary anchor. The method comprises advancing a papillary anchor catheter in a closed configuration through a patient's circulatory system to a papillary muscle, opening the catheter to receive a papillary muscle, positioning the papillary muscle within the opening, advancing the papillary anchor from the catheter through the papillary muscle, receiving an anchor pin of the papillary anchor with a receiver of the catheter, detaching the receiver from the catheter leaving the papillary anchor implanted in the papillary muscle and secured to the papillary muscle with the receiver, and withdrawing the catheter from the patient's circulatory.

In some embodiments the method comprises advancing the retaining pin at least partially through the papillary muscle to stabilize the papillary muscle prior to advancing the papillary anchor through the papillary muscle.

In some embodiments the method comprises retracting the retaining pin prior to withdrawing the catheter from the patient's circulatory system.

Another aspect of the invention provides a papillary anchor catheter comprising a body configured to house a papillary anchor and a deformable arm extending away from the body.

In some embodiments the body comprises a needle for housing the papillary anchor and advancing the papillary anchor through a papillary muscle.

In some embodiments the arm comprises a tensioning wire extending lengthwise through the arm for deforming the arm in a deformed configuration and an extended configuration by applying tension to the wire.

In some embodiments the arm comprises a plurality of modular pieces arranged linearly, wherein the tensioning wire extends through the pieces to deform the arm by applying tension to the tensioning wire.

In some embodiments the catheter comprises a controller for operating one or more of the needle and the tensioning wire externally.

Another aspect of the invention provides a method for implanting a papillary anchor. The method comprises advancing a papillary anchor catheter in an extended configuration through a patient's circulatory system to a papillary muscle, deforming the catheter into a deformed configuration to at least partially encircle a papillary muscle, advancing the papillary anchor from the catheter through the papillary muscle, extending the catheter into the extended configuration, and withdrawing the catheter from the patient's circulatory system in the extended configuration.

Another aspect of the invention provides a papillary anchor catheter comprising a body, a deformable arm extending from the body, and an anchor housing extending through the body and the arm, wherein the anchor housing is configured to house a papillary anchor.

In some embodiments the catheter comprises a guidewire extending through the body and alongside the arm, wherein the guidewire is extendable and retractable from the body.

In some embodiments a length of the guidewire is sufficient to traverse a patient's circulatory system from a papillary muscle to an access site to the patient's circulatory system.

In some embodiments the arm comprises at least one deformable section.

In some embodiments the arm comprises a first deformable section deformable in a first plane and a second deformable section deformable in a second plane.

In some embodiments the first deformable section is deformable in a first direction by about 0° to about 120° in the first plane.

In some embodiments the second deformable section is deformable in a second direction by about 0° to about 90° in the second plane and in a third direction by about 0° to about −90° in the second plane.

In some embodiments the first direction and the second direction are non-coplanar.

In some embodiments the catheter comprises a controller for operating one or more of the guidewire, the first deformable section, and the second deformable section externally.

Another aspect of the invention provides a method for implanting a papillary anchor. The method comprises advancing a papillary anchor catheter in an extended configuration through a patient's circulatory system to a papillary muscle, deforming the catheter in a first direction into a deflected configuration, advancing a guidewire to at least partially encircle a papillary muscle, deforming the catheter in a second direction into a deformed configuration, advancing the catheter along the guidewire to at least partially encircle the papillary muscle with the catheter, advancing the papillary anchor from the catheter through the papillary muscle, and withdrawing the catheter from the patient's circulatory system in the extended configuration.

In some embodiments advancing the papillary anchor through the papillary muscle comprises advancing the papillary anchor through a transverse dimension of the papillary muscle from an entrance site of the papillary muscle to an exit site of the papillary muscle.

In some embodiments advancing the papillary anchor through the papillary muscle further comprises receiving an anchor tip of the papillary anchor with a receiver of the catheter adjacent to the exit site.

In some embodiments withdrawing the catheter comprises extending the catheter into the extended configuration.

Another aspect of the invention provides a method of repairing a heart valve. The method comprises implanting at least one annular anchor in a mitral annulus of the heart valve, implanting a papillary anchor through each papillary muscle of the heart, delivering and positioning an apparatus for repairing a heart valve inside the heart valve using the at least one annular anchor and the papillary anchors, and adjusting the apparatus to adjust the extent of atrial displacement of the heart's mitral leaflets during ventricular contraction.

In some embodiments delivering the apparatus comprises externally connecting one or more guidewires of each annular anchor and one or more guidewires of each papillary anchor to the apparatus and advancing the apparatus along the guidewires to the heart valve.

In some embodiments delivering the apparatus further comprises externally advancing the one or more guidewires of each annular anchor through a body of the apparatus and advancing the body of the apparatus to an atrial wall of the mitral annulus of the heart valve.

In some embodiments delivering the apparatus comprises externally advancing the one or more guidewires of each papillary anchor through at least one compressible tube of the apparatus and advancing the at least one tube to extend between the papillary muscles of the heart valve in a parabolic or parabolic-like shaped configuration.

In some embodiments positioning the apparatus inside the heart valve comprises adjusting the length of the at least one tube to position the apparatus to cover an atrial surface of at least one mitral leaflet of the heart valve.

In some embodiments positioning the apparatus inside the heart valve further comprises adjusting the length of the at least one tube to adjust the position of at least one blood-permeable member of the apparatus to adjust the extent of atrial displacement of the at least one mitral leaflet during ventricular contraction.

In some embodiments delivering the apparatus comprises externally advancing a first guidewire of each papillary anchor through a first compressible tube of the apparatus and advancing a second guidewire of each papillary anchor through a second compressible tube of the apparatus and advancing the first and second tubes along the first and second guidewires to extend the first and second tubes between the papillary muscles of the heart valve in a parabolic or parabolic-like shaped configuration.

In some embodiments positioning the apparatus inside the heart valve further comprises adjusting the length of the first tube to position an anterior member of the apparatus to cover an atrial surface of an anterior mitral leaflet of the heart valve.

In some embodiments positioning the apparatus inside the heart valve further comprises adjusting the length of the first tube to adjust the position of the anterior member to adjust the extent of atrial displacement of the anterior mitral leaflet during ventricular contraction.

In some embodiments positioning the apparatus inside the heart valve further comprises adjusting the length of the second tube to position a posterior member of the apparatus to cover an atrial surface of a posterior mitral leaflet of the heart valve.

In some embodiments positioning the apparatus inside the heart valve comprises adjusting the length of the second tube to adjust the position of the posterior member to adjust the extent of atrial displacement of the posterior mitral leaflet during ventricular contraction.

In some embodiments the method comprises securing the apparatus to an atrial wall of the heart valve.

In some embodiments the method comprises securing the apparatus to each papillary muscle of the heart valve.

In some embodiments securing the apparatus to the atrial wall comprises advancing a lock in an open configuration to an anchor site of the apparatus and positioning the lock in a locked configuration adjacent the atrial wall at each anchor site.

In some embodiments securing the apparatus to the papillary muscles comprises advancing a lock in an open configuration along each papillary anchor and positioning the lock in a locked configuration adjacent the papillary muscle.

Another aspect of the invention provides a lock comprising a body defining opposed jaws and a channel extending lengthwise through the body and between the jaws. The lock is deformable in an open configuration by deflecting the jaws away from each other.

In some embodiments the jaws define a recess shaped concentrically about the channel and configured to receive a collar for retaining the lock in a locked configuration.

In some embodiments the collar comprises at least one notch configured to engage a lock catheter.

In some embodiments the body defines a groove shaped concentrically about the channel and configured to engage the lock catheter.

In some embodiments each jaw comprises a set of teeth.

Another aspect of the invention provides a lock catheter comprising a sleeve tube, a lock tube, and a deploying tube. The sleeve tube houses the lock tube and the lock tube houses the deploying tube.

In some embodiment the catheter comprises a needle extending through a channel defined by the deploying tube.

In some embodiments the sleeve tube defines a notch for engaging a lock.

Another aspect of the invention provides a method for securing an apparatus inside a heart valve. The method comprises advancing a lock in an open configuration along a guidewire to a lock site and advancing a collar along the lock at the lock site to lock the lock in a closed configuration.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 6A is a side elevation view of an annular anchor catheter according to an example embodiment of the present invention advanced towards an annular wall of the heart shown in FIG. 1.

FIG. 6B is a side elevation view of the heart and catheter shown in FIG. 6A, wherein the needle is advanced into the annular wall of the heart.

FIG. 6C is a side elevation view of the heart and catheter shown in FIG. 6A having an anchor according to an example embodiment of the present invention advancing from the needle.

FIG. 6D is a side elevation view of the heart, catheter, and anchor shown in FIG. 6C, wherein the anchor is advanced from the needle.

FIG. 6E is a side elevation view of the heart, catheter, and anchor shown in FIG. 6C, wherein the anchor is implanted into the mitral annulus of the heart.

FIG. 6F is a side elevation view of the heart, catheter, and anchor shown in FIG. 6C, wherein the anchor is implanted into the mitral annulus of the heart and the needle is retracted into the catheter.

FIG. 7D is a partial front elevation partial view of the anchor shown in FIG. 7A.

FIG. 7E is a top elevation view of the anchor shown in FIG. 7A.

FIG. 7F is a partial side elevation view of the anchor shown in FIG. 7A.

FIG. 8A is a side elevation view of an anchor according to an example embodiment of the present invention.

FIG. 8B is a side perspective view of the anchor shown in FIG. 8A.

FIG. 8C is side perspective cross-sectional view of the anchor shown in FIG. 8A taken along the line B-B.

FIG. 10A is a top view of an anchor fastener according to an example embodiment of the present invention.

FIG. 10B is a side elevation view of the anchor fastener shown in FIG. 10A.

FIG. 10C is a top side perspective view of the anchor fastener shown in FIG. 10A.

FIG. 11A is a perspective view of an anchor and anchor fastener according to an example embodiment of the present invention.

FIG. 11B is a perspective view of an anchor and anchor fastener according to an example embodiment of the present invention.

FIG. 11C is a perspective view of an anchor and anchor fastener according to an example embodiment of the present invention.

FIG. 11D is a perspective view of an anchor and anchor fastener according to an example embodiment of the present invention.

FIG. 11E is a perspective view of the anchor and anchor fastener shown in FIG.

FIG. 12A is a side elevation view of a papillary anchor catheter according to an example embodiment of the present invention in a closed configuration, wherein an anchor extends therethrough.

FIG. 12B is a side elevation view of the catheter and anchor shown in FIG. 12A in an open configuration.

FIG. 12C is a side elevation cross-sectional view of the catheter and anchor shown in FIG. 12A taken along the line A-A.

FIG. 12D is a side elevation cross-sectional view of the catheter shown in FIG. 12A taken along the line H-H.

FIG. 12E is a rear side perspective view of the catheter and anchor shown in FIG. 12A in an open configuration.

FIG. 12F is a front side perspective view of the catheter and anchor shown in FIG. 12A in an open configuration.

FIG. 12G is a partial rear side perspective view of the catheter and anchor shown in FIG. 12A in an open configuration.

FIG. 12H is a partial front side perspective view of the catheter and anchor shown in FIG. 12A in an open configuration.

FIG. 15J is a side elevation view of the catheter shown in FIG. 15A in the extended configuration.

FIG. 15K is a top view of the catheter shown in FIG. 15A in the extended configuration.

FIG. 16A is a perspective view of a papillary catheter receiver according to an example embodiment of the present invention.

FIG. 16B is a perspective view of a papillary catheter receiver according to an example embodiment of the present invention.

FIG. 19A is a top elevation view of a lock according to an example embodiment of the present invention.

FIG. 19B is a side elevation view of the lock shown in FIG. 19A.

FIG. 19C is a front top side perspective view of the lock shown in FIG. 19A.

FIG. 19D is a front side view of the lock shown in FIG. 19A.

FIG. 20A is a top elevation view of a lock catheter according to an example embodiment of the present invention.

FIG. 20B is a cross-sectional view of the catheter shown in FIG. 20A taken along the line F-F, wherein the catheter contains the lock shown in FIG. 19A.

FIG. 20C is a top elevation view of the catheter shown in FIG. 20A advancing the lock shown in FIG. 19A along a guidewire in an open configuration.

FIG. 20D is a side elevation view of the catheter and lock shown in FIG. 20C.

FIG. 20E is a cross-sectional view of the catheter and lock shown in FIG. 20D taken along the line F-F.

FIG. 20F is a top elevation view of the catheter shown in FIG. 20A advancing the lock shown in FIG. 19A further along the guidewire in an open configuration.

FIG. 20G is a side elevation view of the catheter and lock shown in FIG. 20F.

FIG. 20H is a cross-sectional view of the catheter and lock shown in FIG. 20G taken along the line F-F.

FIG. 20I is a top elevation view of the lock catheter shown in FIG. 20A advancing the lock shown in FIG. 19A further along a guidewire in an open configuration.

FIG. 20J is a side elevation view of the catheter and lock shown in FIG. 20I.

FIG. 20K is a side cross-sectional view of the catheter and lock shown in FIG. 20I taken along the line D-D.

FIG. 20L is a side elevation view of the lock catheter shown in FIG. 20A securing the lock shown in FIG. 19A in a closed configuration to a guidewire.

FIG. 20M is a top elevation view of the catheter and lock shown in FIG. 20L.

FIG. 20N is a side cross-section view of the catheter and lock shown in FIG. 20L taken along the line F-F.

DESCRIPTION

Figure 1:
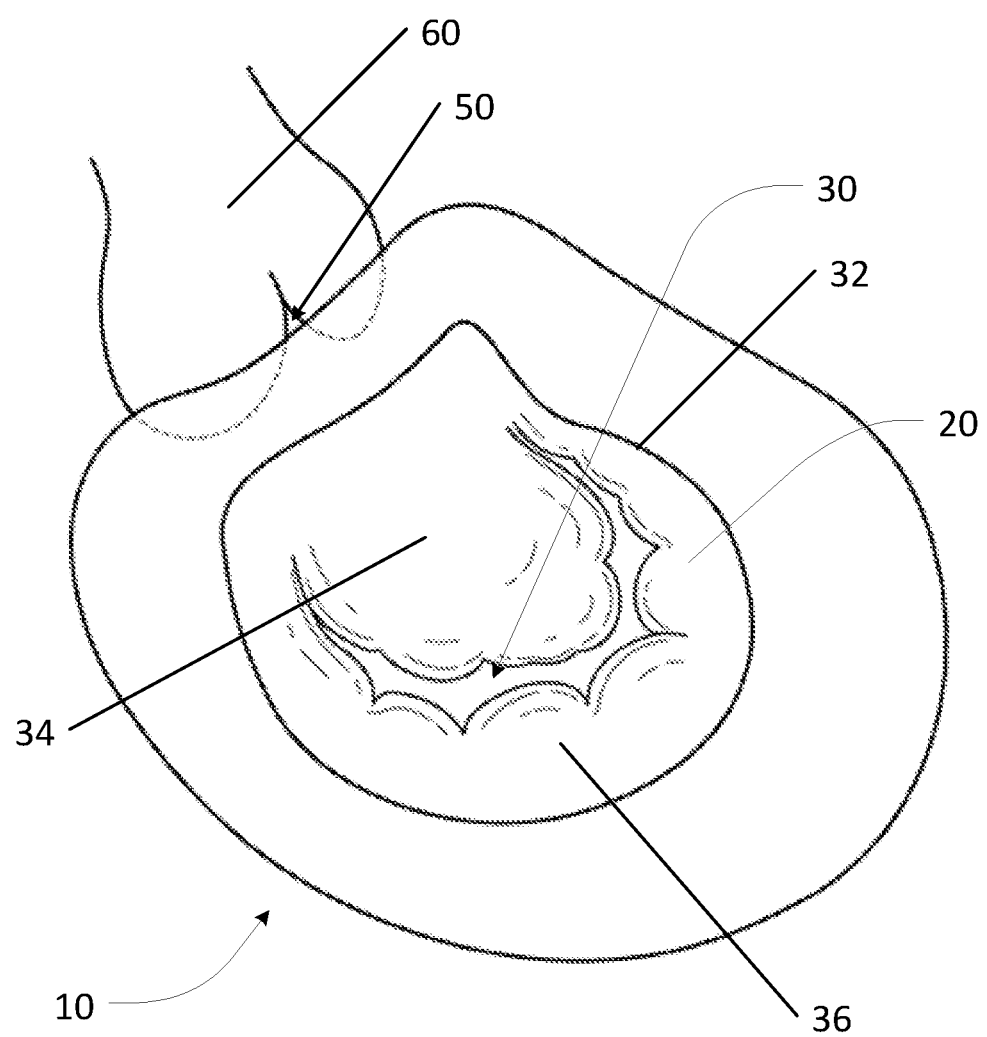
FIG. 1 is a top cross-sectional view of a heart showing normal coaptation of the mitral valve.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless context dictates otherwise, the term "anterior" (as used herein in relation to a patient's body and parts thereof) refers to a position that is more near the front surface of the patient's body or part thereof than the rear surface of the patient's body or part thereof.

Unless context dictates otherwise, the term "posterior" (as used herein in relation to a patient's body and parts thereof) refers to a position that is more near the rear surface of the patient's body or part thereof than the front surface of the patient's body or part thereof.

Unless context dictates otherwise, the terms "percutaneous", "percutaneously", and the like (as used herein) refer to a method of accessing a patient's circulatory system and/or heart through the skin, such as by needle access.

Unless context dictates otherwise, the term "antegrade" (as used herein) refers to a percutaneous approach to a mitral valve via the femoral vein, right atrium, atrial septal puncture, and left atrium (i.e. in the normal direction of blood flow through a patient's circulatory system).

Unless context dictates otherwise, the term "retrograde" (as used herein) refers to a percutaneous approach to the mitral valve via the femoral artery, wherein the left ventricle is accessed via the aortic valve (i.e. in reverse of the normal direction of blood flow through a patient's circulatory system).

Unless context dictates otherwise, the term "intravascular" (as used herein) means situated or occurring with a blood vessel or circulatory system.

Unless context dictates otherwise, the term "external" (as used herein in relation to a patient's body and parts thereof) means situated outside of a patient's circulatory system or body.

Unless context dictates otherwise, the term "transcatheter" (as used herein) refers to a method performed through the lumen of a catheter.

Unless context dictates otherwise, the term "circulatory system" (as used herein) refers to a system that circulates blood and/or lymph through a patient's body, consisting of one or more of the heart, blood vessels, blood, lymph, and the lymphatic vessels and glands.

Although the methods and apparatus of the present invention may be used for the percutaneous repair of any of the cardiac valves, the following description will focus on the repair of mitral valves. Further, while the methods and apparatus of the present invention will preferably be percutaneous and intravascular, such methods and apparatus may be used for performing open heart surgery where the heart is accessed through the myocardial tissue and/or in minimally invasive procedures where access to the heart is achieved thoracopically. Further still, while the methods and apparatus of the present invention may be used with conventional transcatheter valve prostheses, such methods and apparatus may be used with prostheses implanted through the myocardial tissue of the heart and/or prostheses implanted using minimally invasive procedures where access to the heart is achieved thoracopically. Further still, while the methods and apparatus of the present invention will use an antegrade approach (i.e. the access site of the patient's circulatory system being the femoral vein), the femoral artery may be favored in some embodiments as the access site for one or more of its size, ease of insertion, and least tortuous path to the heart.

Figure 2:
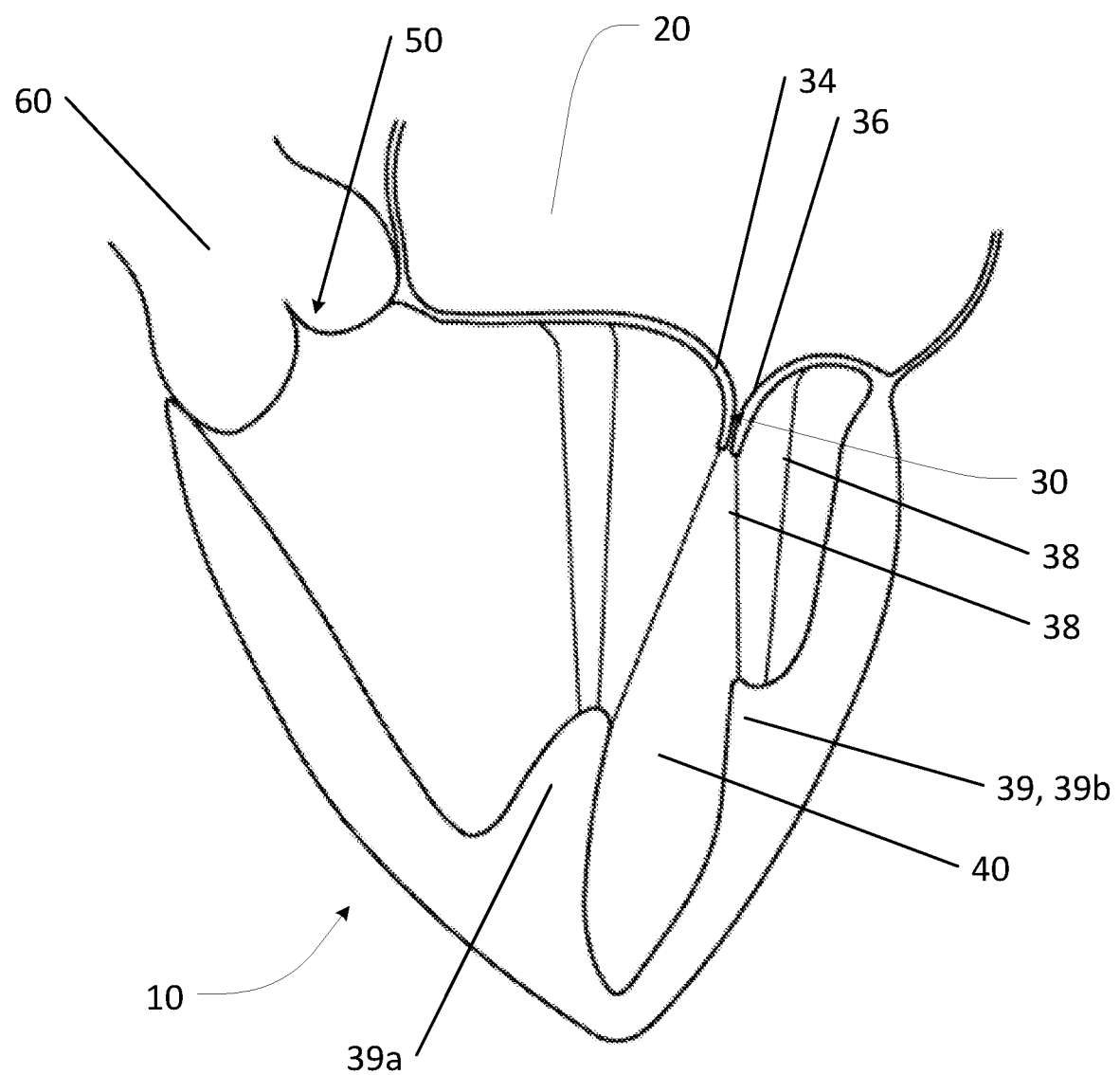
FIG. 2 is a side elevation cross-sectional view of the heart shown in FIG. 1.
Figure 5A:
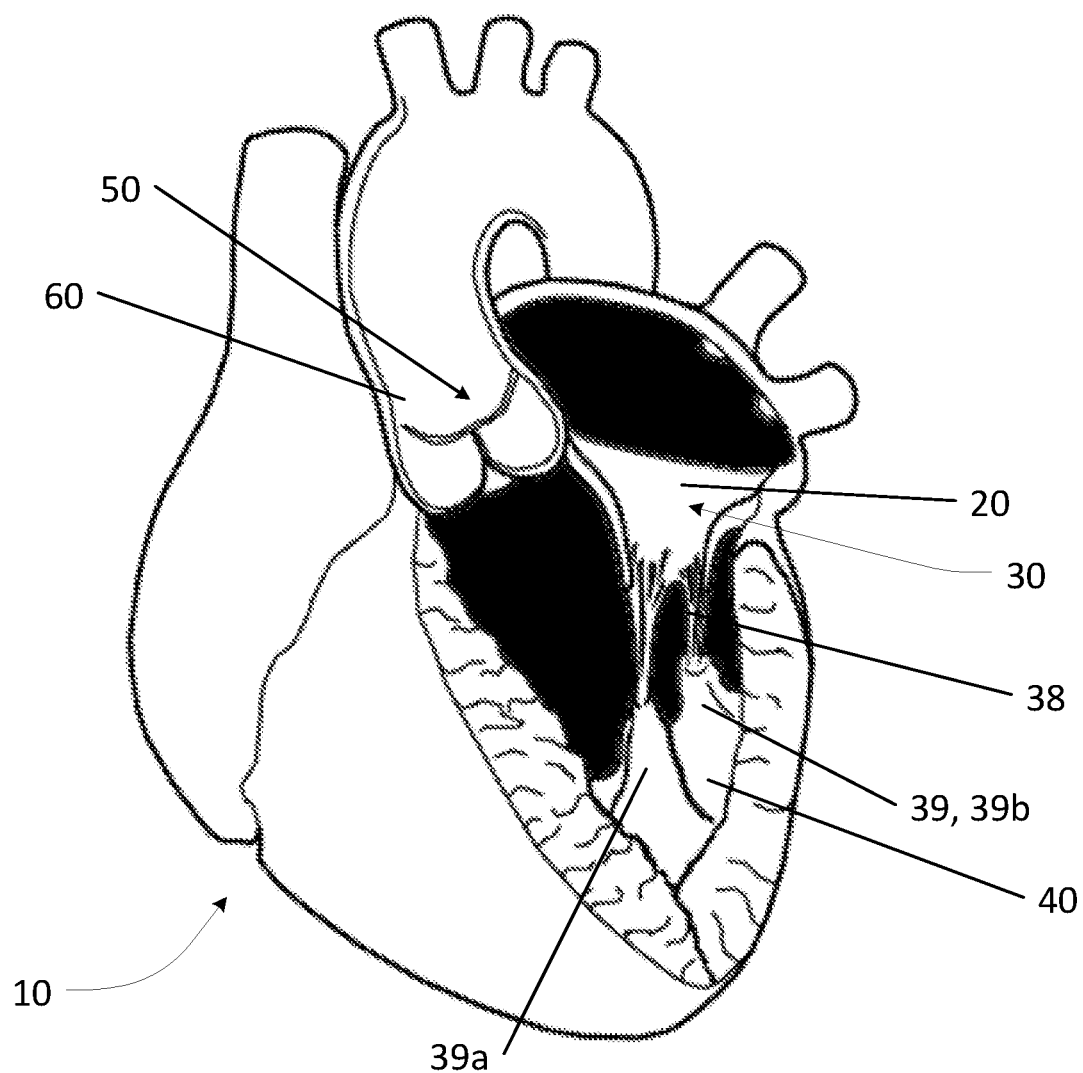
FIG. 5A is a perspective cross-sectional view of the heart shown in FIG. 1.
Figure 5B:
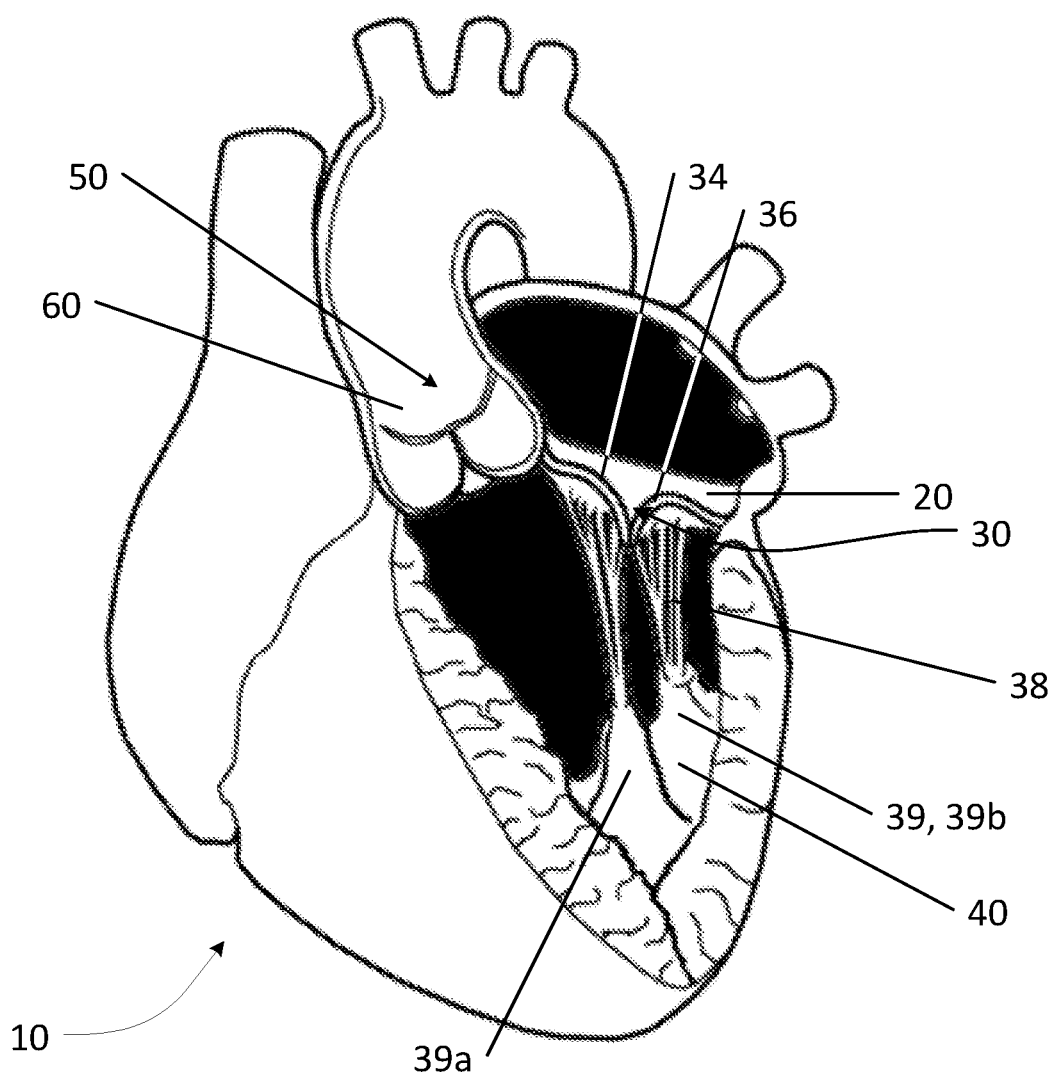
FIG. 5B is a perspective cross-sectional view of the heart shown in FIG. 5A showing normal coaptation of the mitral valve.

The human heart 10, shown in FIGS. 1, 5A, and 5B, is a muscle pump which relies on heart valves to achieve blood flow. In normal physiology, oxygenated blood returning from the lungs is collected in a left atrium 20, and then passes through a mitral (inlet) valve 30 to enter a left ventricle 40 (i.e. the pumping chamber). With contraction of left ventricle 40, the elevation of left ventricular pressure causes mitral valve 30 to close (FIGS. 2 and 5B), preventing reversal of blood flow back into atrium 20. As ventricular pressure exceeds aortic pressure, aortic (outlet) valve 50 opens (FIGS. 1 and 5A), and blood is pumped forward into aorta 60. When left ventricle 40 relaxes, the ventricular pressure drops, mitral valve 30 reopens to permit flow of blood from left atrium 20 to left ventricle 40, and the process repeats.

Mitral valve 30 separates left atrium 20 from left ventricle 40, and is comprised of a mitral annulus 32, leaflets (anterior 34 and posterior 36), chordae tendinae 38, and papillary muscles 39, 39a, 39b. During ventricular contraction (systole), the ventricular pressure rises, which forces displacement of mitral leaflets 34, 36 towards atrium 20 (i.e. commonly known as atrial or leaflet displacement). The length and integrity of chordae tendinae 38 determines the degree of leaflet displacement. In normal physiology, equal displacement of anterior mitral leaflet 34 and posterior mitral leaflet 36 results in contact (coaptation) between the leaflets, and consequent competence of mitral valve 30.

Figure 3:
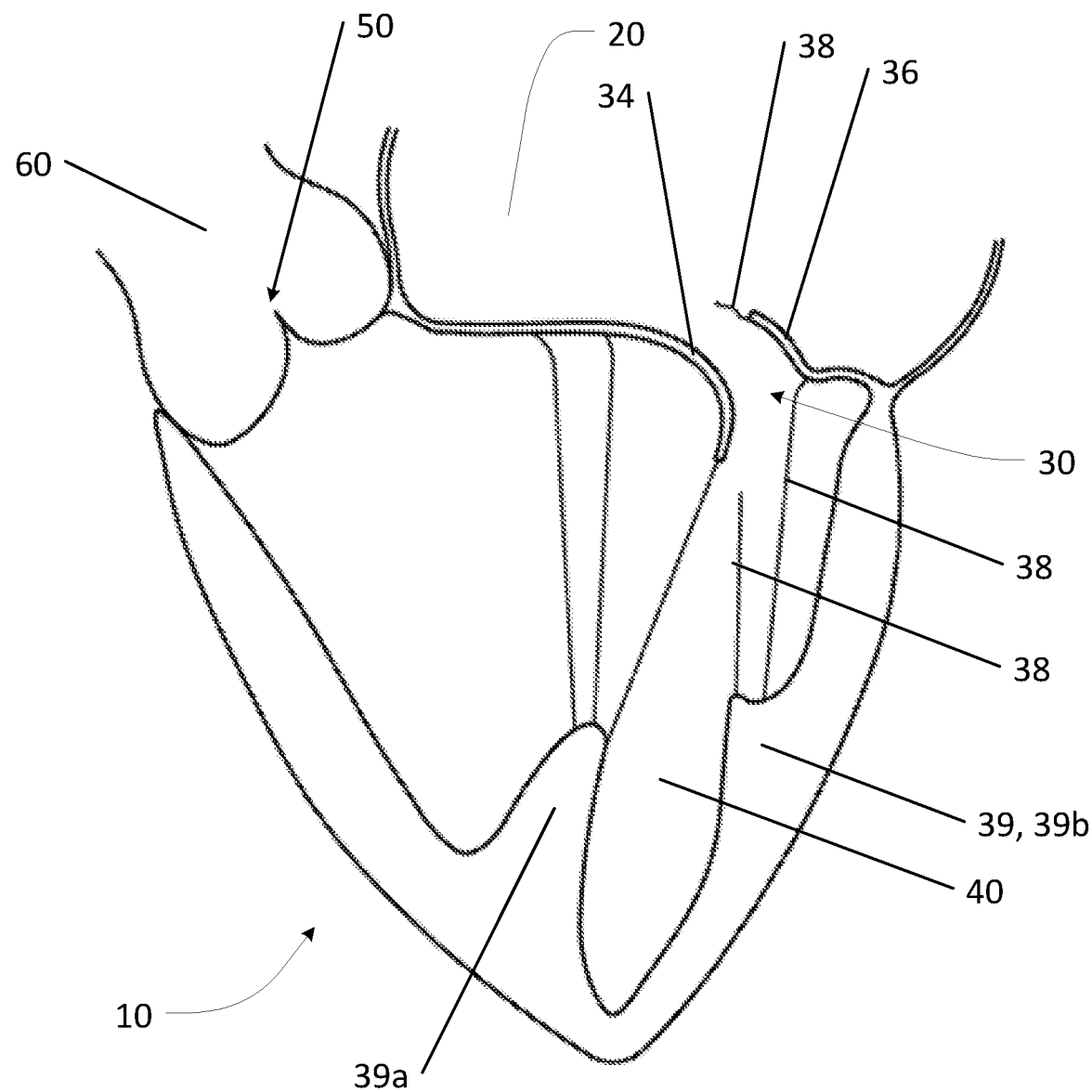
FIG. 3 is a side elevation cross-sectional view of a heart showing prolapse of a posterior mitral valve leaflet.

In circumstances where mitral leaflet 34 and/or 36 is supported by chordae tendinae 38 which are elongated or ruptured, ventricular contraction may result in excessive atrial displacement of the leaflet(s), and this may prevent coaptation between the leaflets (FIG. 3). This is referred to as mitral leaflet prolapse. In this circumstance, the competency of mitral valve 30 may be compromised and leakage may occur. Leakage through the mitral valve is referred to as mitral regurgitation, and when it is due to mitral leaflet prolapse it is referred to as degenerative mitral regurgitation. In other circumstances, the ventricular muscle itself can be diseased and its function impaired causing limited ventricular contraction and progressive ventricular dilation. Since mitral leaflets 34, 36 are attached by chordae tendinae 38 to the ventricular muscle, ventricular dilation can limit leaflet movement toward atrium 20 during contraction, resulting in poor leaflet coaptation and causing mitral regurgitation. This is referred to as functional mitral regurgitations.

An apparatus 100 for repairing a heart valve, such as a mitral valve, is shown in FIGS. 4A-4H. Apparatus 100 includes a radially compressible and radially expandable body 110, an anterior member 120, and a posterior member 130. Although the term "radial" is most commonly used in connection with circular objects or features, it should be understood for the purpose of this description and accompanying aspects that the term "radial" is used in a broader context and is not limited to describing strictly circular objects or features or objects or features with strictly circular cross-section. In some embodiments, anterior member 120 and posterior member 130 form a single member (not shown). In some other embodiments, apparatus 100 includes either anterior member 120 or posterior member 130, but not both.

In the embodiment shown in FIGS. 4A-4H body 110 comprises a radially compressible and radially expandable ring 112 attached to a skirt 114. Ring 112 includes a plurality of apertures 113, a plurality of peaks 115, and a plurality of troughs 117. Peaks 115 and troughs 117 are longitudinally spaced across ring 112. Apertures 113 are positioned on the peaks 115 and/or troughs 117 for radially compressing and/or radially expanding body 110. To radially compress and/or radially expand body 110, an encircling member (not shown) may be provided. The encircling member extends through ring members 113. By providing tension to first and second ends of the encircling member, body 110 may be radially compressed. Full radial expansion of body 110 is achieved by complete tension release of the encircling element within ring members 113. A "purse-string" effect may be achieved when tension is applied to the encircling member to radially compress body 110. Persons skilled in the art will recognize that body 110 may comprise any suitable radially compressible and radially expandable stent conventionally known. In some embodiments, the encircling element is not required to radially compress and/or radially expand body 110. For example, an inflatable balloon may be used to radially expand and contract body 110.

Anterior member 120 is connected to an anterior end 119 of body 110. Posterior member 130 is attached to a posterior end 118 of body 110. Each member 120, 130 comprises a section 122, 132 having a plurality of positioning cords 124, 134 for positioning each member to cover an atrial surface of a mitral leaflet from a lateral commissure to a medial commissure thereof. Cords 124, 134 are spaced laterally across each section 122, 132 and extend from section 122, 132 away from body 110. In some embodiments, cords 124, 134 are integrally formed with corresponding section 122, 132. Cords 124, 134 each terminate at and connect to a flexible, compressible tube 140, 150. Cords 124, 134 are laterally spaced across tube 140, 150. In some embodiments, the length of each cord 124, 134 is designed to suspend tube 140, 150 from section 122, 132 in a parabolic or parabolic-like shape. Thus, cords 124, 134 connect a ventricular perimeter 126, 136 of section 122, 132 with the corresponding tube 140, 150. In the FIGS. 4G and 4H embodiment, apparatus 100 comprises five cords 124, 134 suspending tubes 140, 150 from members 120, 130. Persons skilled in the art will recognize that apparatus 100 may comprises any number of cord(s) 124, 134 suitable for positioning member(s) 120, 130 to cover an atrial surface of a mitral leaflet as described elsewhere here.

Figure 4A:
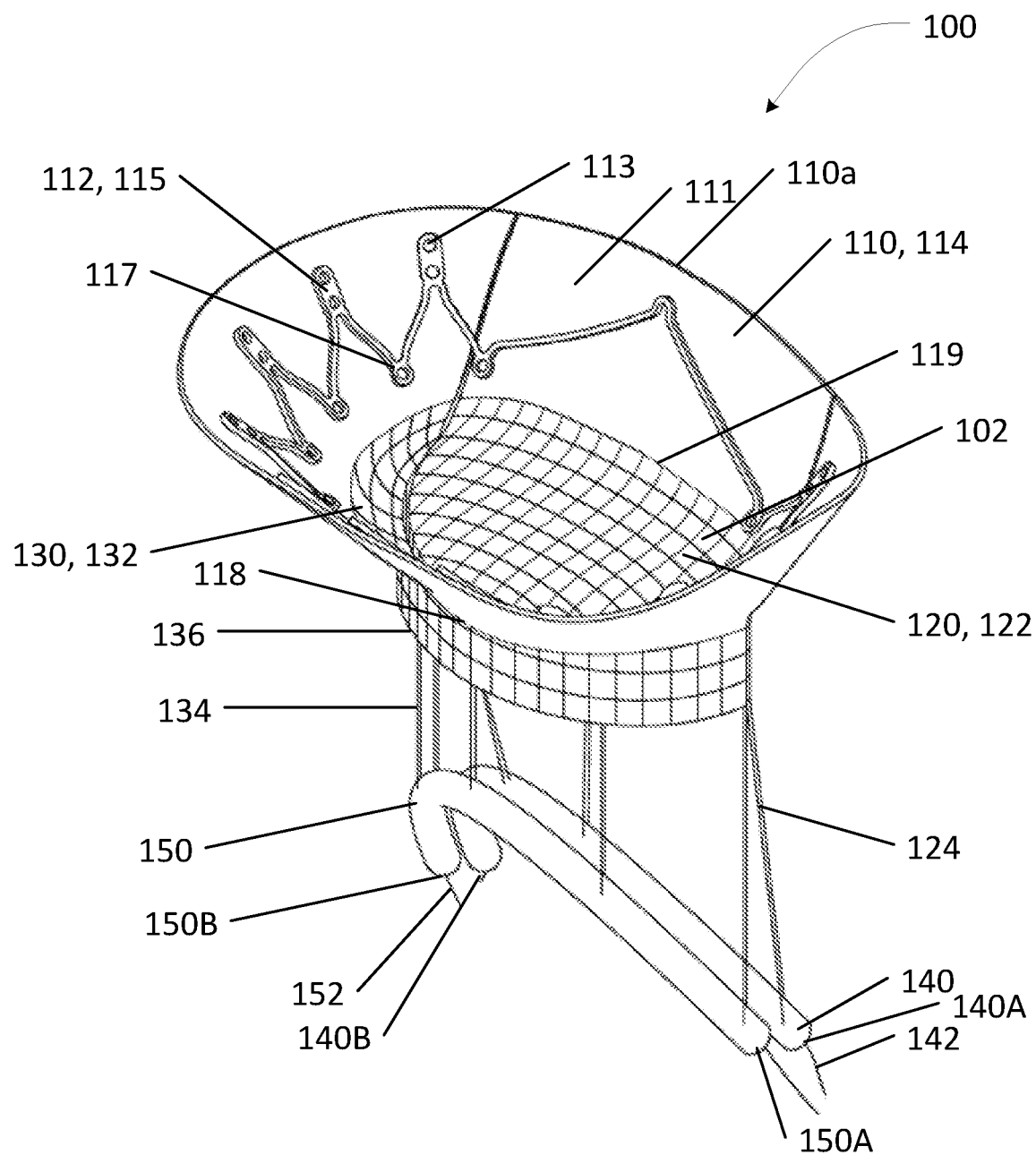
FIG. 4A is a top posterior perspective view of an apparatus according to an example embodiment of the present invention.
Figure 4B:
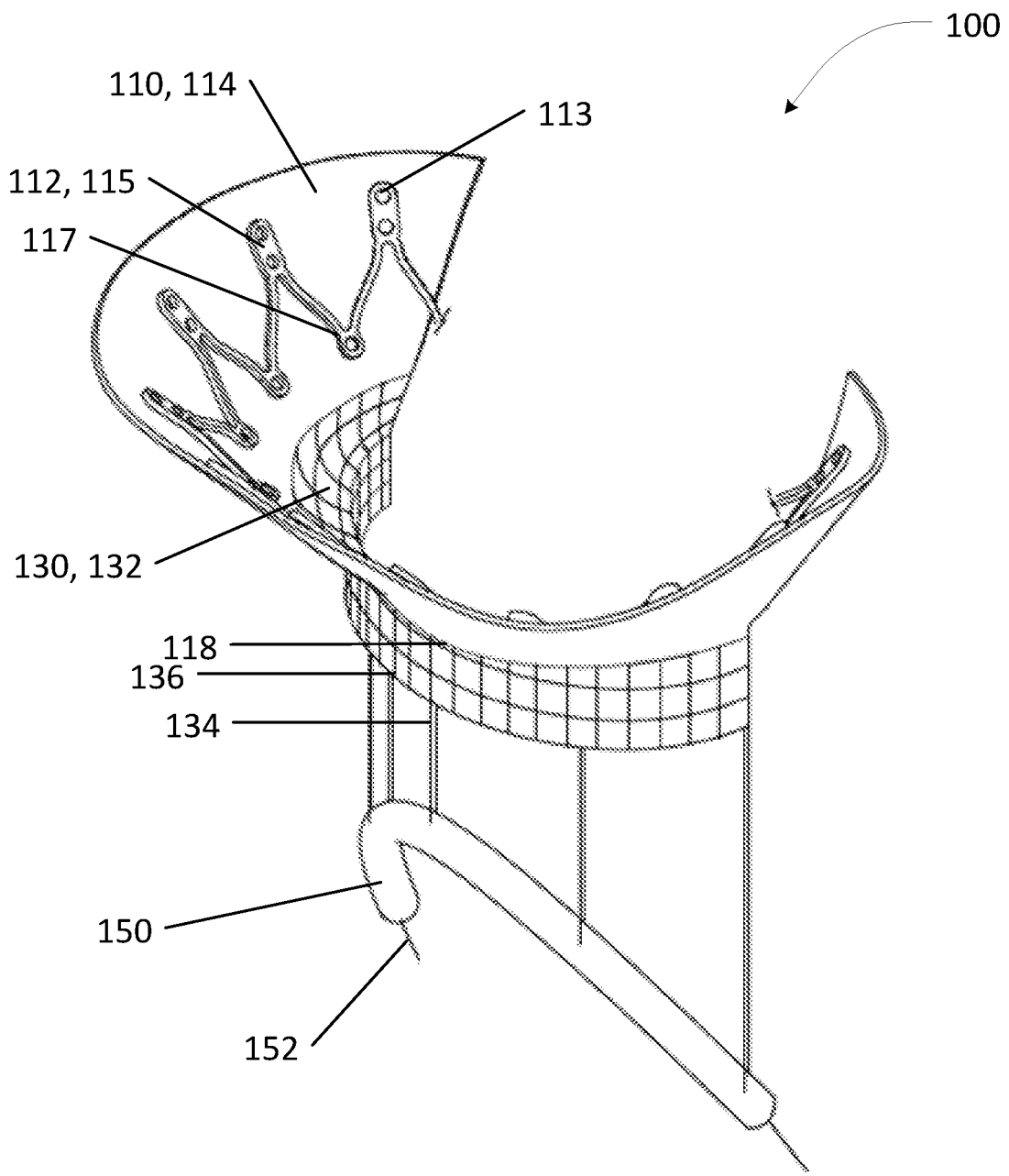
FIG. 4B is a partial top posterior perspective view of the apparatus shown in FIG. 4A.
Figure 4C:
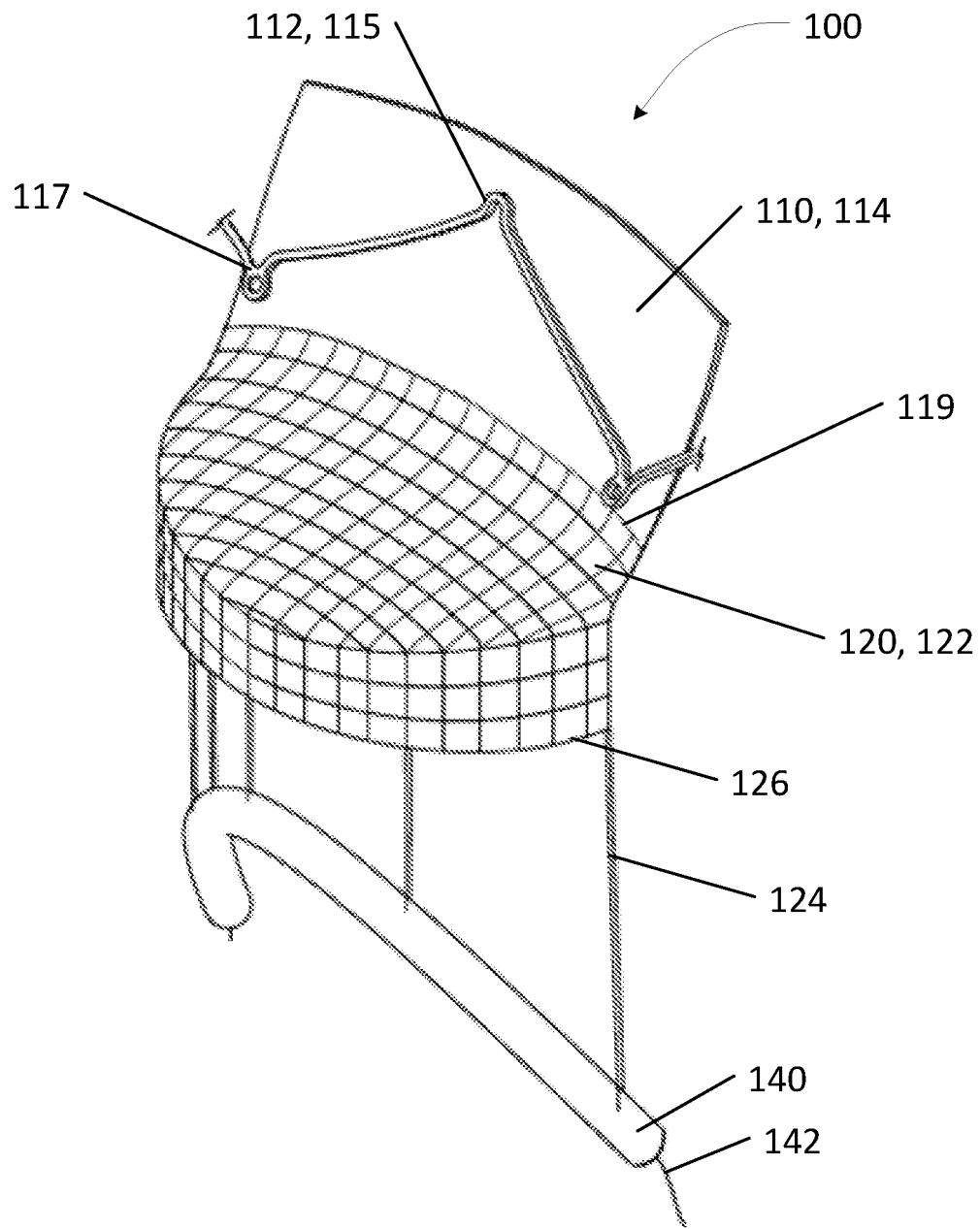
FIG. 4C is a partial top anterior perspective view of the apparatus shown in FIG. 4A.
Figure 4D:
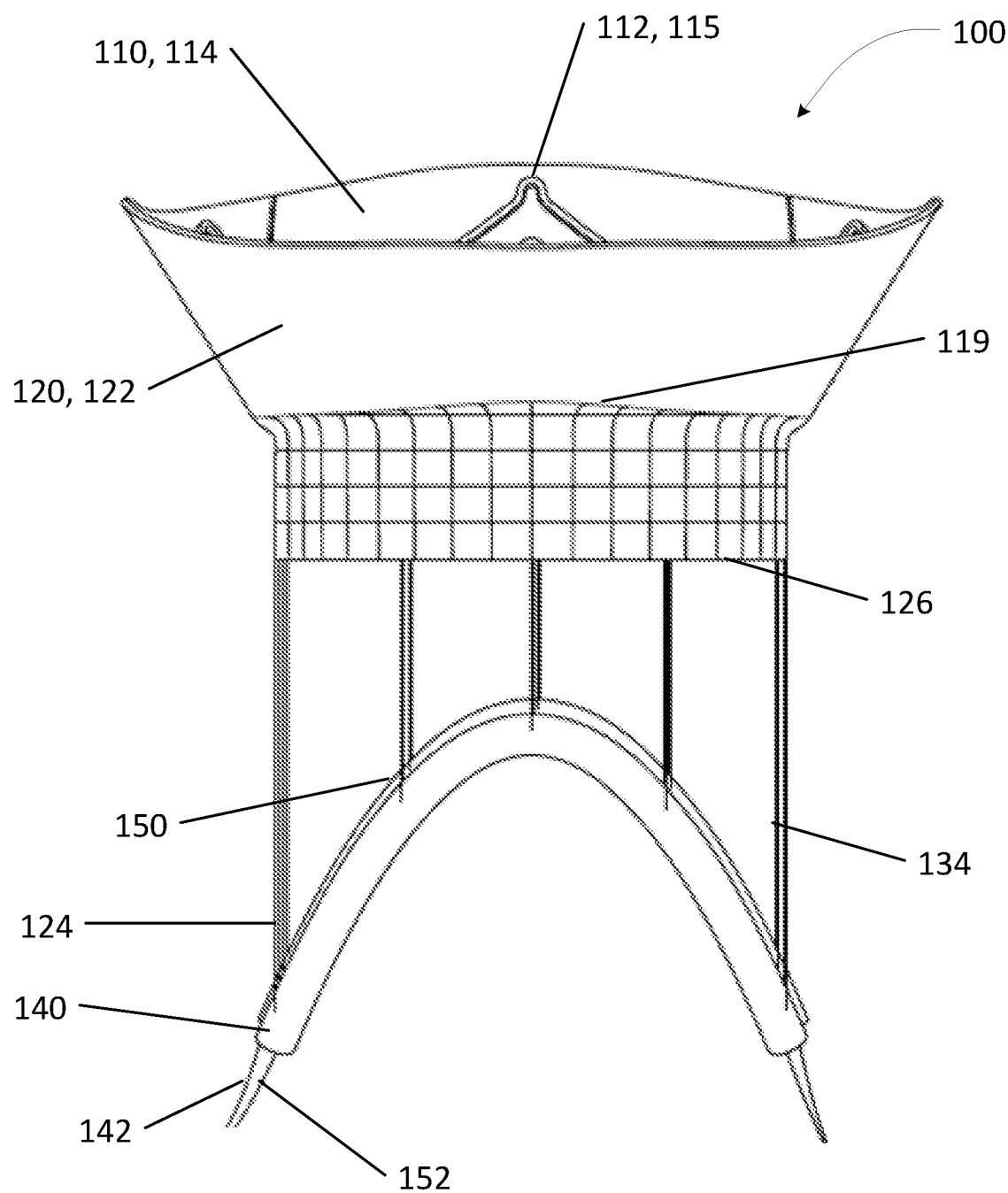
FIG. 4D is a posterior elevation view of the apparatus shown in FIG. 4A.
Figure 4E:
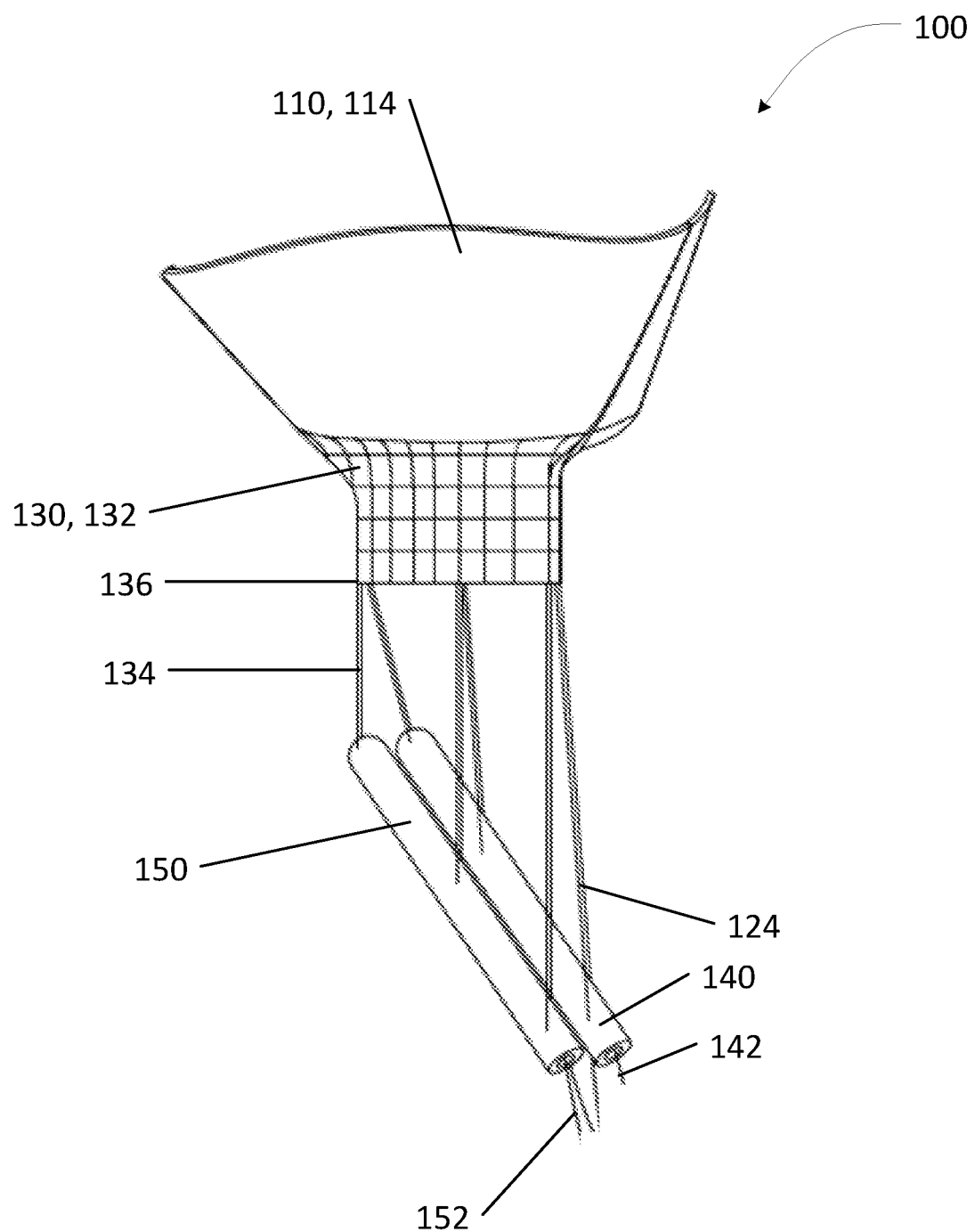
FIG. 4E is a side elevation view of the apparatus shown in FIG. 4A.
Figure 4F:
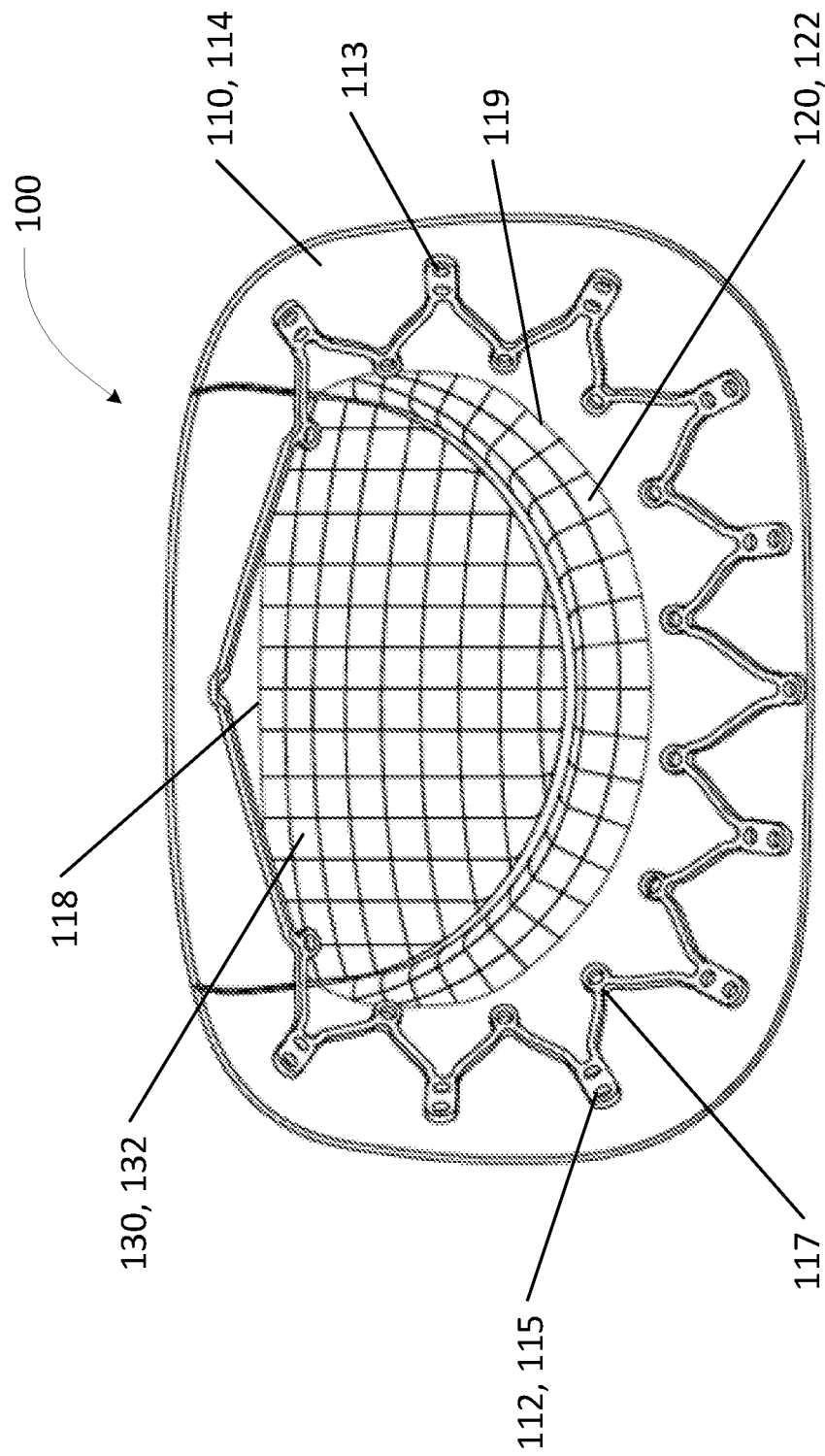
FIG. 4F is a top view of the apparatus shown in FIG. 4A.
Figure 4G:
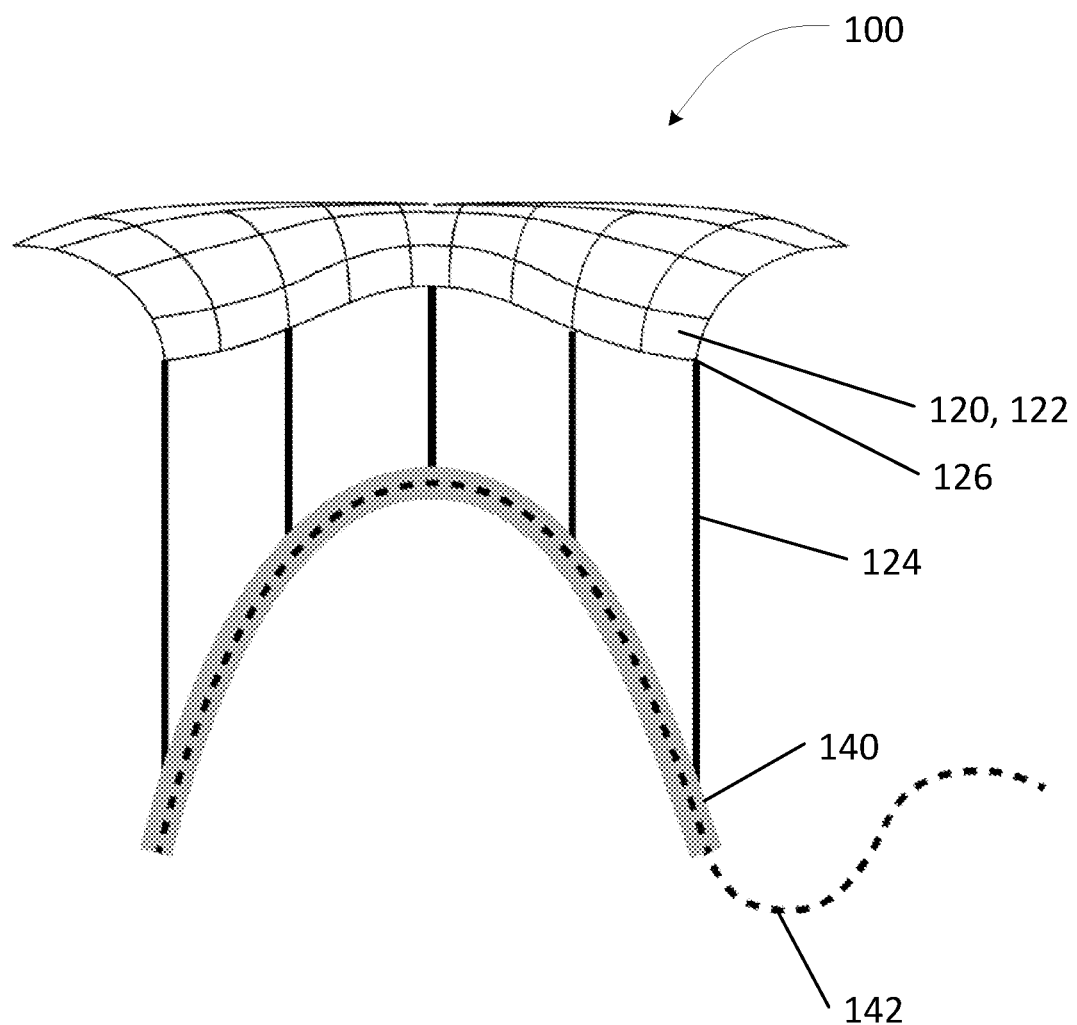
FIG. 4G is a partial posterior illustration of the apparatus shown in FIG. 4A, wherein the tension from a cord is released thereby expanding and lengthening a tube.
Figure 4H:
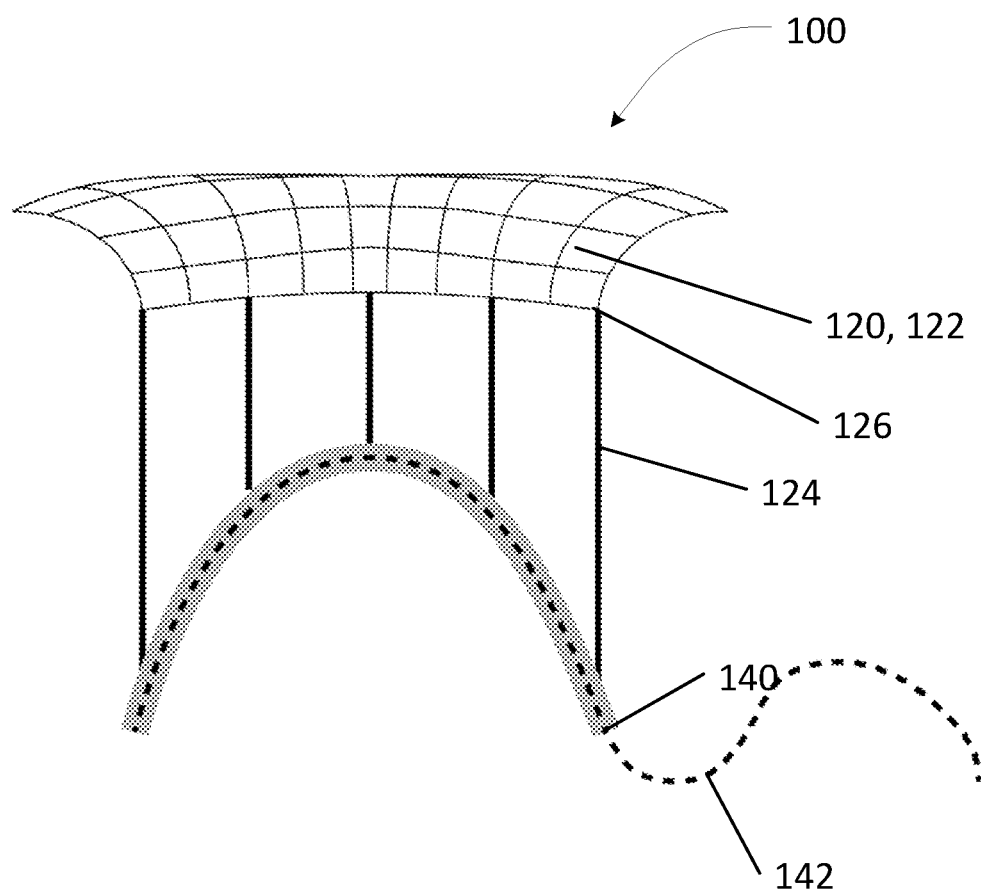
FIG. 4H is a partial posterior illustration of the apparatus shown in FIG. 4A, wherein the cord is tensioned thereby compressing and shortening the tube.

Tubes 140, 150 each comprise an adjustment cord 142, 152 secured to an end of the tube and extending longitudinally through the tube. The length of each cord 142, 152 is sufficient to secure at a first end to the tube, extend through the tube, and traverse the patient's circulatory system from an implant site (e.g. papillary muscle 39) to a femoral vein puncture (i.e. the access site to the patient's circulatory system). In this way, a second end of each cord 142, 152 is accessible external to the patient for delivering a device (e.g. a lock) to each tube 140, 150. Tubes 140, 150 may be lengthened and shortened by externally delivering tension to cords 142, 152. By tensioning cord 142/152, tube 140/150 is compressed and shortened, consequently displacing the vertex of the parabolic or parabolic-like shaped tube away from body 110 and causing corresponding displacement of section 122/132 (FIG. 4H). By releasing tension from cord 142/152, tube 140/150 is expanded and lengthened, consequently displacing the vertex of the parabolic or parabolic-like shaped tube toward body 110 and causing corresponding displacement of section 122/132 (FIG. 4G). Sections 122, 132 are displaced via cords 142, 152 to position members 120, 130 to cover an atrial surface of a mitral leaflet as described elsewhere here. When a desired amount of tension is delivered to cord(s) 142, 152 to position member(s) 120, 130 as desired, a lock 700 (described elsewhere herein) is advanced along cord(s) 142, 152 to abut against an end of tube(s) 140, 150. In a locked configuration and abutting against tube(s) 140, 150, tube(s) 140, 150 is secured in a desired length and member(s) 120, 130 is secured in a desired position covering an atrial surface of the mitral leaflet.

In some embodiments, anterior member 120 and/or posterior member 130 comprises a biocompatible blood-permeable material that permits the passage of blood therethrough. In some embodiments, anterior member 120 and/or posterior member 130 comprises a mesh or a material like a net with spaces in it that permits the passage of blood therethrough. In some embodiments, anterior member 120 and/or posterior member 130 comprises a blood-permeable material made of one or more of polytetrafluoroethylene (PTFE), expanded PTFE, polyethylene, polypropylene, polyethylene terephthalate, an extracellular matrix biomaterial, and a tissue engineered material. In some embodiments, anterior member 120 and/or posterior member 130 comprises a blood-permeable material having tissue ingrowth qualities. Persons skilled in the art will recognize that anterior member 120 and/or posterior member 130 may be made of other blood-permeable and biocompatible materials conventionally used in heart surgery.

In some embodiments, section 122 and/or section 132 comprises a biocompatible material that permits the passage of blood therethrough. In some embodiments, section 122 and/or section 132 comprises a mesh or a material like a net with spaces in it that permits the passage of blood therethrough. In some embodiments, section 122 and/or section 132 comprises a blood-permeable material made of one or more of polytetrafluoroethylene (PTFE), expanded PTFE, polyethylene, polypropylene, polyethylene terephthalate, an extracellular matrix biomaterial, and a tissue engineered material. In some embodiments, section 122 and/or section 132 comprises a blood-permeable material having tissue ingrowth qualities. Persons skilled in the art will recognize that section 122 and/or section 132 may be made of other blood-permeable and biocompatible materials conventionally used in heart surgery.

In some embodiments, cords 124 and/or cords 134 comprise one or more of polytetrafluoroethylene (PTFE), expanded PTFE, polyethylene, polypropylene, polyethylene terephthalate, an extracellular matrix biomaterial, and a tissue engineered material. In some embodiments, cords 124 and/or cords 134 comprise a material having tissue ingrowth qualities. Persons skilled in the art will recognize that cords 124 and/or cords 134 may be made of other biocompatible materials conventionally used in heart surgery.

In some embodiments, tube 140 and/or tube 150 comprises a biocompatible material, such as one or more of polytetrafluoroethylene (PTFE), expanded PTFE, polyethylene, polypropylene, polyethylene terephthalate, an extracellular matrix biomaterial, and a metal alloy including (but not limited to) one or more of nickel and/or titanium and/or Nitinol™. Persons skilled in the art will recognize that tube 140 and/or tube 150 may be made of other biocompatible materials conventionally used in heart surgery. In some embodiments, the material is braided, the braid defining an opening extending longitudinally through the tube for receiving an adjustment cord.

In some embodiments, cord 142 and/or cord 152 comprises one or more of polytetrafluoroethylene (PTFE), expanded PTFE, polyethylene, polypropylene, polyethylene terephthalate, an extracellular matrix biomaterial, and a tissue engineered material. In some embodiments, cord 142 and/or cord 152 comprises a material having tissue ingrowth qualities. Persons skilled in the art will recognize that cord 142 and/or cord 152 may be made of other biocompatible materials conventionally used in heart surgery.

In some embodiments, ring 112 comprises a biocompatible material, such as a biocompatible, memory metal alloy including (but not limited to) nickel and/or titanium and/or Nitinol™. In some embodiments, skirt 114 comprises a biocompatible material, such as one or more of polytetrafluoroethylene (PTFE), expanded PTFE, polyethylene, polypropylene, polyethylene terephthalate, and extracellular matrix biomaterial. In some embodiments, body 110 and/or ring 112 and/or skirt 114 is blood-permeable. In some embodiments, body 110 and/or ring 112 and/or skirt 114 comprises a material having tissue ingrowth qualities. Persons skilled in the art will recognize that body 110 and/or ring 112 and/or skirt 114 may be made of other biocompatible materials conventionally used in heart surgery.

Figure 5C:
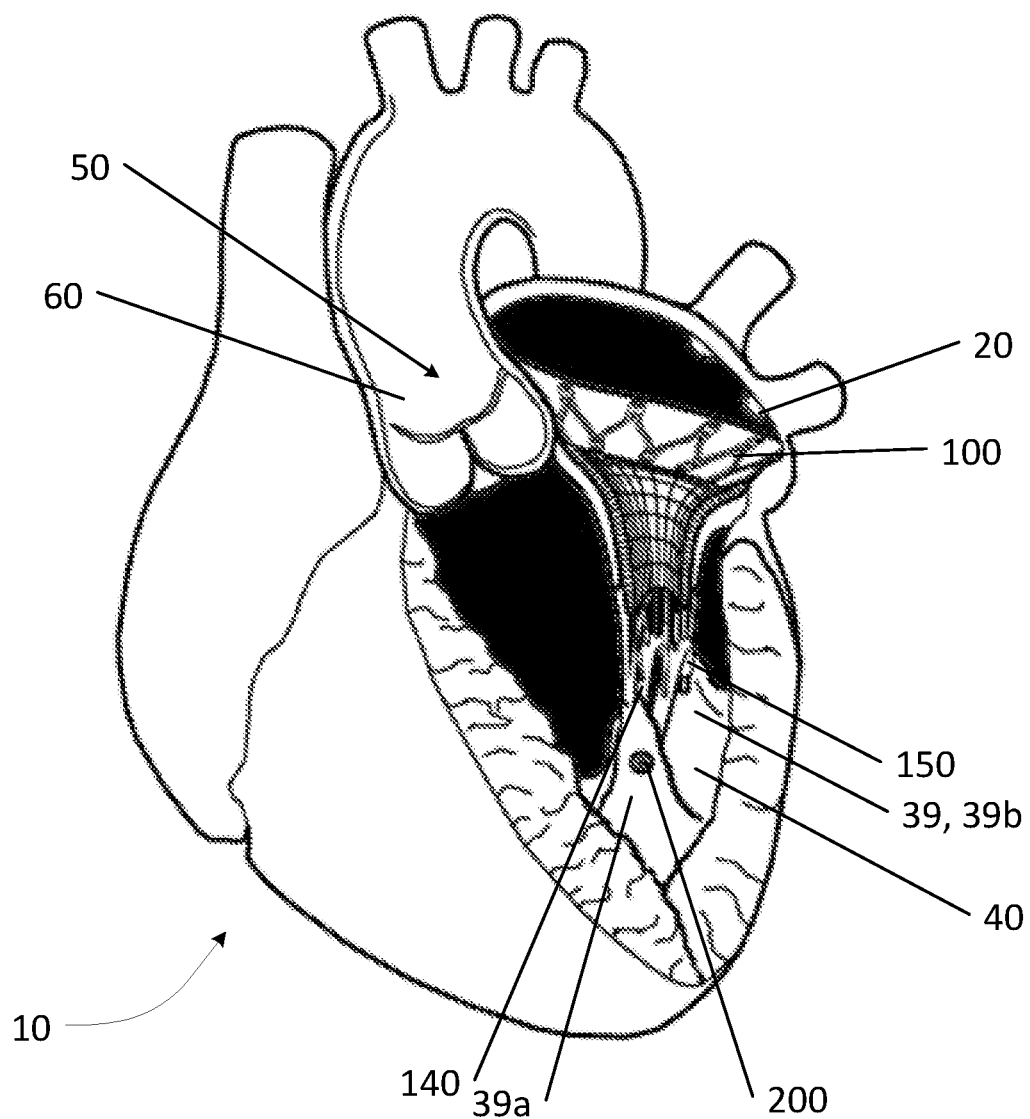
FIG. 5C is a perspective cross-sectional view of the heart shown in FIG. 5A, wherein the apparatus shown in FIG. 4A is advanced into the mitral valve and anchored to the papillary muscles.
Figure 5D:
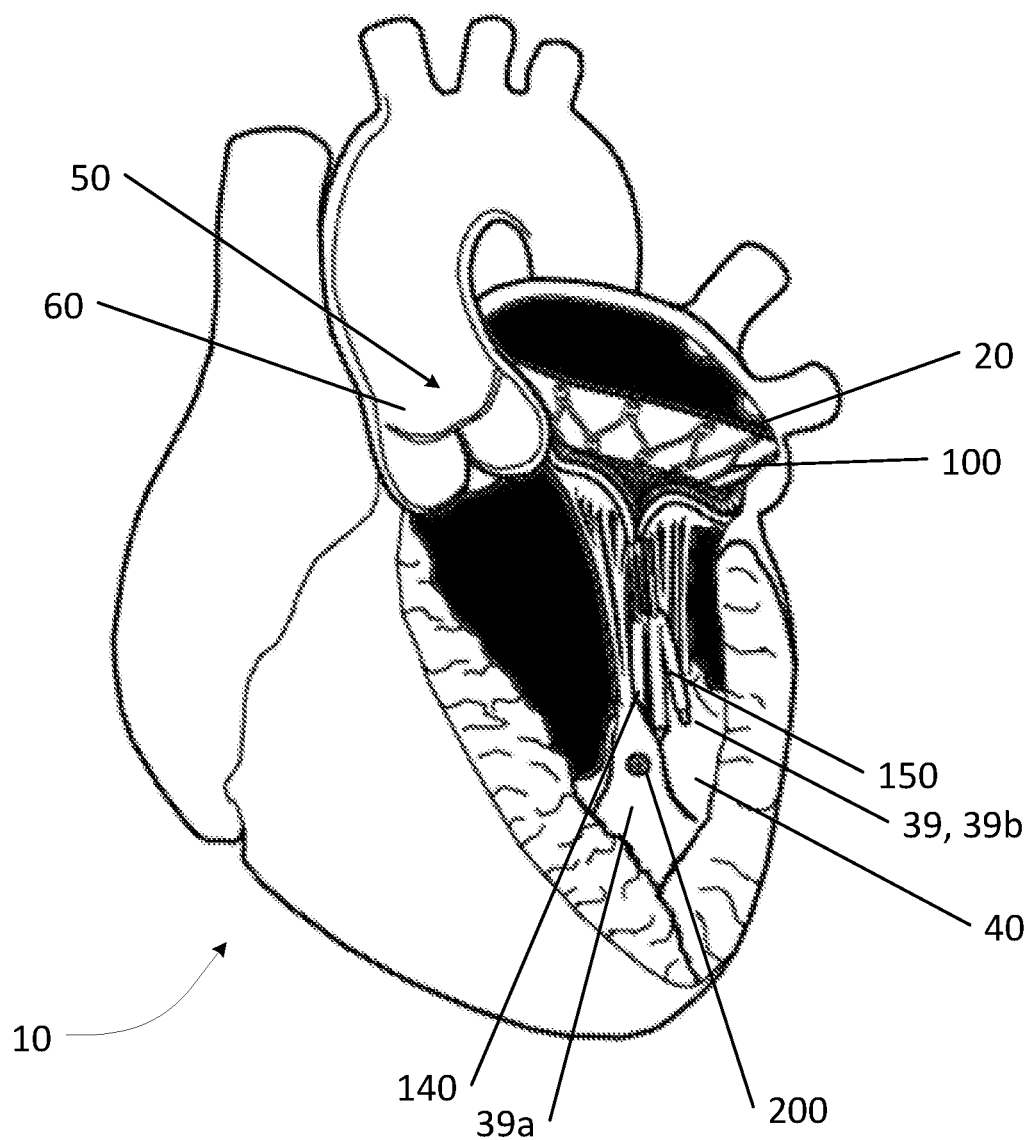
FIG. 5D is a perspective cross-sectional view of the heart and apparatus shown in FIG. 5C, wherein the apparatus is adjusted to fit the mitral valve.
Figure 5E:
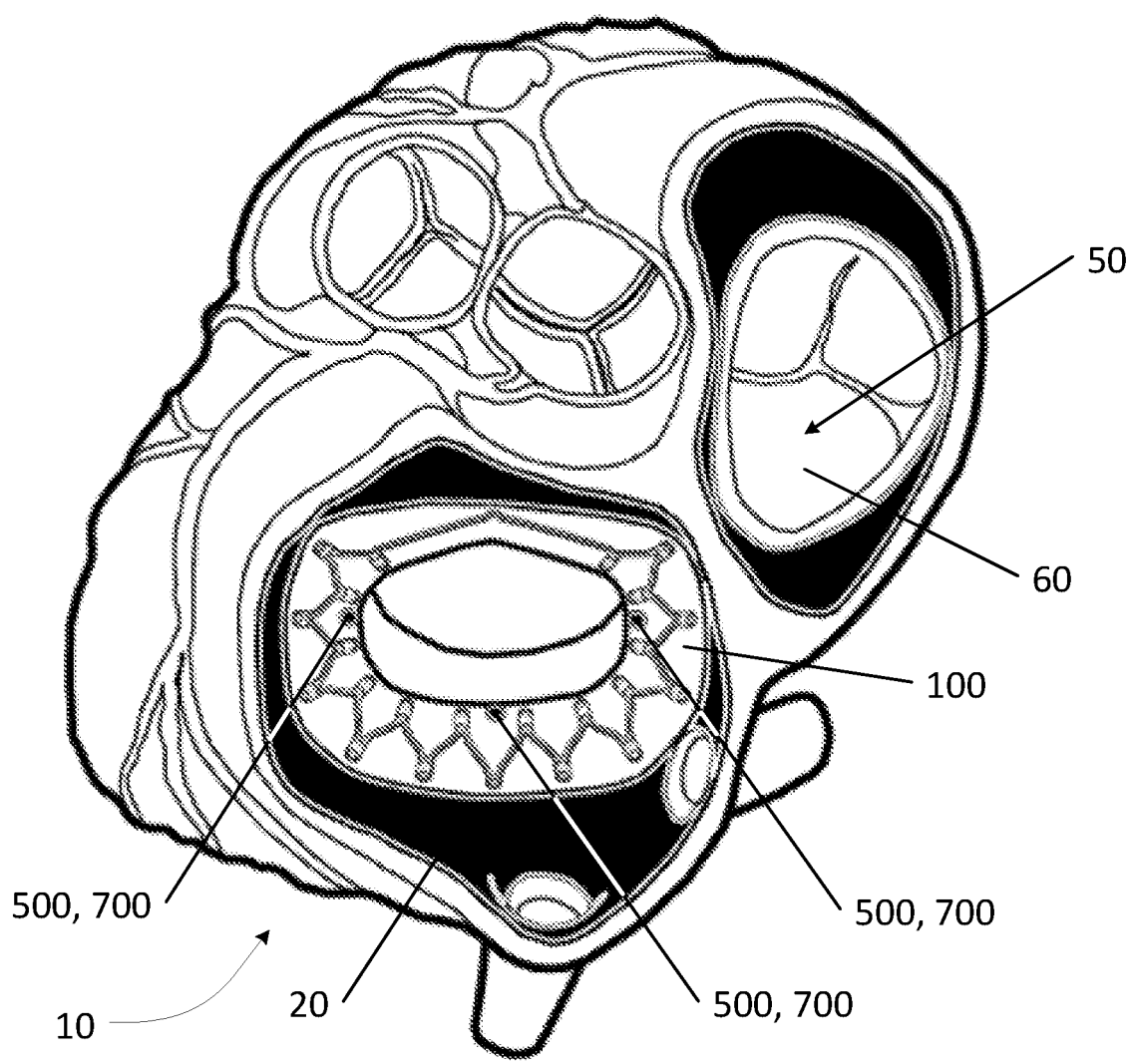
FIG. 5E is a top cross-sectional view of the heart and apparatus shown in FIG. 5C, wherein the apparatus is anchored to the mitral annulus.

FIGS. 5C-5E show apparatus 100 implanted in heart 10, wherein anterior member 120 substantially prevents atrial displacement of anterior mitral leaflet 34 and posterior member 130 substantially prevents atrial displacement of posterior mitral leaflet 36. Anterior member 120 is configured to cover an atrial surface 35 (FIG. 1) of anterior mitral leaflet 34 when apparatus 100 is implanted in the mitral valve. Posterior member 130 is configured to cover an atrial surface 37 (FIG. 1) of posterior mitral leaflet 36 when apparatus 100 is implanted in the mitral valve. In some embodiments, anterior member 120 is sized and/or shaped like anterior mitral leaflet 34. In some embodiments, posterior member 130 is sized and/or shaped like posterior mitral leaflet 36.

Apparatus 100 is delivered and positioned within the heart using anchors (as described elsewhere herein). To implant apparatus 100, a conventional endovascular introducer (not shown) (or other device considered to be within the knowledge of persons skilled in the art of interventional cardiology) is inserted into a patient's circulatory system and advanced using a transcatheter approach conventionally known. In some embodiments, the introducer is advanced using an antegrade transcatheter approach. In some other embodiments, the introducer is advanced using a retrograde transcatheter approach. Where the introducer is introduced into a patient's circulatory system via the femoral vein, the introducer is advanced to the patient's right atrium, through the atrial septum to the left atrium. Conventional Transesophageal Echocardiography (TEE) and/or fluoroscopy techniques may be used to guide the introducer through the patient's circulatory system and position the introducer in the heart.

Once transatrialseptal access of the introducer has been established, a papillary anchor is implanted into each papillary muscle and one or more annular anchors are implanted into the mitral annulus. To implant the papillary anchors, the introducer is advanced across the mitral valve, to the left ventricle of the patient's heart. A papillary anchor is introduced into each of the anterior-lateral papillary muscle and the posterior-medial papillary muscle using a catheter as described elsewhere herein. Conventional Transesophageal Echocardiography (TEE) and/or fluoroscopy techniques may be used to guide the catheter through the patient's circulatory system and position the papillary anchors in the papillary muscle.

To implant the annular anchor(s) into the mitral annulus, the introducer is positioned in the left atrium of the patient's heart. One or more annular anchors are introduced into the mitral annulus using a catheter as described elsewhere herein. Conventional Transesophageal Echocardiography (TEE) and/or fluoroscopy techniques may be used to guide the catheter through the patient's circulatory system and position the annular anchor(s) in the mitral annulus. Persons skilled in the art will recognize that the papillary anchors may be implanted in the papillary muscles before, after, or at approximately the same time that one or more annular anchors are implanted into the mitral annulus.

Example embodiments of an annular anchor are shown in FIGS. 7A-7C and 7D-7F. Anchor 500 (FIGS. 7A-7F) comprises an anchor pin 510, a tether 520 connected to the anchor pin, and a guidewire 530 connected to the tether. The length of the guidewire is sufficient to traverse the patient's circulatory system from mitral annulus 32 to a femoral vein puncture (i.e. the access site to the patient's circulatory system) and to advance apparatus 100 and a conventional transcatheter valve delivery system (e.g. an introducer) over the external end of guidewire 530. In some embodiments, anchor 500 or one or more of the parts thereof comprises a biocompatible material, such as polytetrafluoroethylene (PTFE), expanded PTFE, polyethylene, polypropylene, polyethylene terephthalate, extracellular matrix biomaterial, and a metal alloy including (but not limited to) nickel and/or titanium and/or Nitinol™. In some embodiments, pin 510 comprises a bio-compatible, shape-memory material (e.g. one or more of SMA, smart metal, memory metal, memory alloy, muscle wire, smart alloy, Nitinol™, stainless steel) having a pre-deformed shape such as the shape shown in FIG. 7A or 7D for anchoring anchor 500 in mitral annulus 32. In a deformed shape, pin 510 may be retained in a catheter for advancing anchor 500 to the mitral annulus. Persons skilled in the art will recognize that anchor 500 and the parts thereof may be made of other biocompatible materials conventionally used in heart surgery.

To secure each anchor 500 to mitral annulus 32, an annular anchor catheter is used. Conventional Transesophageal Echocardiography (TEE) and/or fluoroscopy techniques may be used to advance the catheter through a patient's circulatory system to mitral annulus 32 through the introducer. The catheter is deflectable and steerable. An example embodiment of an annular anchor catheter 600 is shown in FIGS. 6A-6G. Catheter 600 comprises a catheter body 610 and a sensor 620 attached to body 610 for detecting contact between catheter 600 and the annular wall of mitral annulus 32. Body 610 houses a needle 630 for piercing the annular wall and implanting anchor 500 into the annular wall tissue. Needle 630 is configured to house pin 510 of anchor 500 and advance anchor 500 through the annular wall.

Figure 6G:
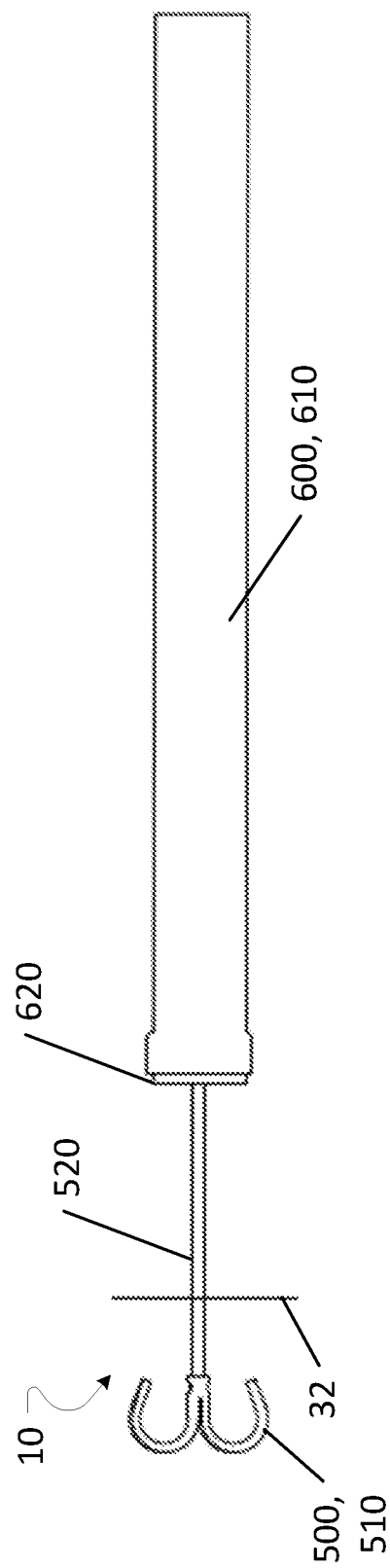
FIG. 6G is a side elevation view of the heart, catheter, and anchor shown in FIG. 6C, wherein the anchor is implanted in the mitral annulus of the heart and the catheter is retracted from the annular wall of the heart.
Figure 7A:
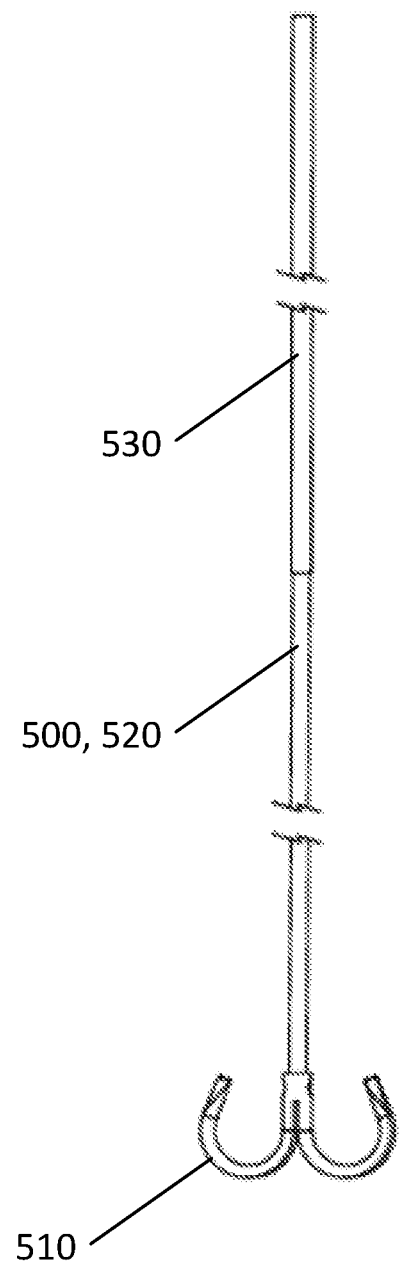
FIG. 7A is a side elevation view of an anchor according to an example embodiment of the present invention.
Figure 7B:
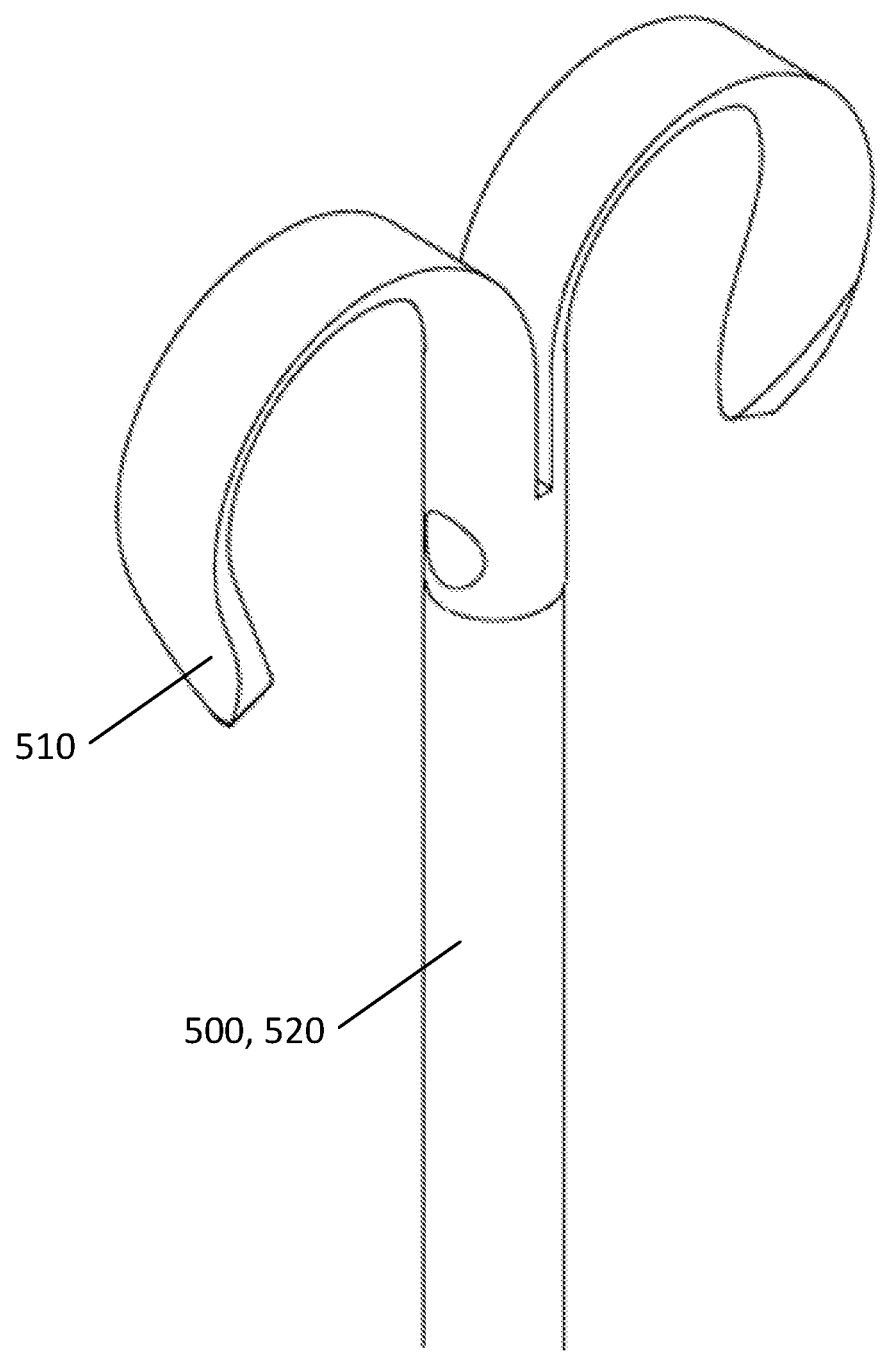
FIG. 7B is a partial perspective view of the anchor shown in FIG. 7A.
Figure 7C:
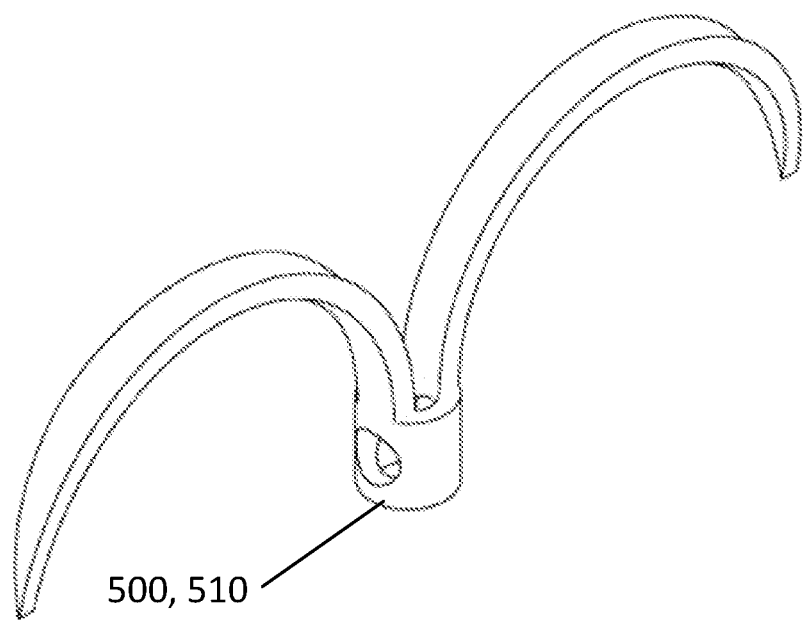
FIG. 7C is a perspective view of an anchor pin of the anchor shown in FIG. 7A.
Figures 8D, 8E:
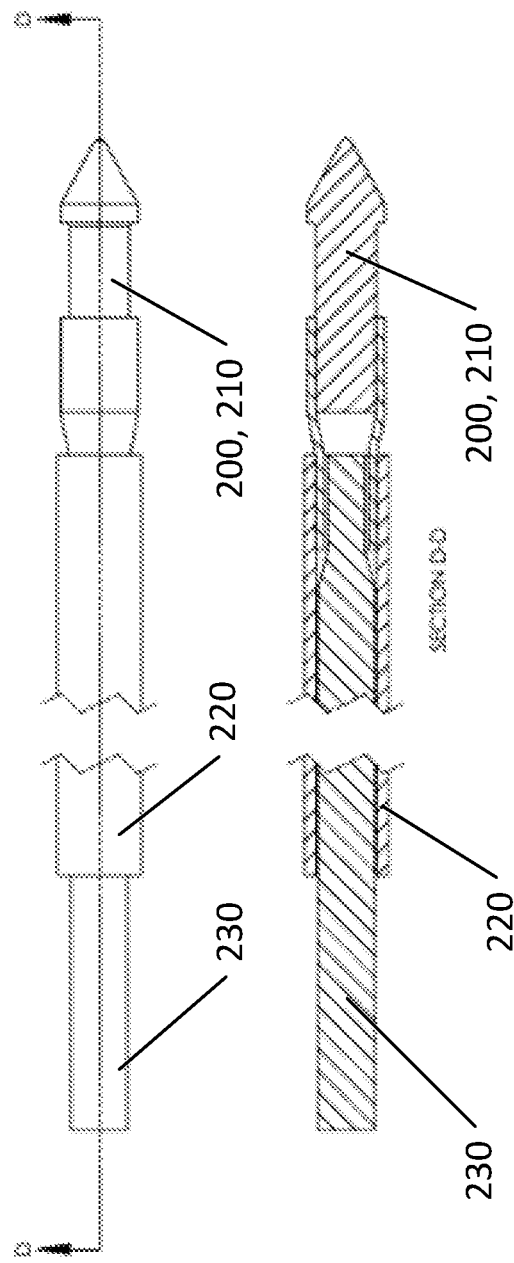
FIG. 8D is a side elevation view of the anchor shown in FIG. 8A.
FIG. 8E is a side cross-sectional view of the anchor shown in FIG. 8D taken along the line D-D.
Figure 9A:
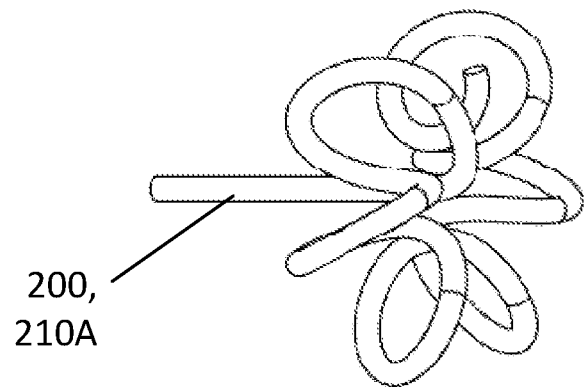
FIG. 9A is a side perspective view of an anchor tip according to an example embodiment of the present invention.
Figure 9B:
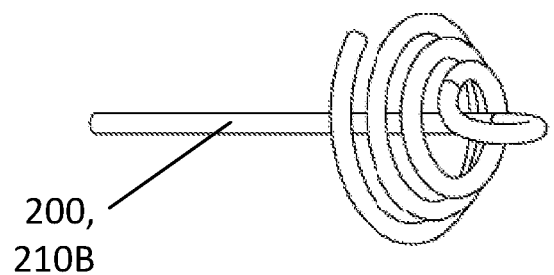
FIG. 9B is a side perspective view of an anchor tip according to an example embodiment of the present invention.
Figure 9C:
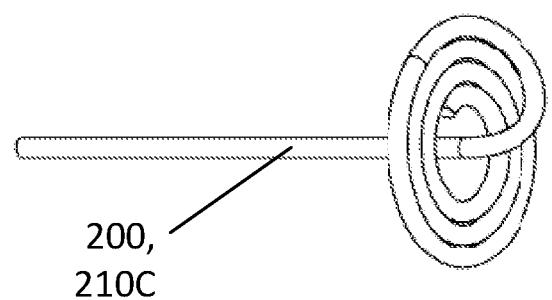
FIG. 9C is a side perspective view of an anchor tip according to an example embodiment of the present invention.
Figure 9D:
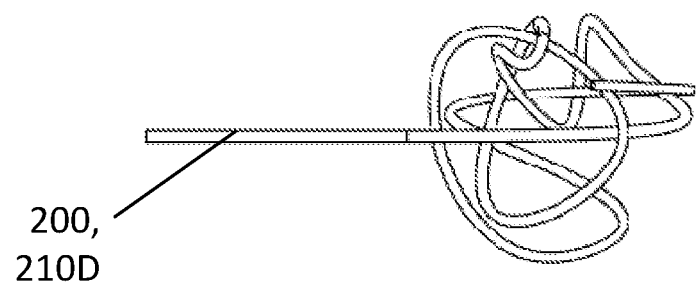
FIG. 9D is a side perspective view of an anchor tip according to an example embodiment of the present invention.

To secure each anchor 500, catheter 600 is advanced to a desired anchor site located at the annular wall of mitral annulus 32. Sensor 620 detects contact between catheter 600 and the anchor site (FIG. 6A). Needle 630 is advanced through the annular wall into the mitral annulus tissue (FIG. 6B). Anchor 500 is advanced through needle 630 (FIG. 6C), with pin 510 resuming a pre-deformed shape as the anchor exits the needle (FIGS. 6D and 6E). In the pre-deformed shape, pin 510 is embedded in the mitral annulus tissue and is not retractable from mitral annulus 32 (FIG. 6F). With anchor 500 secured in mitral annulus 32, needle 630 may be retracted into catheter 600 and catheter 600 may be withdrawn from the patient's circulatory via the introducer (FIG. 6G).

In some embodiments, catheter 600 comprises a controller (not shown) for operating the device extravascularly. When catheter 600 is situated intravascularly, as described elsewhere herein, the controller is located external to the patient's body. In some embodiments the controller includes a handle and means for operating catheter 600 and the parts thereof.

Example embodiments of a papillary anchor are shown in FIGS. 8A-8E and 11A-11E. Anchor 200 comprises an anchor pin 210, a tether 220 connected to the anchor pin, and a guidewire 230 connected to the tether. In the embodiment illustrated in FIGS. 8A-8E, anchor 200 comprises a pair of tethers 220, each tether 220 connected to a guidewire 230. In some embodiments, the anchor comprises one tether connected to a guidewire. The length of each guidewire 230 is sufficient to traverse the patient's circulatory system from the papillary muscle to the femoral vein puncture (i.e. the access site to the patient's circulatory system) and to advance apparatus 100 and a conventional transcatheter valve delivery system (e.g. an introducer) over the external end of guidewire 230. In some embodiments, anchor 200 or one or more of the parts thereof comprises a biocompatible material, such as polytetrafluoroethylene (PTFE), expanded PTFE, polyethylene, polypropylene, polyethylene terephthalate, extracellular matrix biomaterial, and a metal alloy including (but not limited to) nickel and/or titanium and/or Nitinol™. In some embodiments, the pin comprises a biocompatible, shape-memory material (e.g. one or more of SMA, smart metal, memory metal, memory alloy, muscle wire, smart alloy, Nitinol™, stainless steel) that resumes a pre-deformed shape such as one of the shapes of pins 210A, 210B, 210C, and 210D shown in FIG. 9A-9D. Persons skilled in the art will recognize that anchor 500 and the parts thereof may be made of other biocompatible materials conventionally used in heart surgery. Many features and components of anchors 290, 291, 292, and 293 (FIGS. 11A-11E) are similar to features and components of anchor 500, with the same reference numerals being used to indicate similar features and components.

In some embodiments, anchor 200 includes a fastener for securing anchor 200 to papillary muscle 39. Example embodiments of a fastener are shown in FIGS. 10A-10C and 11A-11E. Fastener 250 comprises a body 260 defining an aperture 270. Anchor 200 is advanced through papillary muscle 39 and through aperture 270 of fastener 250. When pin 210 abuts fastener 250, fastener 250 disperses any retracting forces anchor 200 has on the papillary muscle thereby preventing anchor 200 from being retracted back through papillary muscle 39. In some embodiments, fastener 250 comprises a biocompatible material, such as polytetrafluoroethylene (PTFE), expanded PTFE, polyethylene, polypropylene, polyethylene terephthalate, extracellular matrix biomaterial, and a metal alloy including (but not limited to) nickel and/or titanium and/or Nitinol™. Many features and components of fastener 280 (FIGS. 11A-11E) are similar to features and components of fastener 250, with the same reference numerals being used to indicate similar features and components.

To secure each anchor 200 to a papillary muscle, a papillary anchor catheter is used (FIGS. 12A-12H, 13A-13E, 14A-14D, and 18A-18L and 20A-20L). Conventional Transesophageal Echocardiography (TEE) and/or fluoroscopy techniques may be used to advance the catheter through a patient's circulatory system to a papillary muscle through the introducer. The papillary anchor catheter is deflectable and steerable.

An example embodiment of a papillary anchor catheter is shown in FIGS. 12A-12H and 13A-13E. Catheter 300 comprises a body 310 and a detachable receiver 320 removeably attached to body 310 by an arm 330. Body 310, arm 330, and receiver 320 define an opening 340. Opening 340 is configured to receive a transverse dimension of a papillary muscle 39 therein (FIG. 13A-13D). Body 310 is configured to house anchor 200 having pin 210 and advance anchor 200 through the papillary muscle. In some embodiments body 310 comprises a retaining pin 350 for closing opening 340. In a closed configuration shown in FIG. 12A, retaining pin 350 seals opening 340 and catheter 300 may be advanced through the patient's circulatory system and positioned adjacent the papillary muscle with minimal snaring and/or entangling surrounding tissues and/or valve structures. In an open configuration shown in FIGS. 12B-12H, retaining pin 350 is at least partially retracted inside body 310 and opening 340 is exposed for receiving the papillary muscle. To advance and retract retaining pin 350 across opening 340, retaining pin 350 comprises a wire 352 extending through body 310. The length of wire 352 is sufficient to traverse the patient's circulatory system from papillary muscle 39 to a femoral vein puncture (i.e. the access site to the patient's circulatory system) and to operate retaining pin 350 external the patient.

Figure 13A:
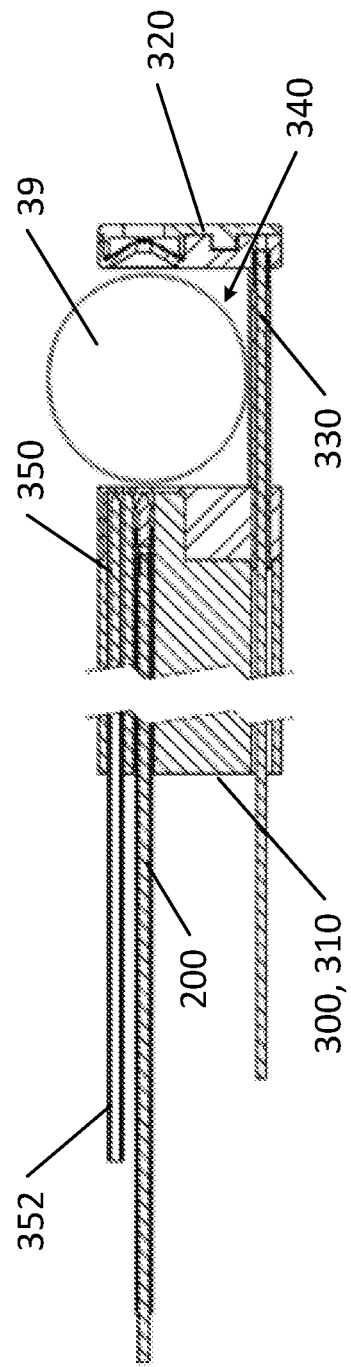
FIG. 13A is a side elevation cross-sectional view of the catheter and anchor shown in FIG. 12A taken along the line A-A, wherein the catheter houses a papillary muscle.
Figure 13B:
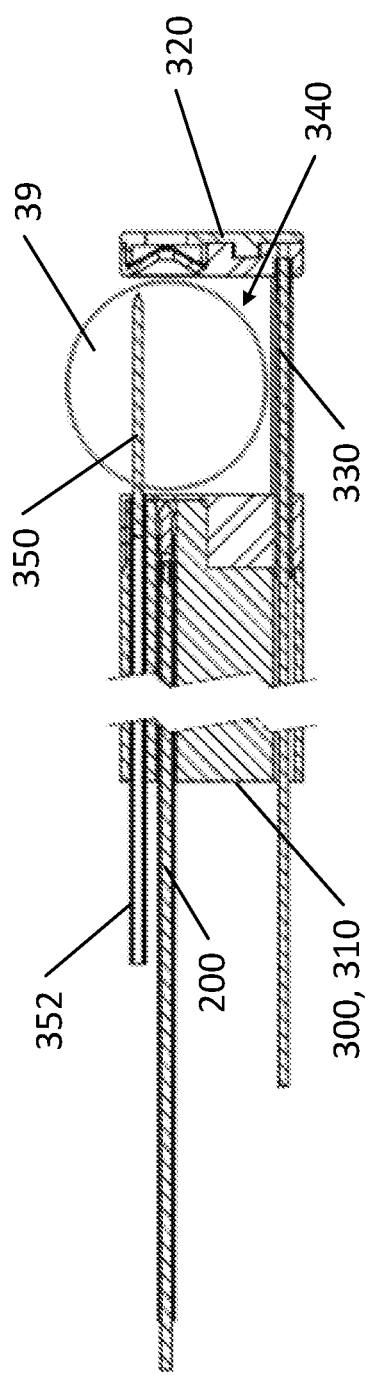
FIG. 13B is a side elevation cross-sectional view of the catheter, anchor, and papillary muscle shown in FIG. 13A, wherein a retaining pin of the catheter is advanced through the papillary muscle.
Figure 13C:
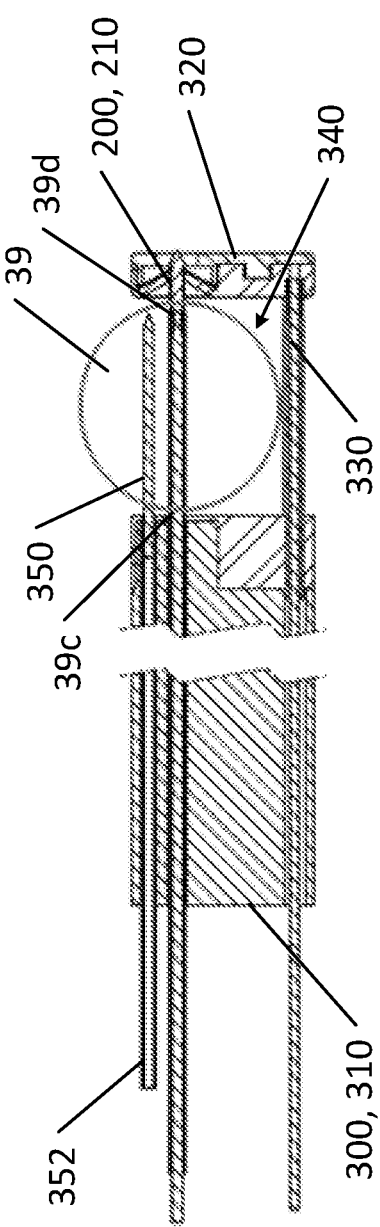
FIG. 13C is a side elevation cross-sectional view of the catheter, anchor, and papillary muscle shown in FIG. 13A, wherein the retaining pin and the anchor are advanced through the papillary muscle.

To secure anchor 200 to a papillary muscle, catheter 300 is advanced in the closed configuration through the patient's circulatory system to the papillary muscle. Adjacent the papillary muscle, retaining pin 350 is retracted into body 310 and catheter 300 (in the open configuration) is advanced to position a transverse dimension of the papillary muscle within opening 340 (FIG. 13A). Retaining pin 350 may be extended (i.e. partially or fully closed) to contact or advance through the papillary muscle thereby stabilizing the muscle while anchor 200 is secured therein (FIG. 13B). Pin 210 of anchor 200 is advanced from body 310, through the papillary muscle, to contact and/or secure to receiver 320 (FIG. 13C). In some embodiments anchor 200 is advanced through a transverse dimension of the papillary muscle from an entrance site 39e of the papillary muscle to an exit site 39f of the papillary muscle. Pin 210 is received by receiver 320 adjacent exit site 39f. In some embodiments, anchor 200 is advanced from entrance site 39e to exit site 39f through the center of the papillary muscle. In some embodiments, anchor 200 is advanced from entrance site 39e to exit site 39f through the papillary muscle in such a way to enhance the grab on the papillary muscle to thereby minimize or avoid anchor 200 from being torn out of the papillary muscle.

In some embodiments, pin 210 is connected to receiver 320 via a threaded screw-like mechanism. In some embodiments, receiver 320 houses fastener 250 for engagement with pin 210 as described elsewhere herein. However, persons skilled in the art will recognize that other conventional means for securing pin 210 to receiver 320 may be used. With pin 210 connected to receiver 320, pin 210 is not retractable through the papillary muscle. Tether 220 extends through the papillary muscle and anchor 200 is thereby secured through the muscle.

Figure 13D:
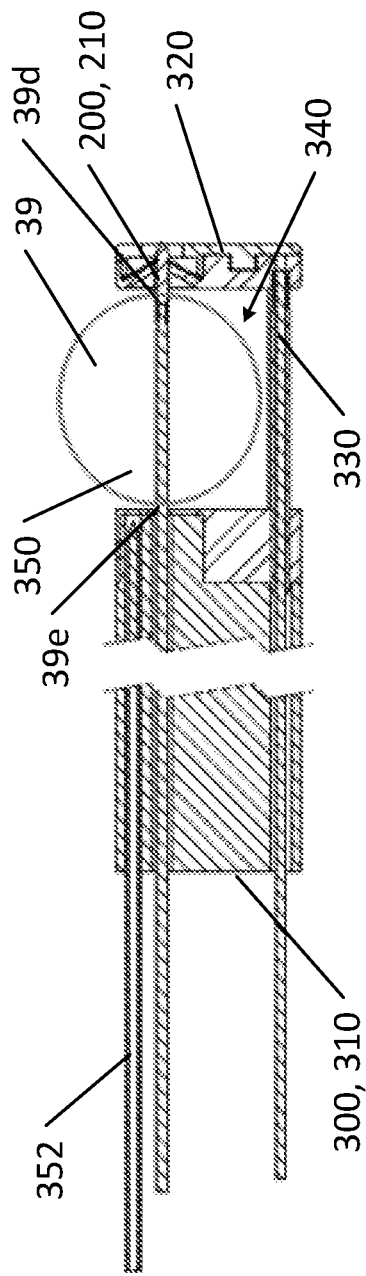
FIG. 13D is a side elevation cross-sectional view of the catheter, anchor, and papillary muscle shown in FIG. 13A, wherein the retaining pin is retracted from the papillary muscle.
Figure 13E:
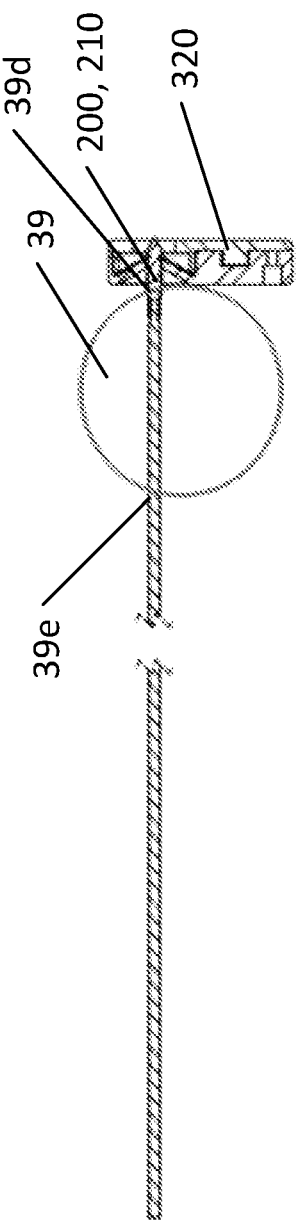
FIG. 13E is a side elevation cross-sectional view of the anchor and papillary muscle shown in FIG. 13A, wherein the catheter is retracted and a receiver is secured to the anchor.

With anchor 200 secured to the papillary muscle, catheter 300 may be withdrawn from the patient's circulatory system by retracting (i.e. unscrewing) arm 330 (and retaining pin 350) into body 310, thereby releasing receiver 320 (FIGS. 13D-13E). Catheter 300 is then withdrawn from the patient via the introducer. To retract arm 330 from receiver 320, arm 330 comprises a wire 332 extending through body 310. The length of wire 332 is sufficient to traverse the patient's circulatory system from papillary muscle 39 to a femoral vein puncture (i.e. the access site to the patient's circulatory system) and to operate arm 330 external the patient. In some embodiments, wire 352 and/or wire 332 are connected to a controller (not shown) external the patient for operating catheter 300 and/or the parts thereof internally. In the embodiment shown in FIGS. 12A-12H, arm 330 comprises a threaded wire 330a that threadedly engages receiver 320 as described elsewhere herein and a pair of support posts 320b on either side of wire 330a that release from receiver 320 when wire 330a is unthreaded from the receiver.

An example embodiment of a papillary anchor catheter is shown in FIGS. 14A-14D. Catheter 400 comprises a body 410 and a deformable arm 420 extending away from body 410. Body 410 is configured to house pin 210 of anchor 200 and advance anchor 200 through the papillary muscle. In some embodiments, body 410 includes a needle 440 for housing pin 210 in body 410 and advancing anchor 200 through the papillary muscle. The length of needle 440 is sufficient to traverse the patient's circulatory system from papillary muscle 39 to a femoral vein puncture (i.e. the access site to the patient's circulatory system) and to operate needle 440 external the patient.

In the illustrated embodiment, arm 420 comprises a plurality of modular pieces 422 arranged linearly and at least one tensioning wire 450 extending through pieces 422. Arm 420 is deformable into a hook-like or deformed configuration for receiving pin 210 when anchor 200 is advanced through the papillary muscle as described elsewhere herein. To deform arm 420, tension is applied to a tensioning wire 450, bringing the edges of adjacent modular pieces 422 together and forming a recess 430 for receiving a papillary muscle. Accordingly, modular pieces 422 are shaped to provide arm 420 with a desired configuration when wire 450 is tensioned. The length of wire 450 is sufficient to traverse the patient's circulatory system from papillary muscle 39 to a femoral vein puncture (i.e. the access site to the patient's circulatory system) and to operate arm 420 external the patient.

Figure 14A:
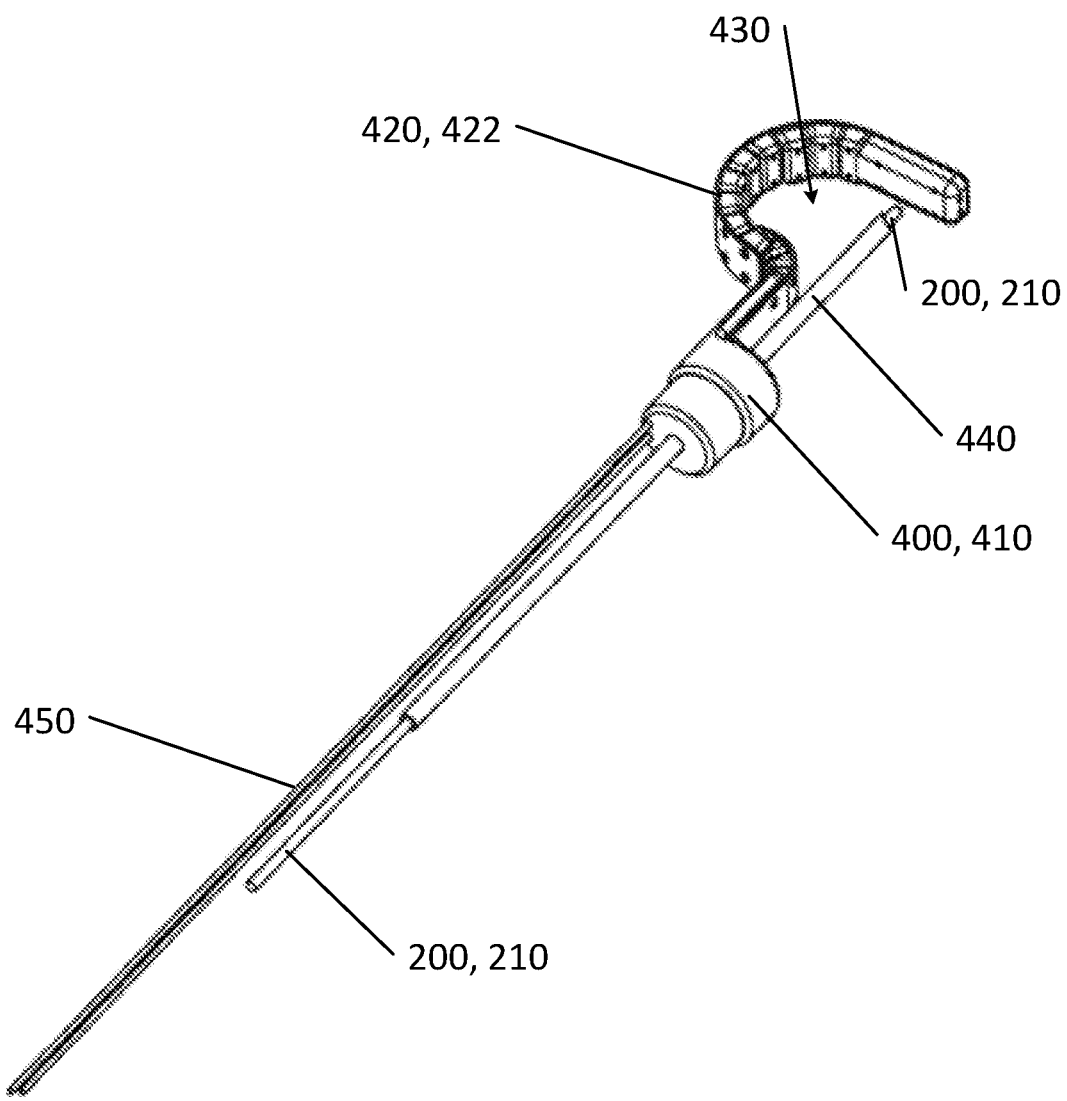
FIG. 14A is a front bottom perspective view of a papillary anchor catheter according to an example embodiment of the present invention in a deformed configuration, wherein an anchor extends therethrough.
Figure 14B:
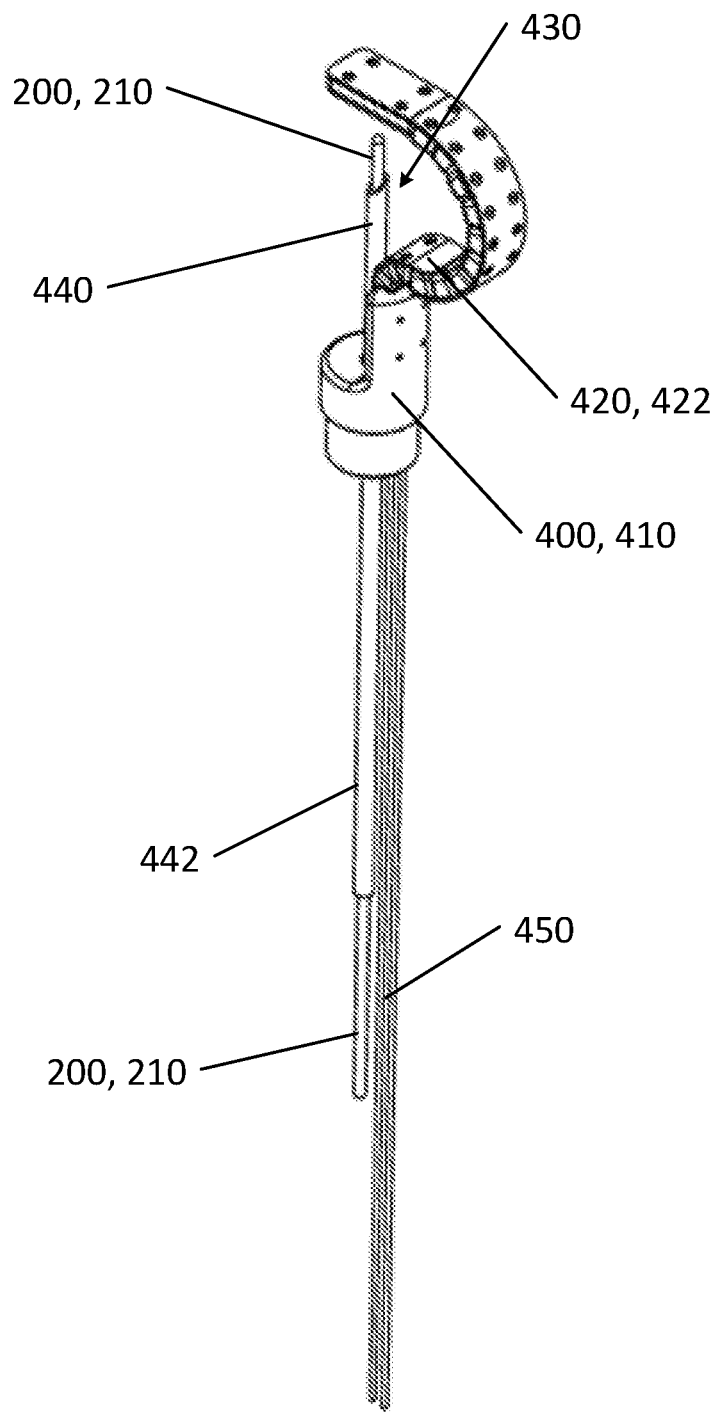
FIG. 14B is a rear top perspective view of the catheter and anchor shown in FIG. 14A.
Figure 14C:
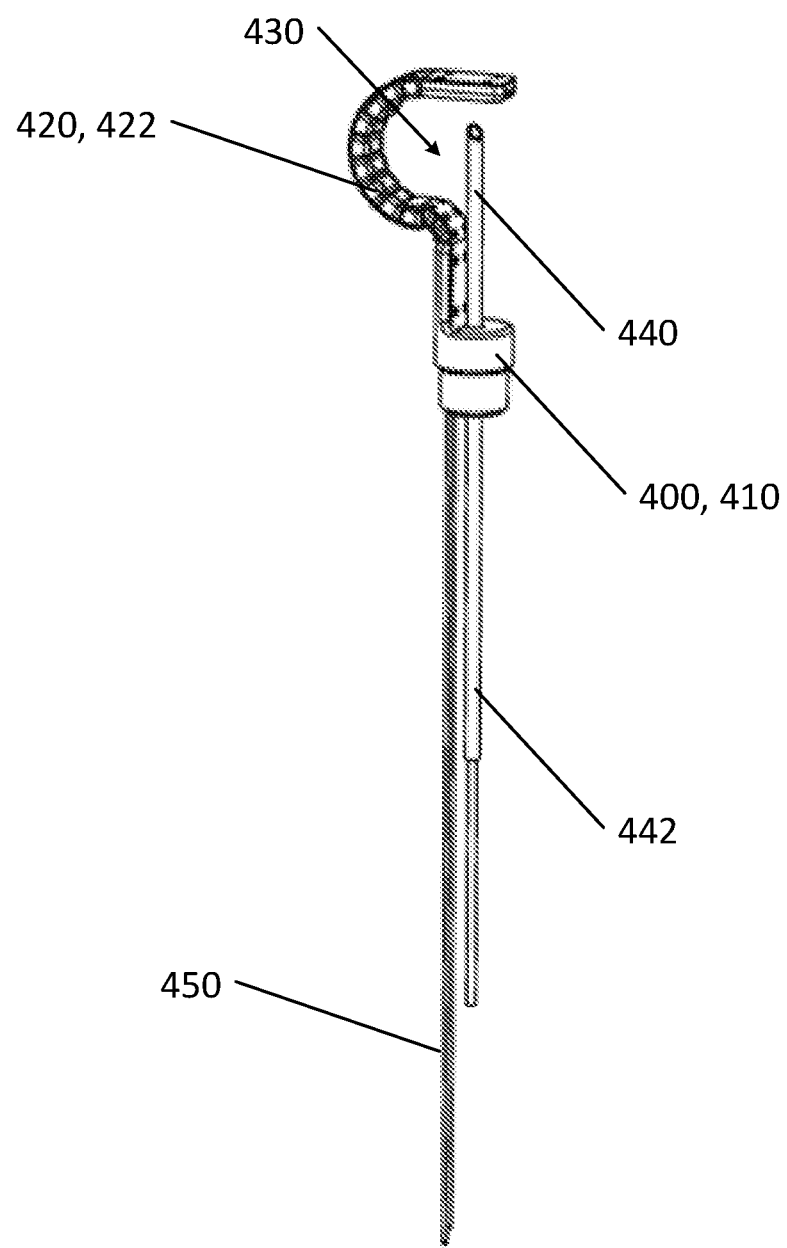
FIG. 14C is a front side perspective view of the catheter shown in FIG. 14A.
Figure 14D:
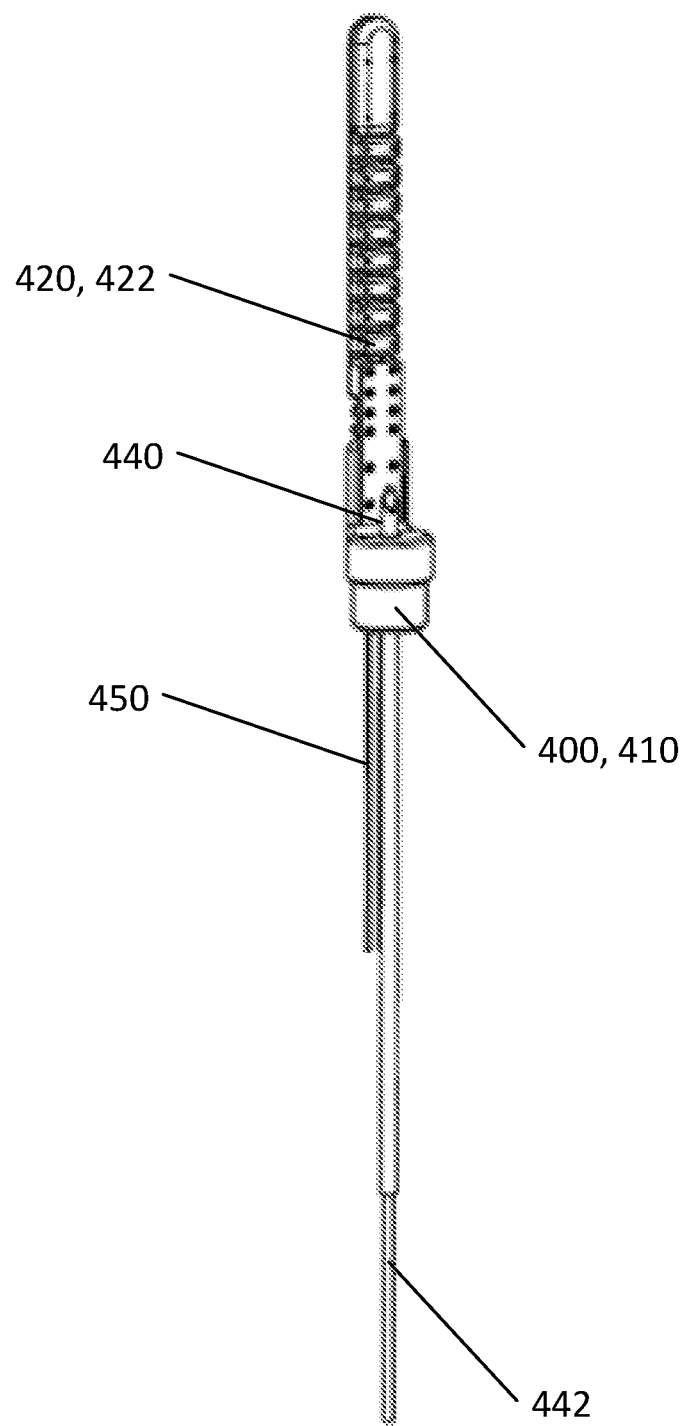
FIG. 14D is a front side perspective view of the catheter shown in FIG. 14A in an extended configuration.

Catheter 400 is shown in a deformed configuration in FIGS. 14A-14C. To return catheter 400 to an extended configuration shown in FIG. 14D, tension is removed from wires 450. In the extended configuration, catheter 400 may be advanced through the patient's circulatory system and positioned adjacent the papillary muscle with minimal snaring and/or entangling surrounding tissues and/or valve structures Persons skilled in the art will recognize that other conventional means for deforming arm 420 may be used.

To secure anchor 200 to a papillary muscle, catheter 400 is advanced in the extended configuration through the patient's circulatory system to the papillary muscle. Tensioning wires 450 are then tensioned to position the papillary muscle within recess 430 of catheter 400. In this deformed configuration, arm 420 at least partially encircles the papillary muscle. Pin 210 of anchor 200 is then advanced from body 410, through the papillary muscle, to contact arm 420. Thus, catheter 400, in the deformed configuration, prevents pin 210 from extending through the papillary muscle and piercing and/or damaging tissue of the left ventricle (i.e. the ventricular wall). In some embodiments anchor 200 is advanced through a transverse dimension of the papillary muscle from an entrance site (not shown) of the papillary muscle to an exit site (not shown) of the papillary muscle. Pin 210 is received by arm 420 adjacent exit site 39d. In some embodiments, anchor 200 is advanced from entrance site 39e to exit site 39d through the center of the papillary muscle. In some embodiments, anchor 200 is advanced from entrance site 39e to exit site 39d through the papillary muscle in such a way to enhance the grab on the papillary muscle to thereby minimize or avoid anchor 200 from being torn out of the papillary muscle.

Once advanced from body 410, pin 210 resumes a pre-deformed shape (e.g. one of the shapes shown in FIGS. 9A-9D and 11A-11E). As such, pin 210 is not retractable through the papillary muscle. Tether 220 extends through the papillary muscle and anchor 200 is thereby secured through the muscle. With anchor 200 secured to the papillary muscle, catheter 400 may be withdrawn from the patient's circulatory system by releasing the tension from wires 450 and withdrawing catheter 400 (in the extended configuration) from the patient via the introducer.

In some embodiments, a guidewire (not shown) may be used to advance catheter 300 and/or catheter 400 to a papillary muscle. In some embodiments, the guidewire comprises a J-shaped tip configured to engage the papillary muscle. The guidewire may be advanced through the patient's circulatory system to the papillary muscle via the introducer. The papillary muscle is positioned about a recess defined by the tip. A balloon (not shown) may be advanced through the introducer, over the guidewire, and inflated to stabilize the guidewire in position and prevent the guidewire from becoming dislodged while catheter 300 and/or catheter 400 is advanced across the guidewire. In this way, catheter 300 and/or catheter 400 may be advanced into a desired position around the papillary muscle.

In some embodiments, catheter 300 comprises a controller (not shown) for operating the device extravascularly. When catheter 300 is situated intravascularly, as described elsewhere herein, the controller is located external to the patient's body. In some embodiments the controller includes a handle and means for operating catheter 300 and the parts thereof.

In some embodiments, catheter 400 comprises a controller (not shown) for operating the device extravascularly. When catheter 400 is situated intravascularly, as described elsewhere herein, the controller is located external to the patient's body. In some embodiments the controller includes a handle and means for operating catheter 400 and the parts thereof.

In some embodiments, catheter 300 and/or the parts thereof comprise a sterilized or sterilisable material. In some embodiments, catheter 300 and/or the parts thereof comprise one or more of medical grade plastic, thermal plastic, stainless steel, metal, a metal alloy (e.g. Nitinol™ or another nickel/titanium alloy), and titanium. Persons skilled in the art will recognize that catheter 300 and/or the parts thereof may be made of any sterilized or sterilisable material conventionally used to manufacture tools used in heart surgery.

In some embodiments, catheter 400 and/or the parts thereof comprise a sterilized or sterilisable material. In some embodiments, catheter 400 and/or the parts thereof comprise one or more of medical grade plastic, thermal plastic, stainless steel, metal, a metal alloy (e.g. Nitinol™ or another nickel/titanium alloy), and titanium. Persons skilled in the art will recognize that catheter 400 and/or the parts thereof may be made of any sterilized or sterilisable material conventionally used to manufacture tools used in heart surgery.

Figure 15A:
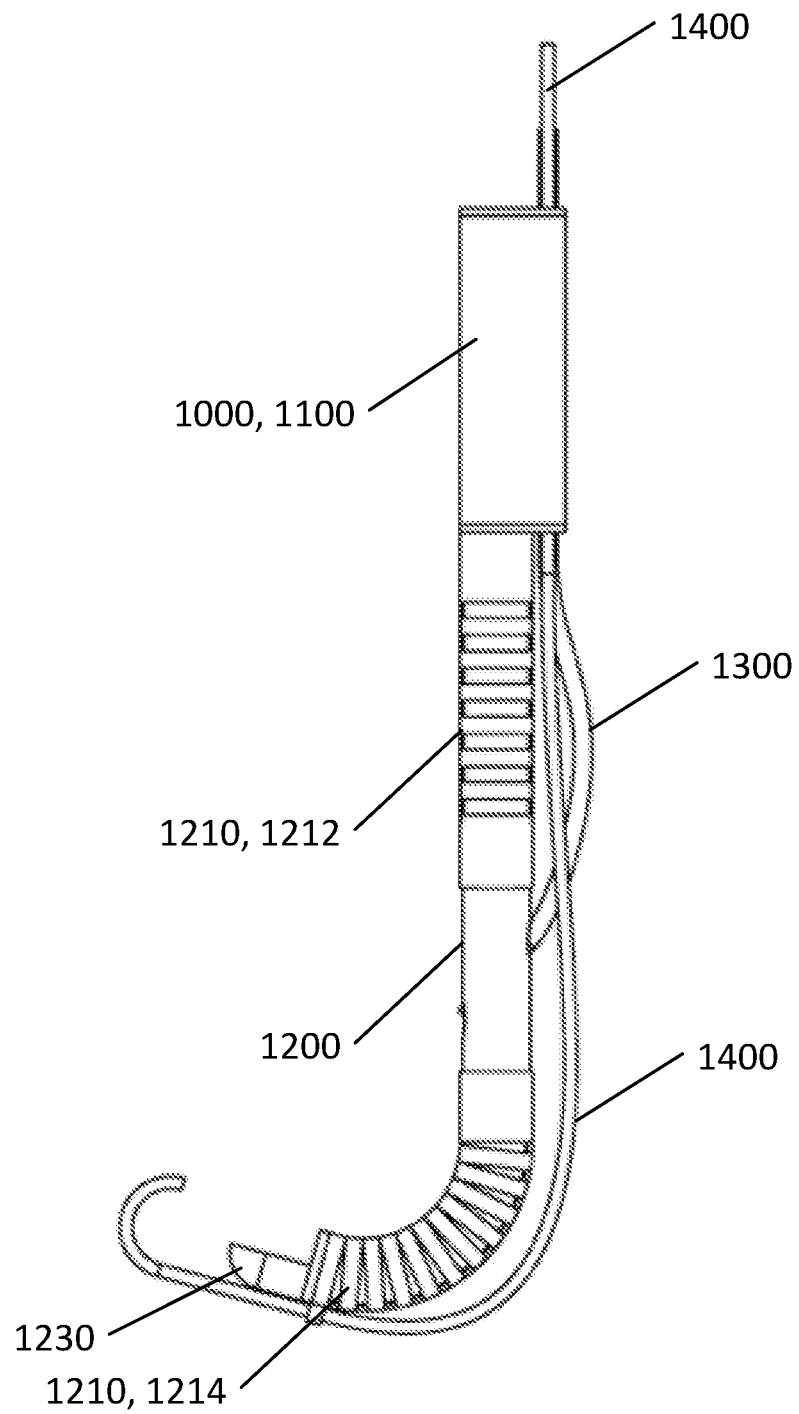
FIG. 15A is a side elevation view of a papillary anchor catheter according to an example embodiment of the present invention in a deformed configuration.
Figure 15B:
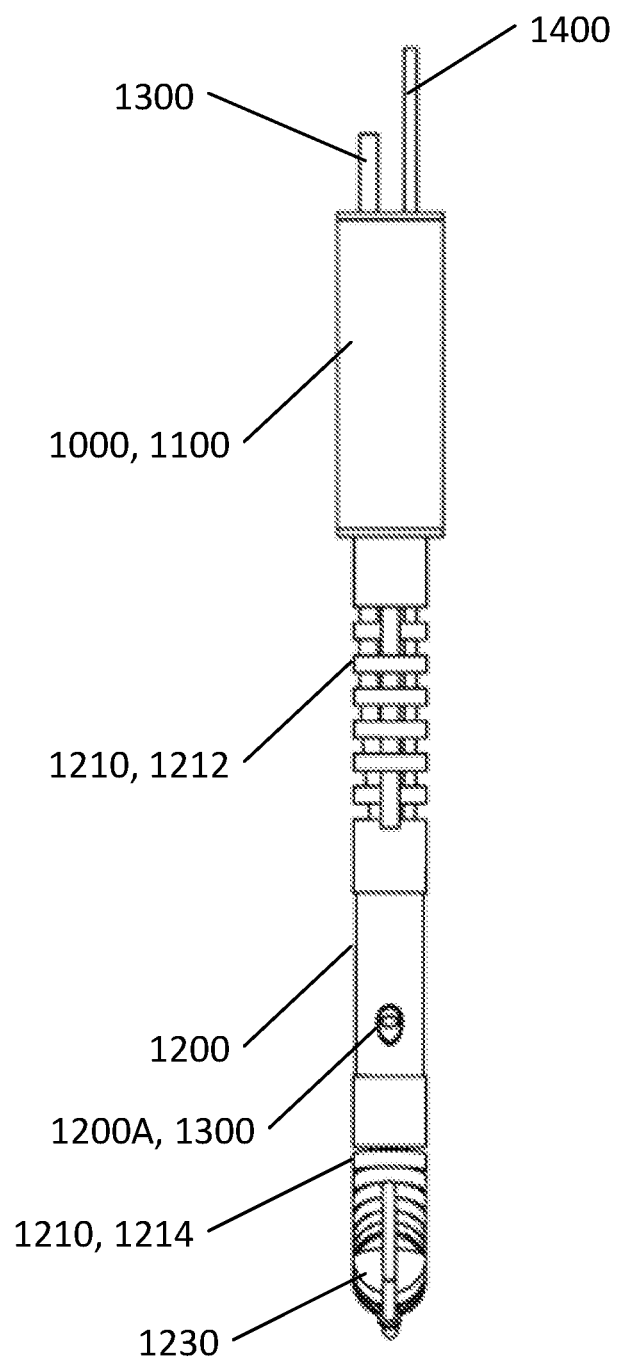
FIG. 15B is a front elevation view of the catheter shown in FIG. 15A in the deformed configuration.
Figure 15C:
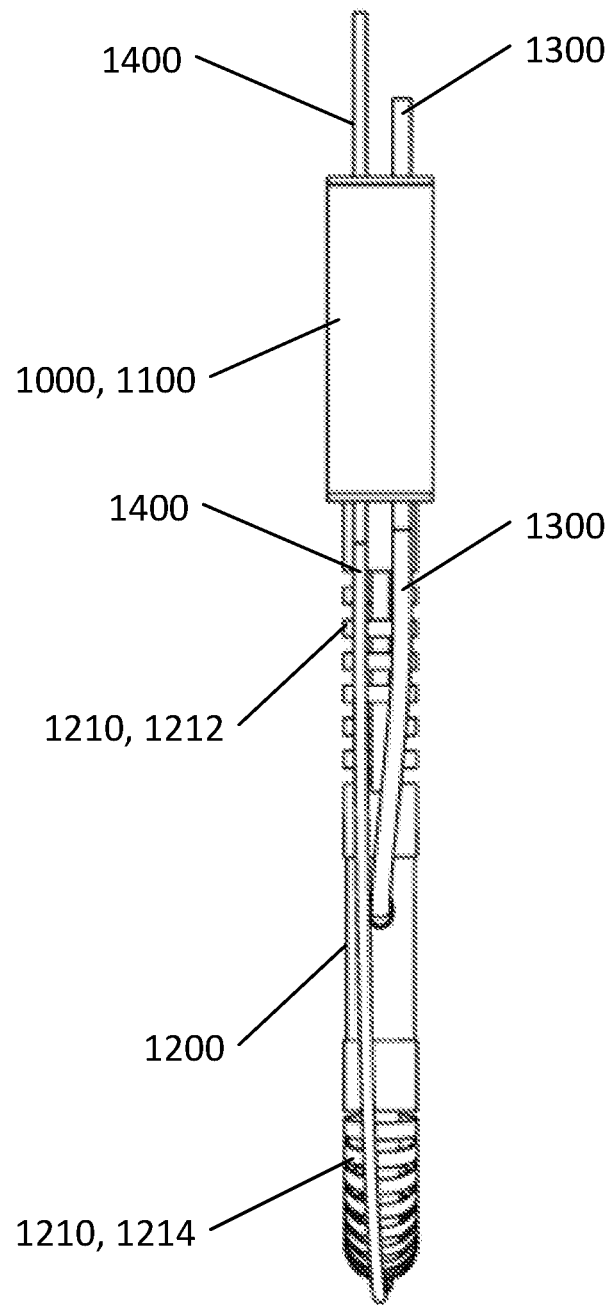
FIG. 15C is a rear elevation view of the catheter shown in FIG. 15A in the deformed configuration.
Figure 15D:
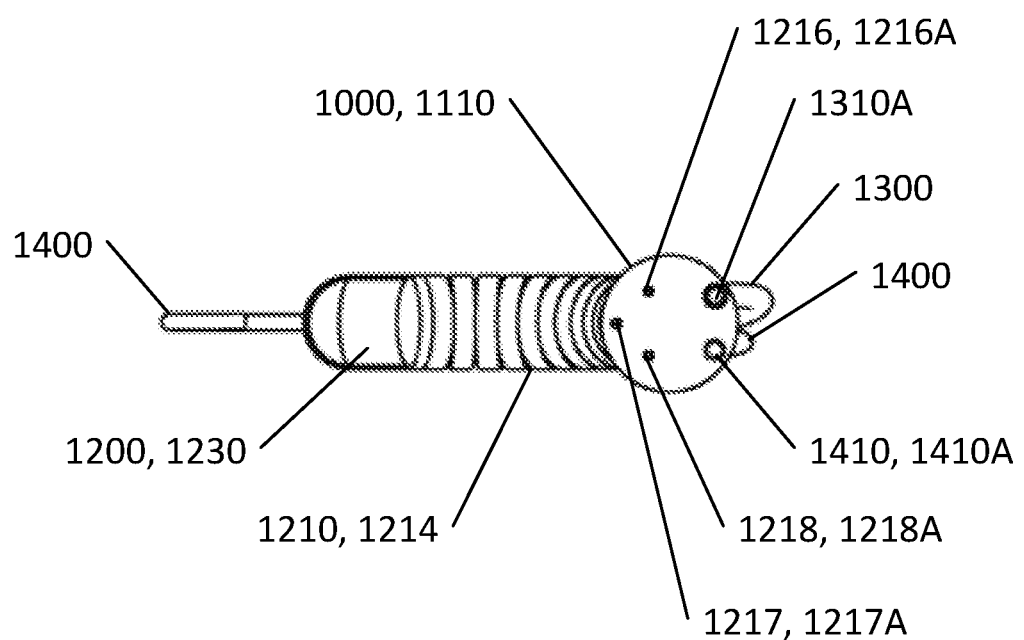
FIG. 15D is a top view of the catheter shown in FIG. 15A in the deformed configuration.
Figure 15E:
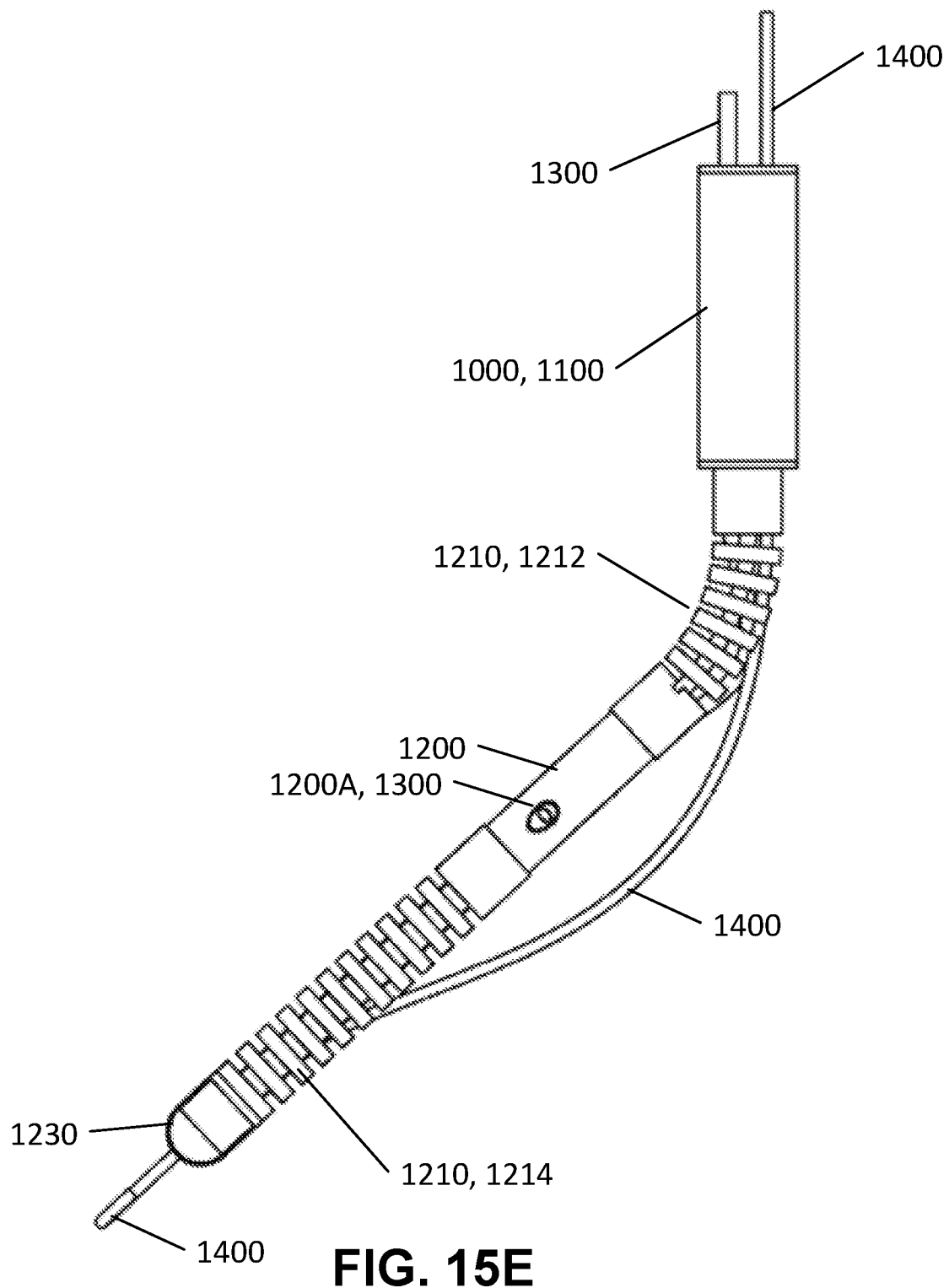
FIG. 15E is a front elevation view of the catheter shown in FIG. 15A in a deflected configuration.
Figure 15F:
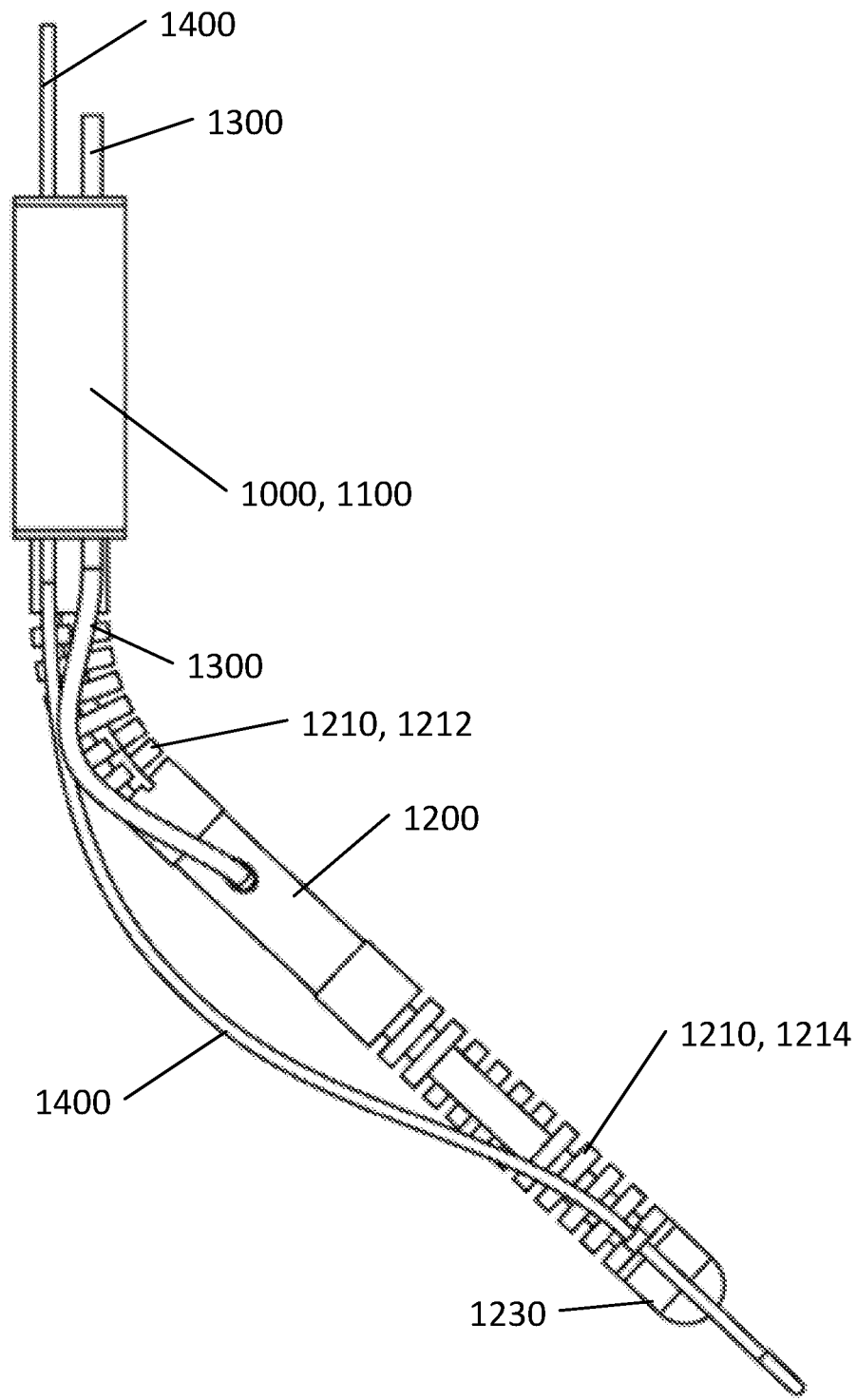
FIG. 15F is a rear elevation view of the catheter shown in FIG. 15A in the deflected configuration.
Figure 15G:
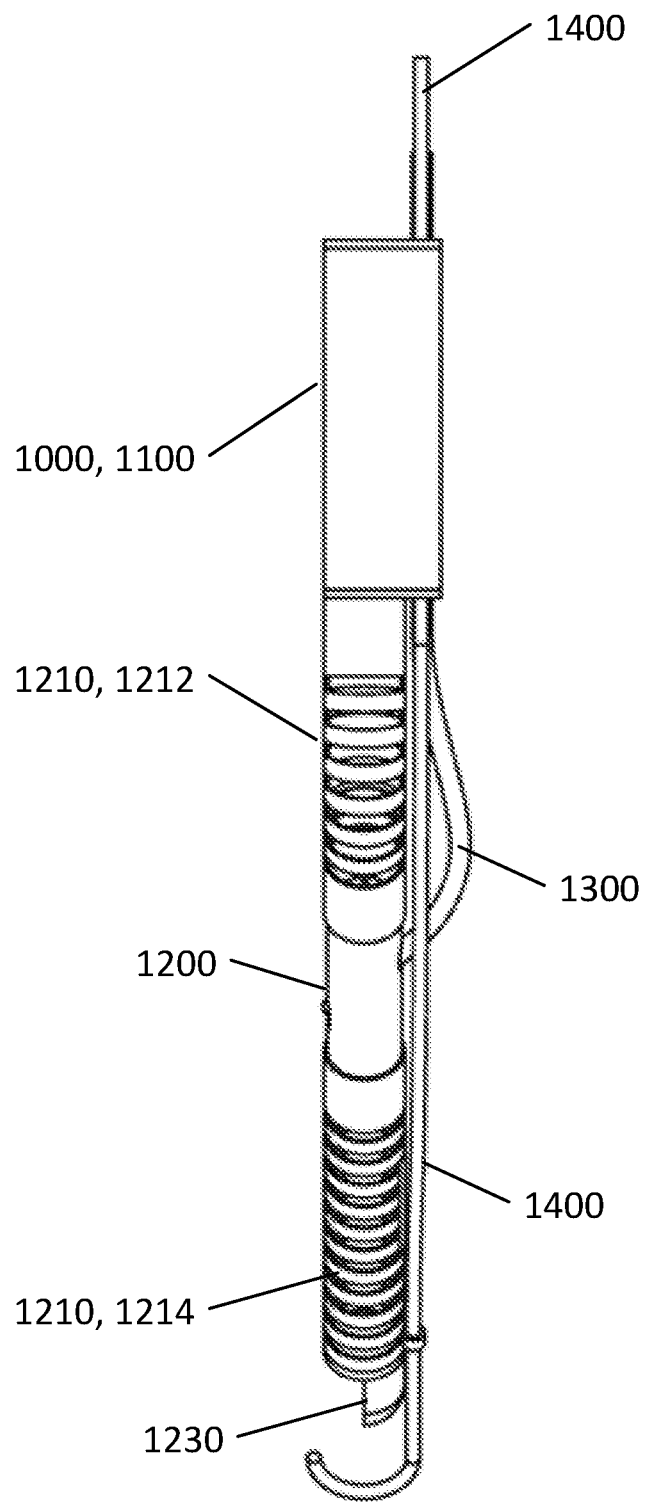
FIG. 15G is a side elevation view of the catheter shown in FIG. 15A in the deflected configuration.
Figure 15H:
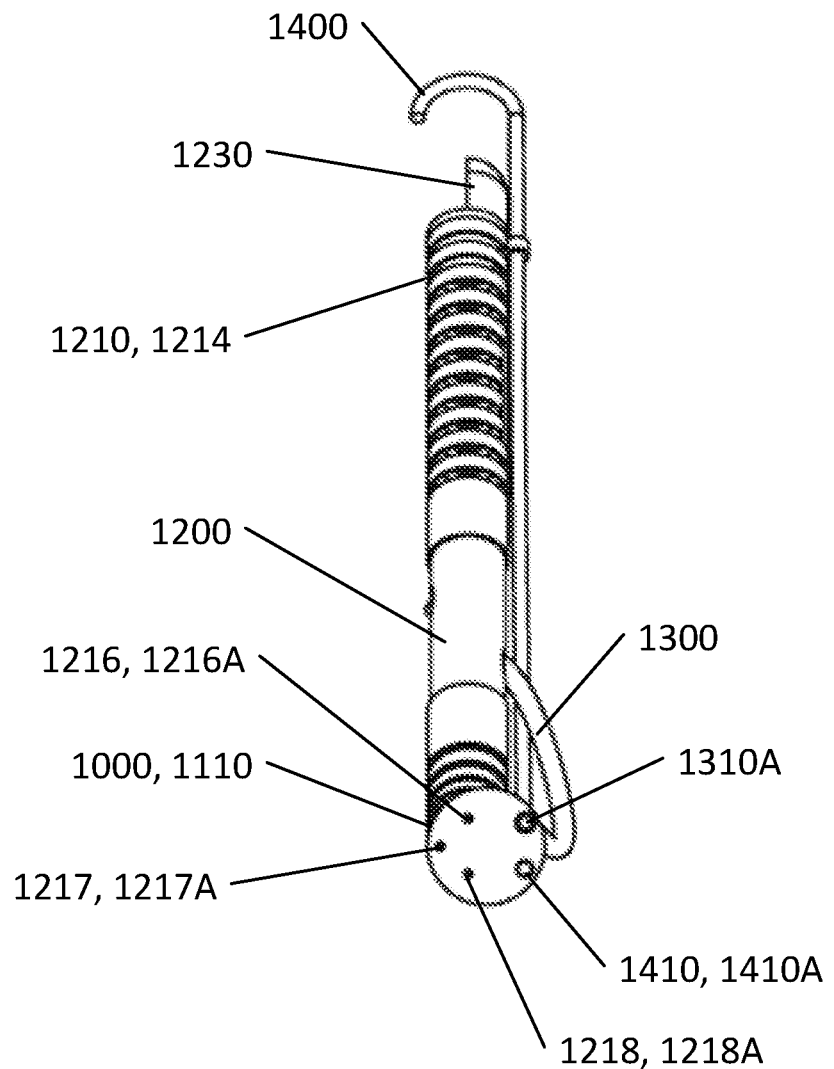
FIG. 15H is a top view of the catheter shown in FIG. 15A in the deflected configuration.
Figure 15I:
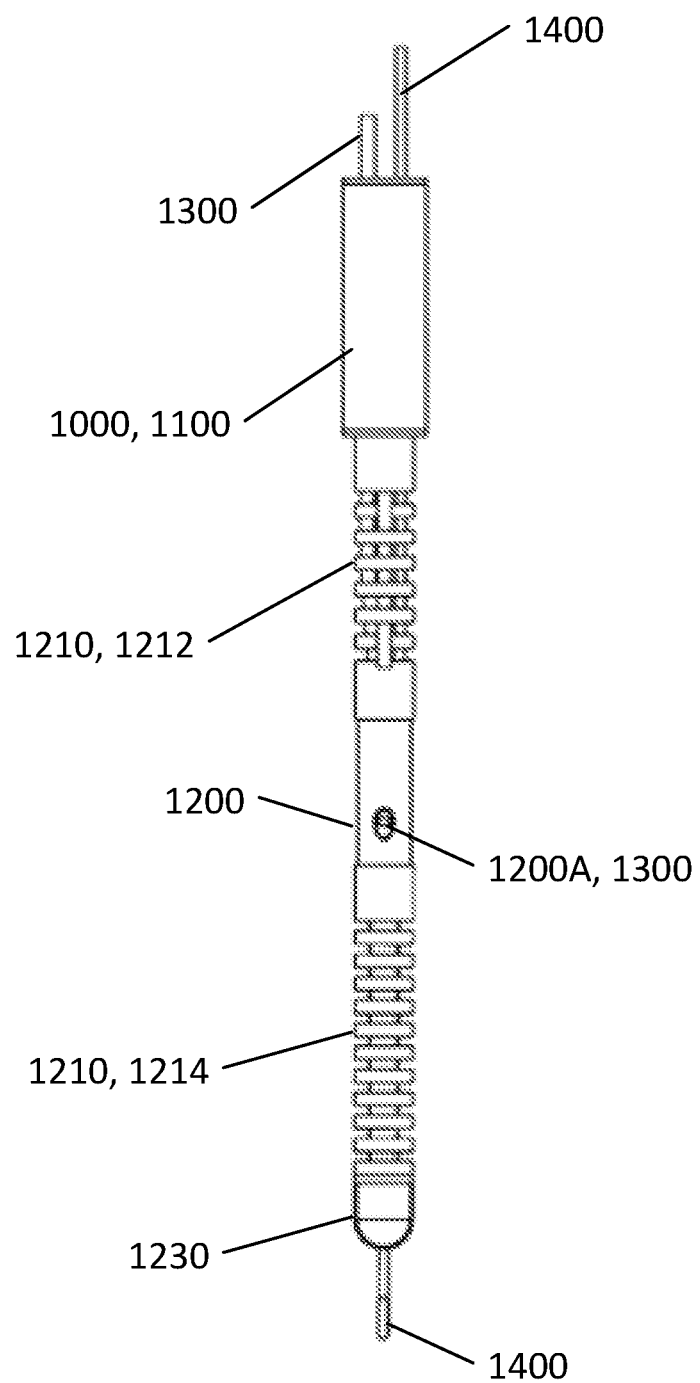
FIG. 15I is a front elevation view of the catheter shown in FIG. 15A in an extended configuration.
Figure 15L:
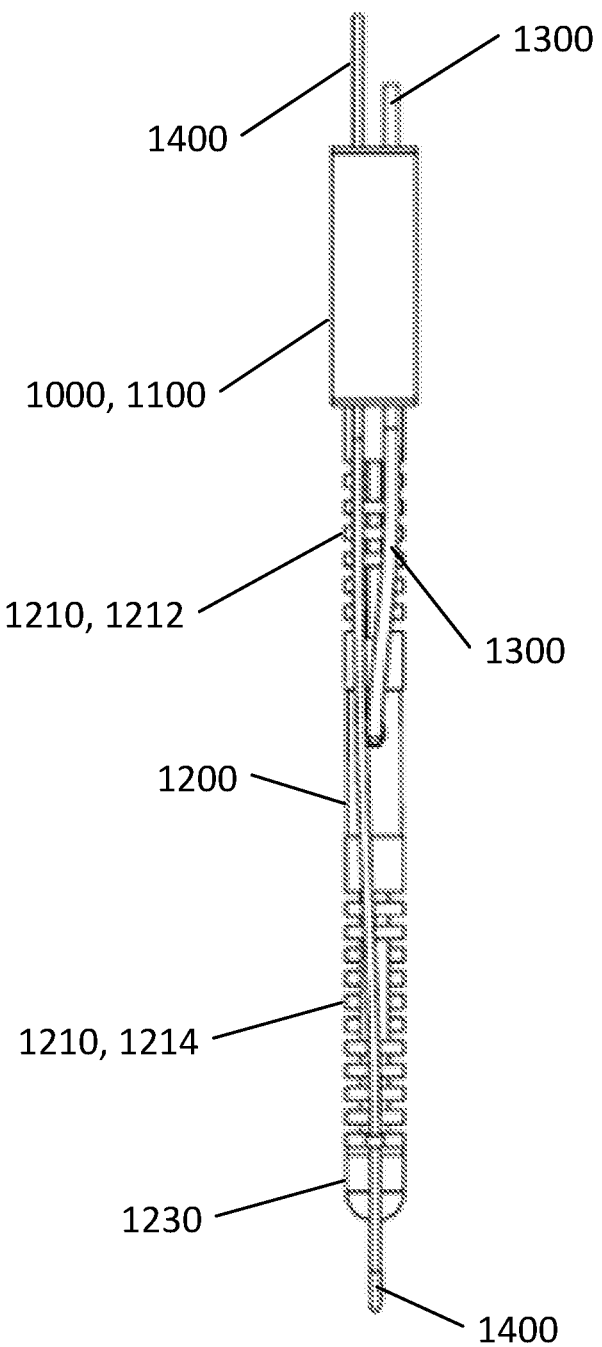
FIG. 15L is a rear elevation view of the catheter shown in FIG. 15A in the extended configuration.
Figure 17A:
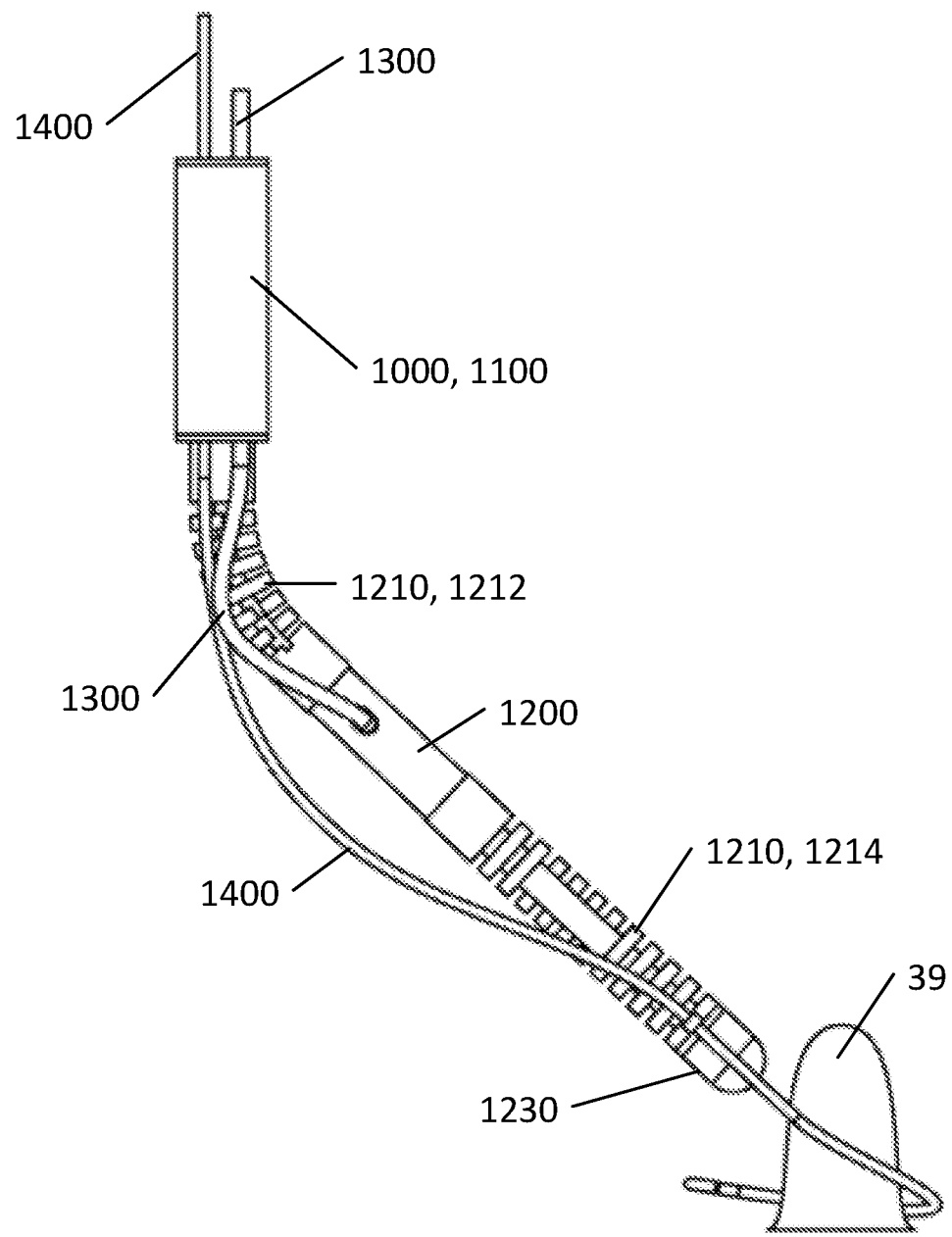
FIG. 17A is a rear elevation view of the papillary catheter shown in FIG. 15A in a deflected configuration extending a guidewire around a papillary muscle.
Figure 17B:
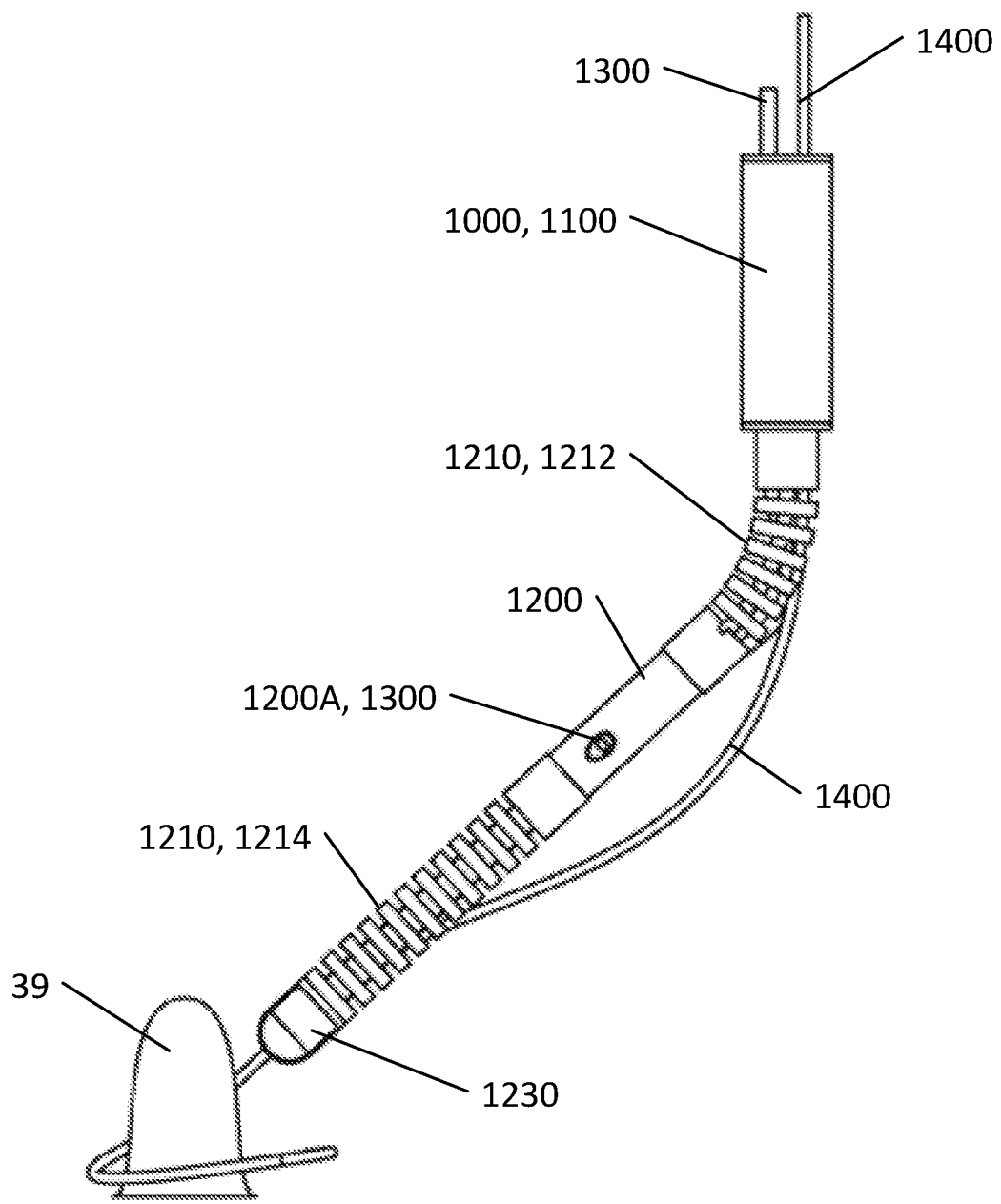
FIG. 17B is a front elevation view of the catheter and papillary muscle shown in FIG. 17A.
Figure 17C:
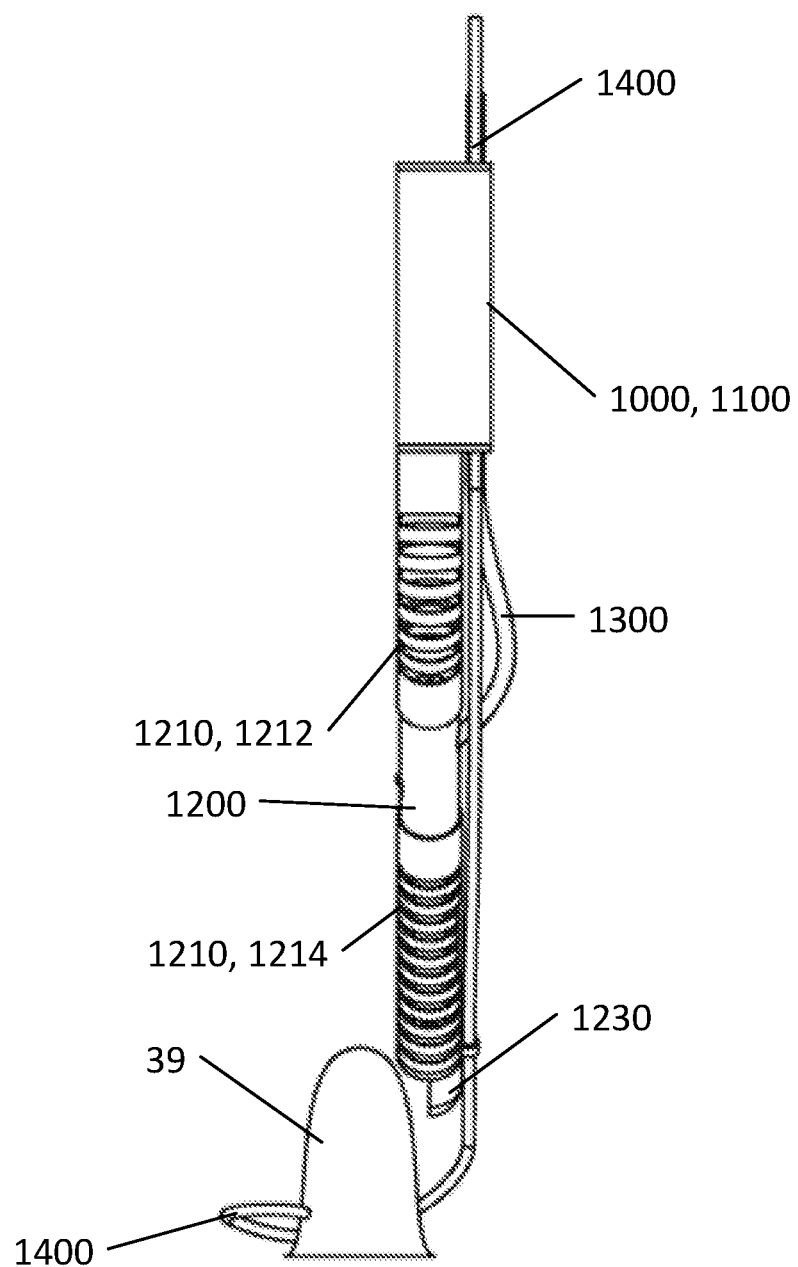
FIG. 17C is a side elevation view of the catheter and papillary muscle shown in FIG. 17A.
Figure 17D:
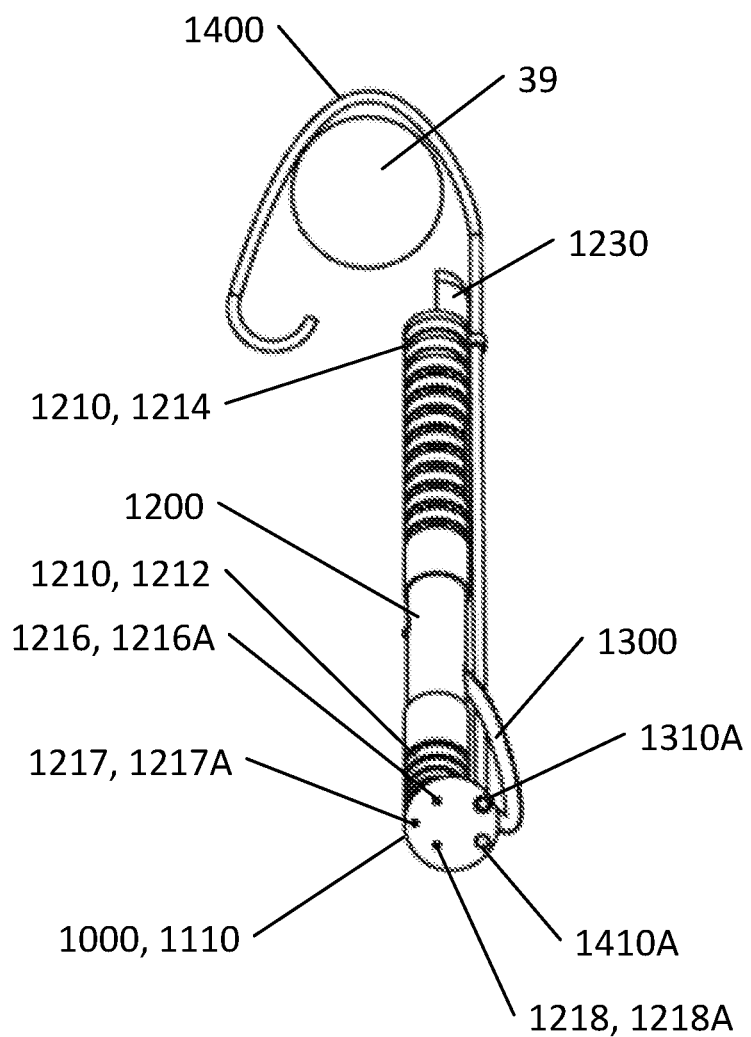
FIG. 17D is a top view of the catheter and papillary muscle shown in FIG. 17A.
Figure 17E:
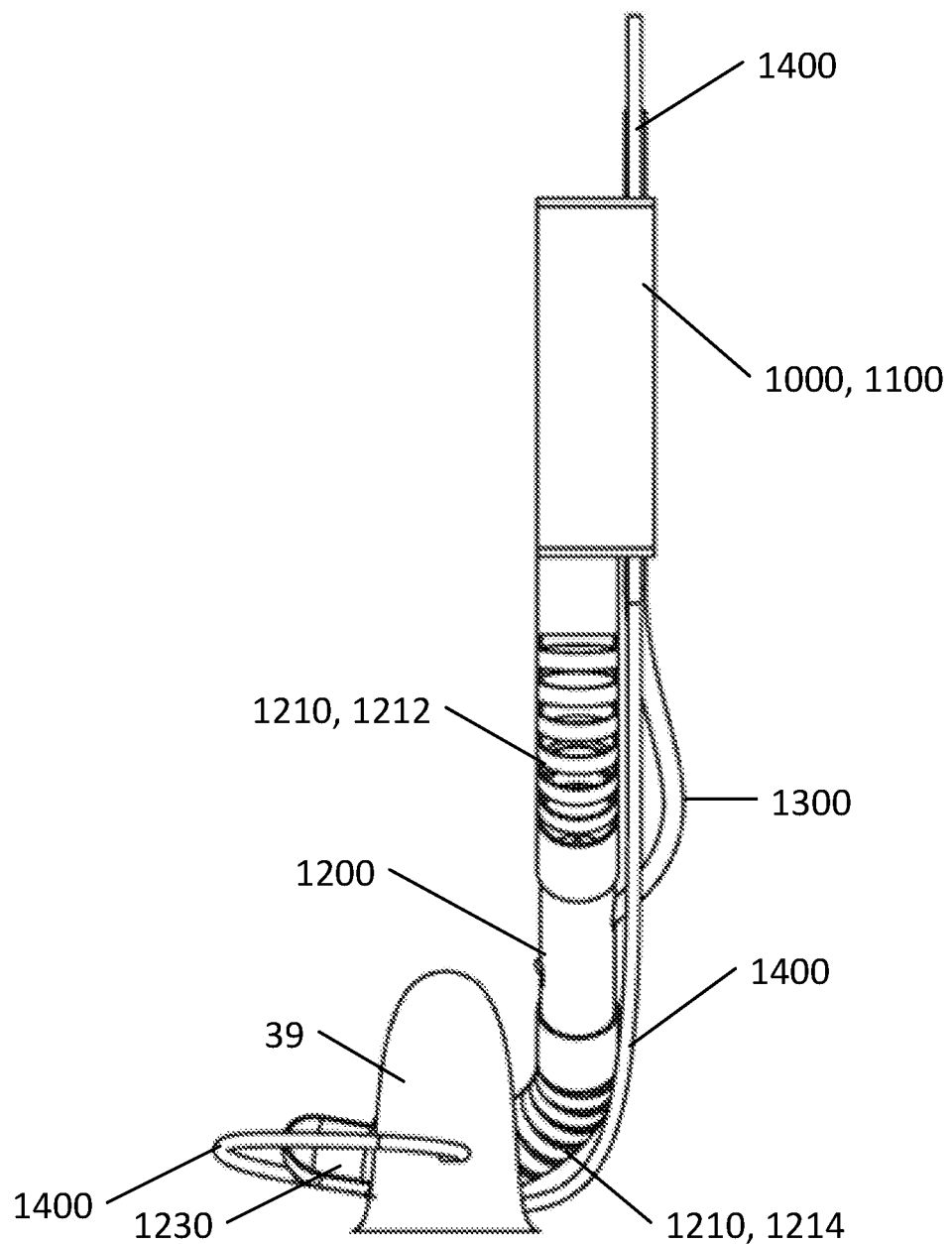
FIG. 17E is a side elevation view of the papillary catheter shown in FIG. 15A in a deformed configuration encircling a papillary muscle.
Figure 17F:
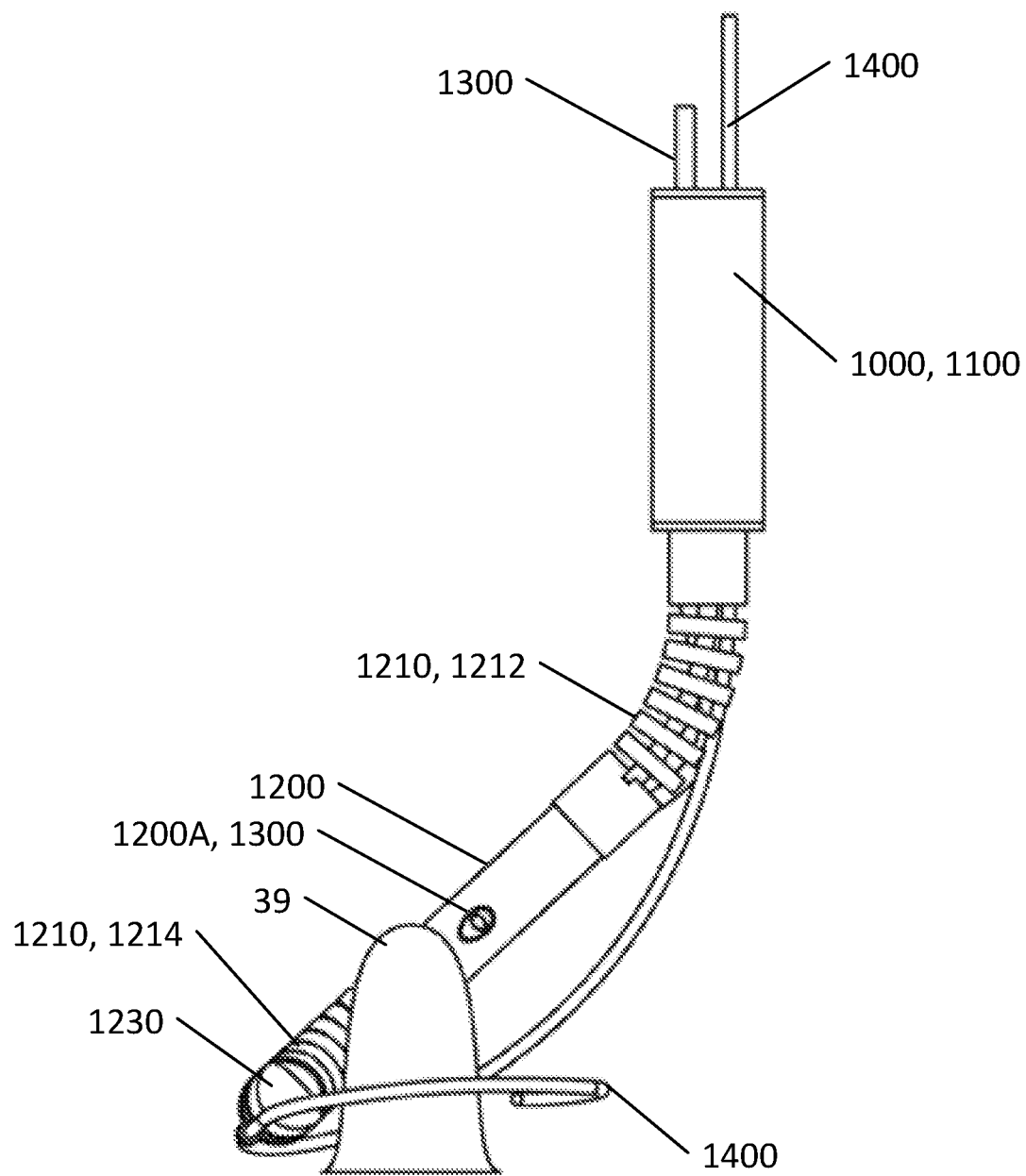
FIG. 17F is a front elevation view of the catheter and papillary muscle shown in FIG. 17E.
Figure 17G:
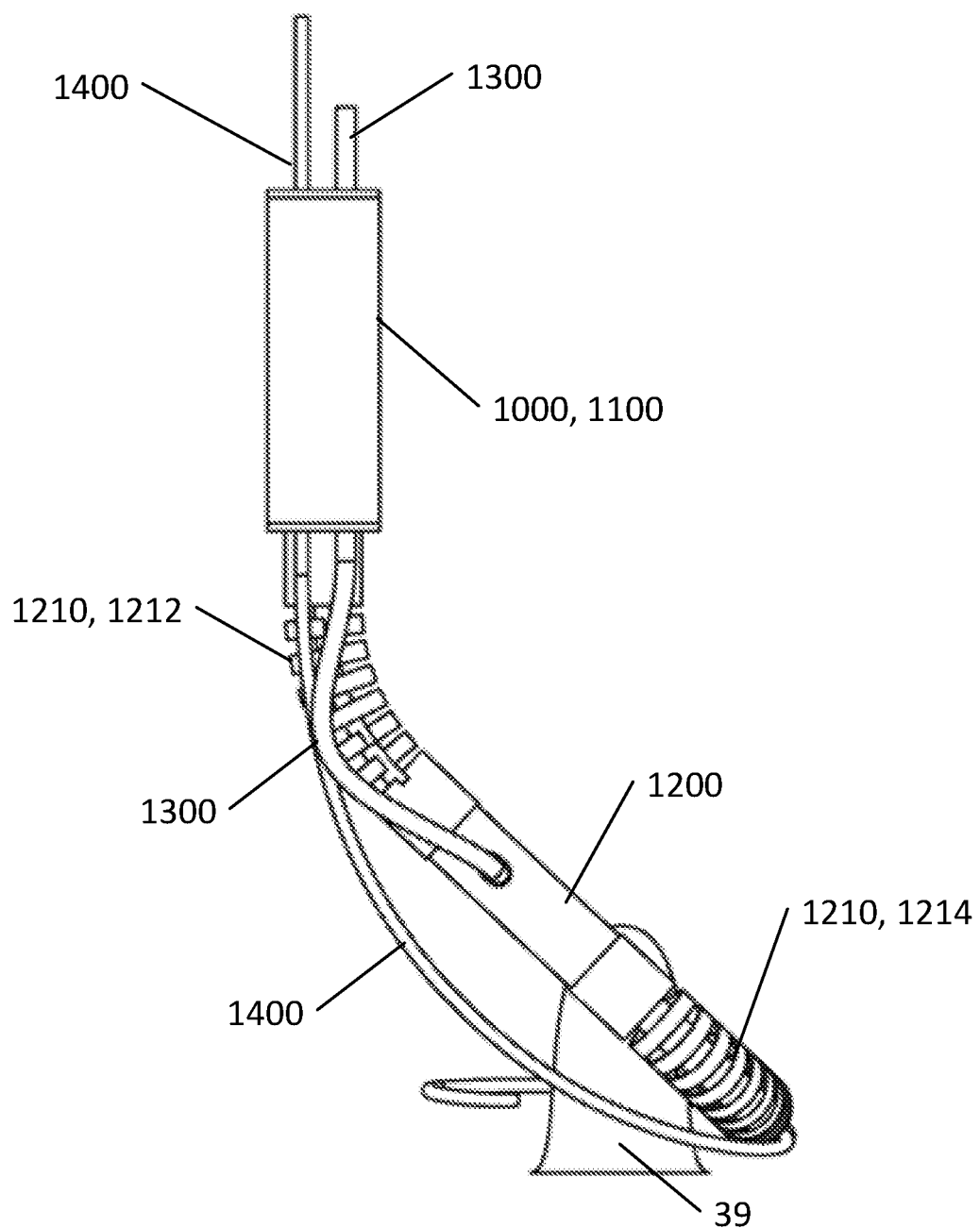
FIG. 17G is a rear elevation view of the catheter and papillary muscle shown in FIG. 17E.
Figure 17H:
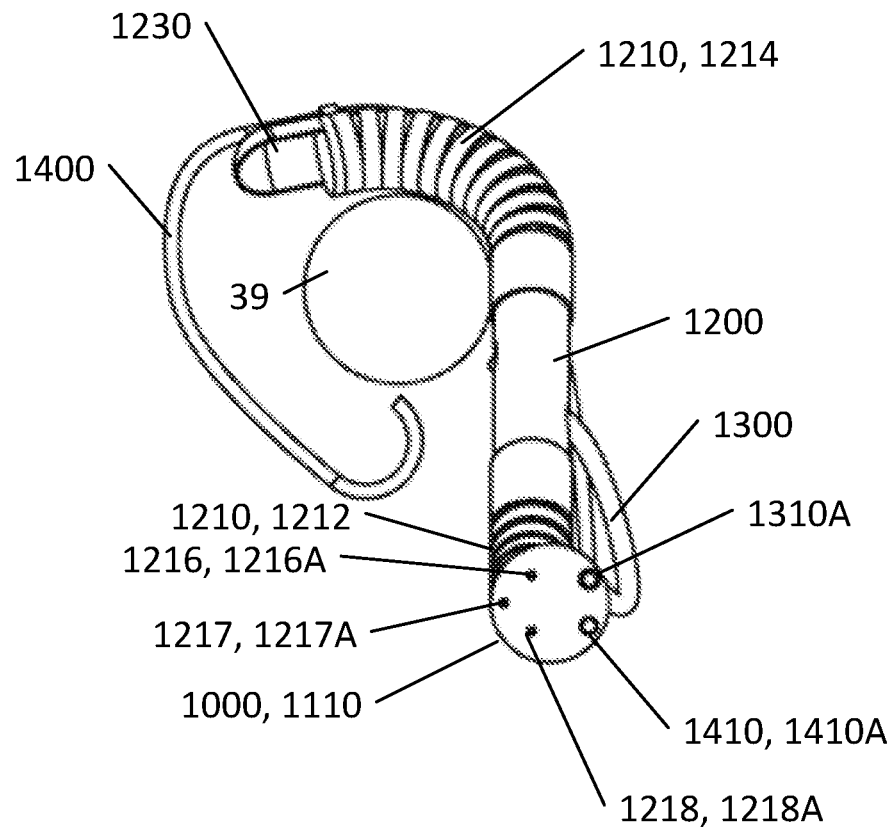
FIG. 17H is a top view of the catheter and papillary muscle shown in FIG. 17E.
Figure 17I:
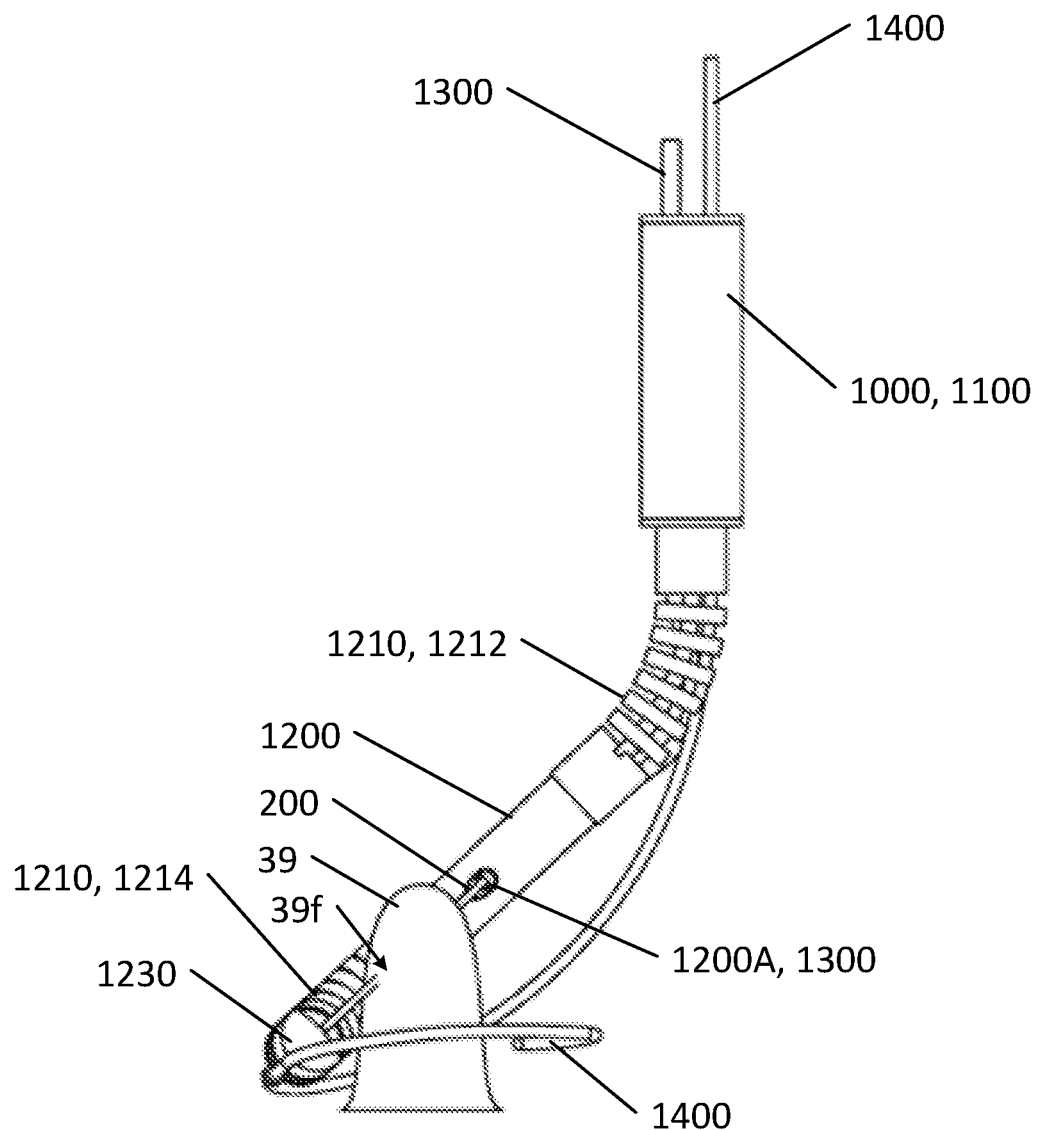
FIG. 17I is a front elevation view of the papillary catheter shown in FIG. 17A in a deformed configuration advancing a papillary anchor through a papillary muscle.
Figure 17J:
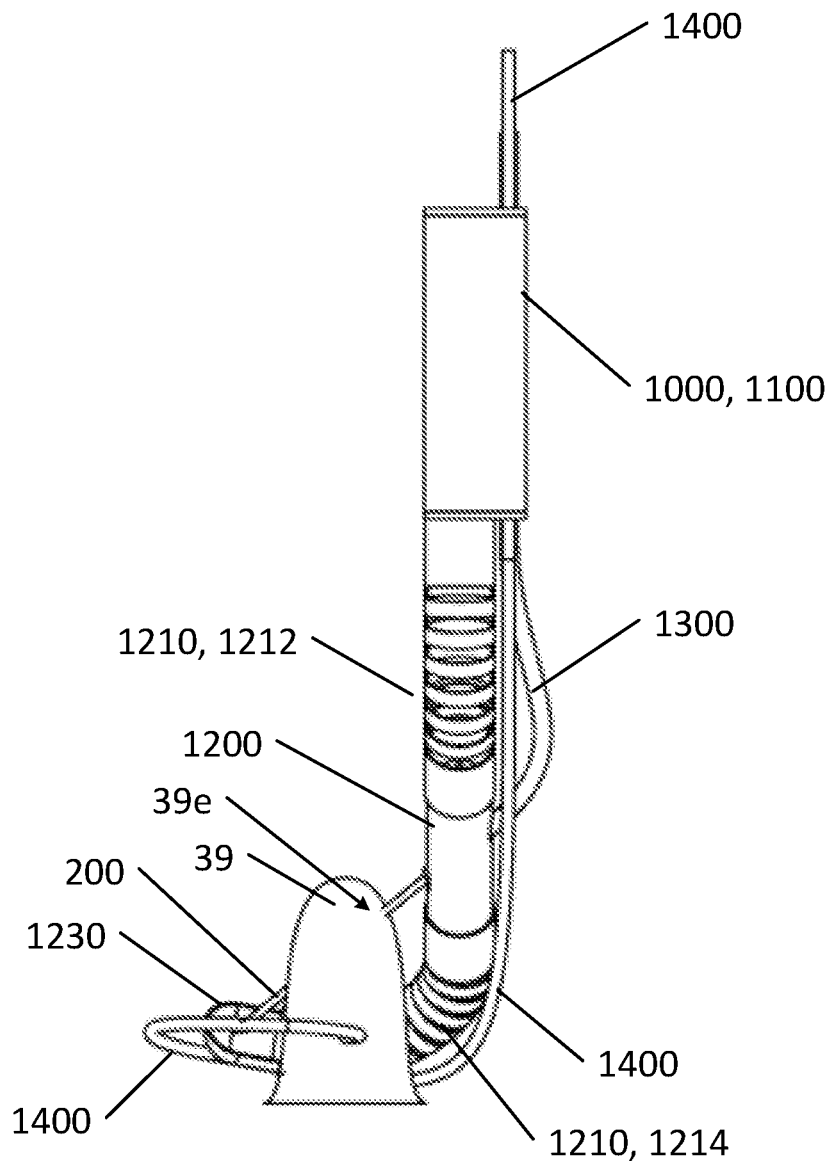
FIG. 17J is a side elevation view of the catheter, anchor, and papillary muscle shown in FIG. 17I.
Figure 17K:
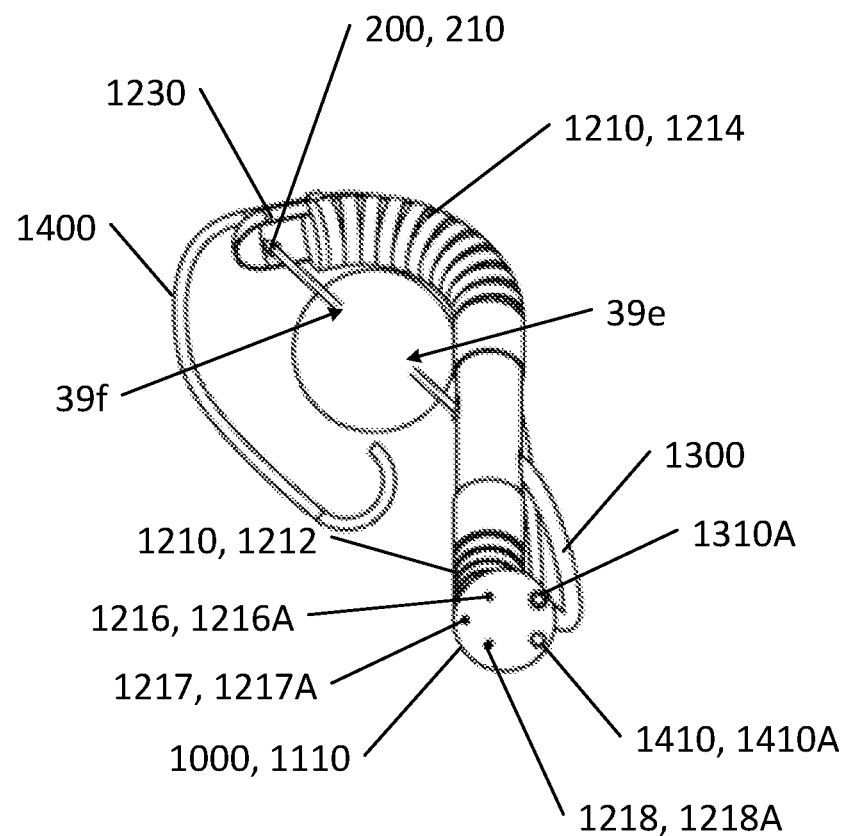
FIG. 17K is a top view of the catheter, anchor, and papillary muscle shown in FIG. 17I.

An example embodiment of a papillary anchor catheter is shown in FIGS. 15A-15L and 17A-17L. Catheter 1000 comprises a body 1100, a deformable arm 1200 extending away from body 1100, and an anchor housing 1300 connecting body 1100 and arm 1200. Anchor housing 1300 is configured to house anchor 200 as catheter 1000 is advanced through a patient's circulatory system via a conventional endovascular introducer (not shown) (or other device considered to be within the knowledge of persons skilled in the art of interventional cardiology). Anchor housing 1300 extends through a channel 1310A (FIG. 15D) defined by body 1100 and through a channel 1200A (FIG. 15B) defined by arm 1200. Catheter 1000 further comprises a guidewire 1400 extending from body 1100 alongside arm 1200 for directing catheter 1000 to a papillary muscle within the heart. Guidewire 1400 extends through a channel 1410A (FIG. 15D) defined by body 1100. The length of guidewire 1400 is sufficient to traverse the patient's circulatory system from papillary muscle 39 to a femoral vein puncture (i.e. the access site to the patient's circulatory system) and to operate guidewire 1400 external the patient. Guidewire 1400 may be soft and flexible for delivery about the papillary muscle without snaring or passing through the adjacent ventricular wall.

Catheter 1000 is deformable so that anchor 200 may be advanced through the papillary muscle with minimal snaring and/or entangling tissues and/or valve structures in the heart and surrounding the papillary muscles. In the illustrated embodiment, arm 1200 comprises at least one deformable section 1210. In some embodiments, each deformable section 1210 comprises a plurality of modular pieces arranged linearly and a tensioning wire 1216, 1218 extending through the pieces. To deform each section 1210, tension is applied to wire 1216, 1218. In the illustrated embodiment, arm 1200 comprises a first deformable section 1212 and a second deformable section 1214. In some embodiments, first deformable section 1212 is deformable by about by 0° to about 120° in a direction in a first plane. In some embodiments, second deformable section 1214 is deformable by about 0° to about 90° in a first direction in a second plane and by about 0° to about −90° in a second direction in the second plane. In some embodiments, the first plane and the second are non-coplanar. In some embodiments, the first plane is perpendicular to the second plane. Persons skilled in the art will recognize that each deformable section may be deformable in a plurality of directions and/or in a plurality of planes. To deform arm 1200, catheter 1000 comprises a wire for operating each deformable section. In the illustrated embodiment, catheter 1000 comprises a wire 1217 for operating first deformable section 1212 and wires 1216, 1218 for operating second deformable section 1214. In some embodiments wire 1217 deforms first deformable section 1212 in a first direction (e.g. by about 0° to about 120°) in a first plane. In some embodiments wire 1216 deforms second deformable section 1214 in a first direction (e.g. by about 0° to about 90°) in a second plane and wire 1218 deforms second deformable section 1214 in a second direction (e.g. by about 0° to about −90°) in the second plane. In some embodiments, the first plane and the second plane are non-coplanar. In some embodiments, the first plane and the second plane are perpendicular. Wires 1216, 1217, 1218 each extend through a respective channel 1216A, 1217A, 1218A (FIG. 15D) defined by body 1100. The length of each wire 1216, 1217, 1218 is sufficient to traverse the patient's circulatory system from papillary muscle 39 to a femoral vein puncture (i.e. the access site to the patient's circulatory system) and to operate arm 1200 external the patient. In some embodiments, one or more of anchor housing 1300, guidewire 1400, wire 1216, wire 1217, and wire 1218 are connected to a controller (not shown) external the patient for operating catheter 1000 and/or the parts thereof internally.

Catheter 1000 is shown in an extended configuration in FIGS. 15I-15L. In the extended configuration, catheter 1000 may be advanced through a patient's circulatory system and positioned adjacent a papillary muscle with minimal snaring and/or entangling tissues and/or valve structures in the heart and surrounding the papillary muscles. To implant anchor 200, catheter 1000 is deformable as described elsewhere herein.

As shown in FIGS. 15E-15H, arm 1200 is deformable about first deformable section 1212 into a deflected configuration. Catheter 1000 may be deformed into the deflected configuration in the left ventricle to facilitate access to the papillary muscle and implantation of anchor 200. In the deflected configuration, guidewire 1400 may be advanced about the papillary muscle to guide catheter 1000 in a position to implant anchor 200 with minimal snaring and/or entangling tissues and/or valve structures surrounding the papillary muscle. FIGS. 17A-17D show catheter 1000 deformed about first deformable section 1212 into the deflected configuration and delivery of guidewire 1400 to at least partially encircle the papillary muscle. With guidewire 1400 at least partially encircling the papillary muscle, catheter 1000 may be further advanced to implant anchor 200 with minimal snaring and/or entangling tissues and/or valve structures surrounding the papillary muscle.

As shown in FIGS. 15A-15D, arm 1200 is deformable about second deformable section 1214 into a hook-like or deformed configuration. Catheter 1000 may be deformed into the deformed configuration in the left ventricle to facilitate access to the papillary muscle. For example, in the deformed configuration, catheter 1000 may be positioned to advance anchor 200 through a papillary muscle and receive pin 210 so that minimal snaring and/or entangling of tissues and/or valve structures surrounding the papillary muscle occurs. In some embodiments, arm 1200 comprises a receiver 1230 for receiving pin 210. Example embodiments of a receiver are shown in FIGS. 16A and 16B. Receiver 1230 (FIG. 16A) comprises a recess 1232 for receiving pin 210. Receiver 1240 (FIG. 16B) comprises an anchor fastener 1242 for receiving pin 210 of anchor 200. When pin 210 is in its pre-deformed shape, fastener 1242 disperses any retracting forces anchor 200 has on the papillary muscle thereby preventing anchor 200 from being retracted back through the papillary muscle.

FIGS. 17E-17K show catheter 1000 deformed in a first direction in a first plane about first deformable section 1212 and in a second direction in a second plane about second deformable section 1214, wherein the first plane is perpendicular to the second plane. Deformed about first and second deformable sections 1212, 1214, arm 1200 may be advanced along guidewire 1400 to at least partially encircle the papillary muscle. With arm 1200 at least partially encircling the papillary muscle, anchor 200 may be advanced through the papillary muscle and pin 210 of anchor 200 may be received by receiver 1230. In some embodiments anchor 200 is advanced through a transverse dimension of the papillary muscle from an entrance site 39e of the papillary muscle to an exit site 39f of the papillary muscle. Pin 210 is received by receiver 1230 adjacent exit site 39f. In this way, snaring and/or entangling tissues and/or valve structures surrounding the papillary muscle are minimized or avoided. Thus, catheter 1000, prevents pin 210 from extending through the papillary muscle and piercing and/or damaging tissue of the left ventricle (i.e. the ventricular wall). In some embodiments, anchor 200 is advanced from entrance site 39e to exit site 39f through the center of the papillary muscle. In some embodiments, anchor 200 is advanced from entrance site 39e to exit site 39f through the papillary muscle in such a way to enhance the grab on the papillary muscle to thereby minimize or avoid anchor 200 from being torn out of the papillary muscle. In some embodiments, anchor housing 1300 is configured to advance anchor 200 through the papillary muscle in such a way to enhance the grab on the papillary muscle, thereby minimizing or avoiding anchor 200 from being torn out of the papillary muscle. For example, the diameter of anchor housing 1300 may be selected to house a rigid anchor 200 and advance the anchor through the papillary muscle with an optimal amount of grab on the papillary muscle.

Once advanced from anchor housing 1300, pin 210 resumes a pre-deformed shape (e.g. one of the shapes shown in FIGS. 9A-9D and 11A-11D). As such, pin 210 is not retractable through the papillary muscle. Tether 220 extends through the papillary muscle and anchor 200 is thereby secured through the muscle. With anchor 200 secured to the papillary muscle, catheter 1000 may be withdrawn from the patient's circulatory system by withdrawing catheter 1000 (in the extended configuration) from the patient via the introducer. Conventional Transesophageal Echocardiography (TEE) and/or fluoroscopy techniques may be used to advance and retract the catheter through a patient's circulatory system and implant anchor 200 through the papillary muscle.

In some embodiments, catheter 1000 comprises a controller (not shown) for operating the device extravascularly. When catheter 1000 is situated intravascularly, as described elsewhere herein, the controller is located external to the patient's body. In some embodiments the controller includes a handle and means for operating catheter 1000 and the parts thereof.

In some embodiments, catheter 1000 and/or the parts thereof comprise a sterilized or sterilisable material. In some embodiments, catheter 1000 and/or the parts thereof comprise one or more of medical grade plastic, thermal plastic, stainless steel, metal, a metal alloy (e.g. Nitinol™ or another nickel/titanium alloy), and titanium. Persons skilled in the art will recognize that catheter 1000 and/or the parts thereof may be made of any sterilized or sterilisable material conventionally used to manufacture tools used in heart surgery.

To implant apparatus 100, one or more annular anchors are secured to mitral annulus 32 as described elsewhere herein. In the embodiment illustrated in FIG. 5E, three anchors 500 are secured to mitral annulus 32. Papillary anchors are secured to each of anterior-lateral papillary muscle 39a and posterior-medial papillary muscle 39b as described elsewhere herein. Once a first papillary anchor is implanted into a first papillary muscle, a second papillary anchor may be implanted into a second papillary muscle. In the embodiment illustrated in FIGS. 5C-5D, one anchor 200 is secured to each papillary muscle. Persons skilled in the art will recognize that any suitable number of papillary anchors and annular anchors may be used to position apparatus 100 is a desired position and location in heart 10. The papillary anchors may be implanted in the papillary muscles before, after, or at approximately the same time that one or more annular anchors are implanted into the mitral annulus.

Figure 18:
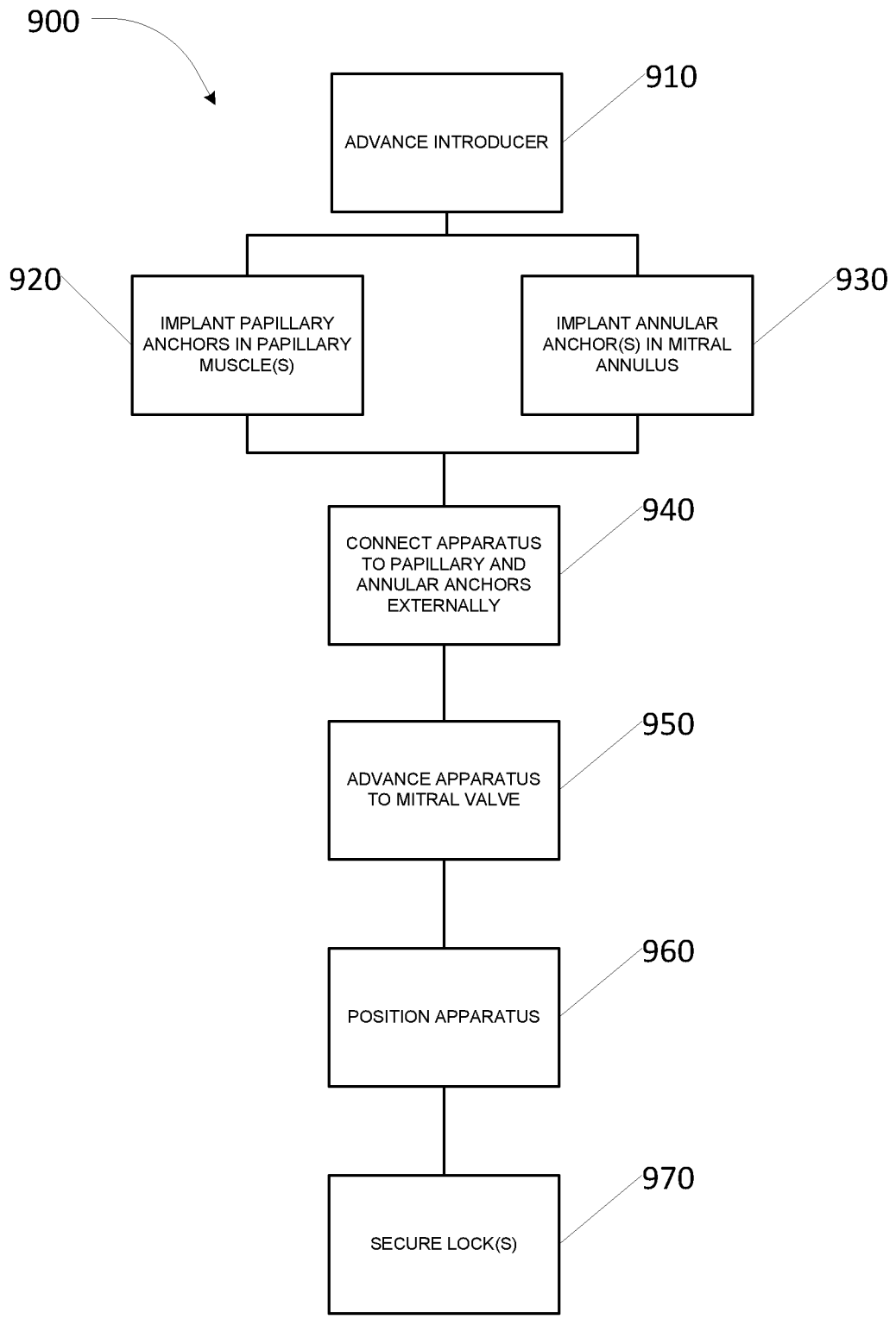
FIG. 18 is a flow chart of a method of repairing a mitral valve according to an example embodiment of the present invention.
Figure 19E:
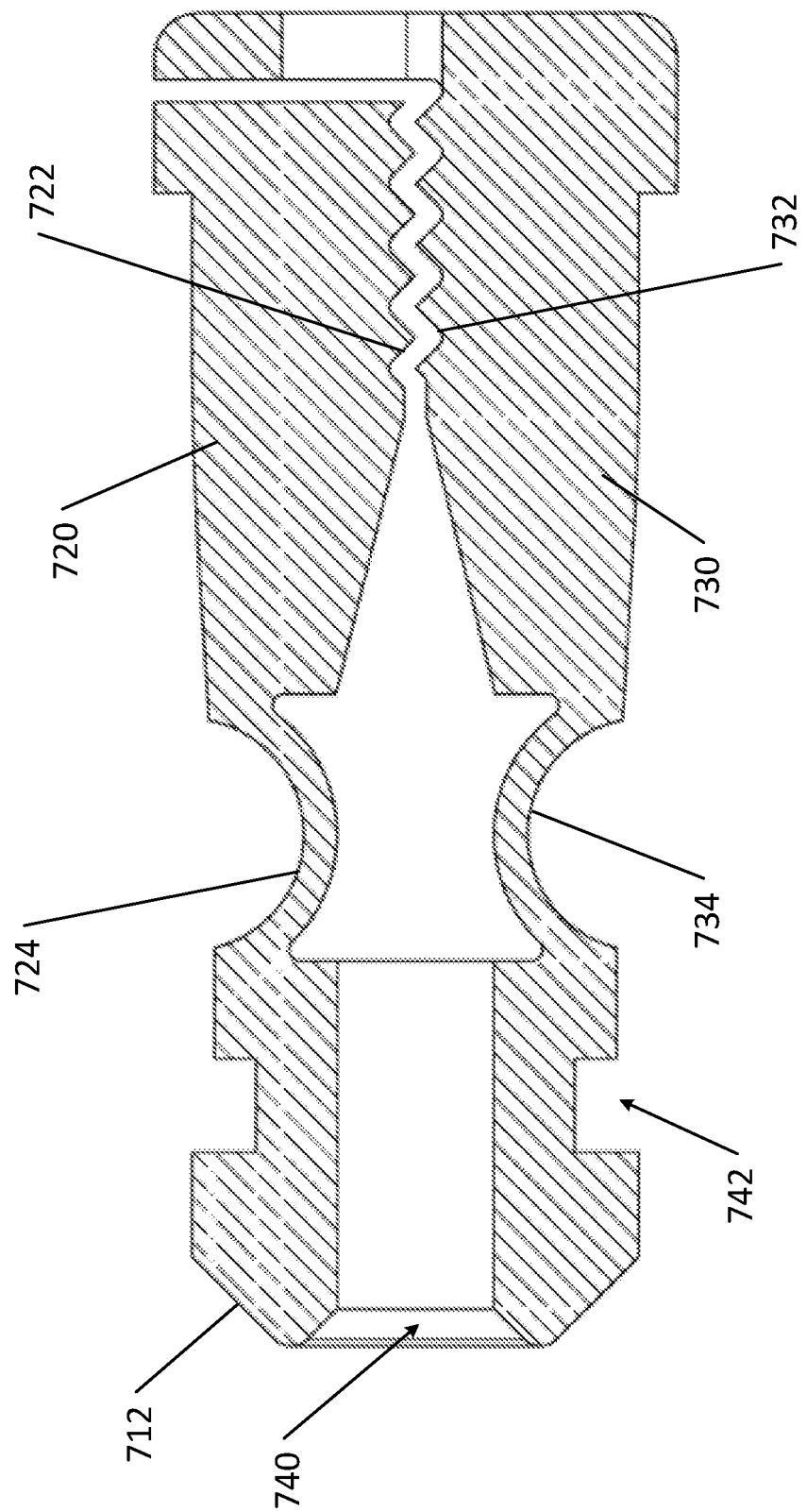
FIG. 19E is side elevation cross-sectional view of the lock shown in FIG. 19A taken along the line A-A.

A method 900 for repairing a mitral valve of a heart according to an example embodiment is shown in FIG. 18. In block 910 a conventional transatrialseptal introducer (not shown) (or other device considered to be within the knowledge of persons skilled in the art of interventional cardiology) is inserted into a patient's circulatory system and advanced using a transcatheter approach as described elsewhere herein. One or more papillary anchors and annular anchors are implanted respectively in the patient's mitral annulus and papillary muscle(s) in respective blocks 920 and 930, as described elsewhere herein.

Once implanted in the heart, the papillary anchors and the annular anchor(s) are used to advance and guide apparatus 100 through a patient's circulatory system to a desired implant site and to position apparatus 100 in the heart. In block 940 apparatus 100 is externally connected to the guidewires of the papillary and annular anchors. Guidewires 230 secured to the anterior-lateral papillary muscle are externally advanced through a first end 140A of tube 140 of anterior member 120 and/or a first end 150A of tube 150 of posterior member 130. Guidewires 230 secured to the posterior-medial papillary muscle are externally advanced through a second end 140B of tube 140 of anterior member 120 and/or a second end 150B of tube 150 of posterior member 130. Guidewire(s) 530 secured to the mitral annulus is/are advanced externally through body 110 at one or more anchor sites (not shown). In some embodiments, the guidewire of each anchor 500 is advanced through skirt 114 at one or more anchoring sites 111. The anchoring sites 111 may be positioned anywhere through body 110 and/or skirt 114 so that body 110 may be advanced along guidewire(s) 530 to mitral annulus 32 where the body is positioned against the atrial muscle (not shown) adjacent the mitral annulus. In some embodiments, body 110 is shaped like the mitral annulus of a heart for positioning body 110 against the atrial muscle.

With guidewires 230, 530 connected to apparatus 100 externally, apparatus 100 may then be inserted inside the introducer by radially compressing body 110 (as described elsewhere herein) to implant apparatus 100 inside the heart. In block 950 apparatus 100 is advanced endovascularly to an implant site to position apparatus 100 in heart 10. Once positioned at the desired implant site, apparatus 100 is radially expanded as described elsewhere herein by releasing apparatus 100 from the introducer. In block 960 apparatus 100 is adjusted to position anterior member 120 and/or posterior member 130 to adjust the extent of atrial displacement of the mitral leaflets during ventricular contraction and correct leaflet prolapse and/or restore mitral valvular competence. Conventional Transesophageal Echocardiography (TEE) and/or fluoroscopy techniques may be used to guide apparatus 100 along the guidewires through the patient's circulatory system to position apparatus 100 in the desired implant site (e.g. the mitral valve).

Body 110 is advanced along guidewire(s) 530 to mitral annulus 32 where the body is positioned against the atrial muscle (not shown) adjacent the mitral annulus. In some embodiments, body 110 is shaped like the mitral annulus of a heart for positioning body 110 against the atrial muscle. To secure body 110 to mitral annulus 32, a lock 700 (described elsewhere herein) is advanced in an open configuration along each guidewire 530 to the corresponding anchor site (not shown) of body 110 via a lock catheter 800 (described elsewhere herein). Lock 700 is secured in a locked configuration to tether 520 adjacent each anchor site. With lock 700 secured, tether 520 may be cut and guidewire 530 withdrawn from the patient.

Tube 140 and/or tube 150 is advanced along guidewire(s) 230 through the mitral valve and into the left ventricle adjacent the corresponding papillary muscle. In this way, end 140A and/or 150A of tube 140 is connected to anterior-lateral papillary muscle 39a via a first anchor 200 and end 140B and/or 150B of tube 150 is connected to posterior-medial papillary muscle 39b via a second anchor 200. Thereby, tube 140 and/or tube 150 traverses the papillary muscles, from anterior-lateral papillary muscle 39a to posterior-medial papillary muscle 39b (FIGS. 5C-5D). By adjusting the length of tube 140 and/or tube 150 as described elsewhere herein, the extent of atrial displacement of the mitral leaflets during ventricular contraction can be adjusted. The tension of cord 142 and/or cord 152 may be adjusted as described elsewhere herein to adjust the extent of atrial displacement of the mitral leaflets during ventricular contraction. The length of tube 140 and/or tube 150 and the tension of cord 142 and/or cord 152 may be adjusted using ultrasound guidance. As described elsewhere herein, lock 700 may be advanced in an open configuration along cord(s) 142, 152 to abut against an end of tube(s) 140, 150. Lock 700 is secured in a locked configuration to cord(s) 142, 152 adjacent tube(s) 140, 150 to secure tube(s) 140, 150 in a desired length and member(s) 120, 130 in a desired position covering an atrial surface of the mitral leaflet. With lock 700 secured, cord (s) 142, 152 may be cut adjacent the lock and the free end withdrawn from the patient. When installed, apparatus 100 may correct leaflet prolapse and/or restore mitral valvular competence.

In some embodiments, to optimize the extent of atrial displacement of the mitral leaflets during ventricular contraction when apparatus 100 is implanted and under tension as described elsewhere herein, conventional Transesophageal Echocardiography (TEE) and/or fluoroscopy techniques are used to optimize a distance between an atrial edge 110a (FIG. 4A) of body 110 and an anchor point in papillary muscle 39.

In block 960 one or more locks 700 (described elsewhere herein) may be advanced using a lock catheter (described elsewhere herein) to secure apparatus 100 in a desired location and position. Conventional Transesophageal Echocardiography (TEE) and/or fluoroscopy techniques may be used to advance lock 700 and the lock catheter through a patient's circulatory system to a desired location.

An example embodiment of lock 700 is shown in FIGS. 19A-19E. Lock 700 comprises a body 710 defining opposed jaws 720, 730 and a channel 740 extending lengthwise through the body for receiving a guidewire and/or a tether of a papillary anchor and/or an annular anchor. In the embodiment shown in FIGS. 19A-19E, lock 700 is hairpin-shaped and body 710 tapers from jaws 720, 730 to an opposed end 712 to facilitate delivery of lock 700 via a lock catheter (described elsewhere herein). In some embodiments body end 712 defines a recess 742 shaped concentrically about channel 740 for engaging the catheter as described elsewhere herein.

Lock 700 is biased in a locked configuration shown in FIGS. 19A-19E. In the locked configuration, jaws 720, 730 are operable to clasp a guidewire and/or a tether extending therebetween. To improve the strength of the clasp on the guidewire or tether, jaws 720, 730 may define teeth 722, 732 for gripping the guidewire or tether. In an open configuration (best shown in FIGS. 20C, 20F, 20J, and 20K) jaws 720, 730 are deflected away from one another and lock 700 is free to move along the guidewire or tether. Each jaw 720, 730 defines a flexible arm 724, 734. In some embodiments, pressure may be applied to arms 724, 734 to deflect jaws 720, 730 in the open configuration. In some embodiments, jaws 720, 730 may be deflected away from one another by inserting a needle or other similar means between the jaws.

Figure 21:
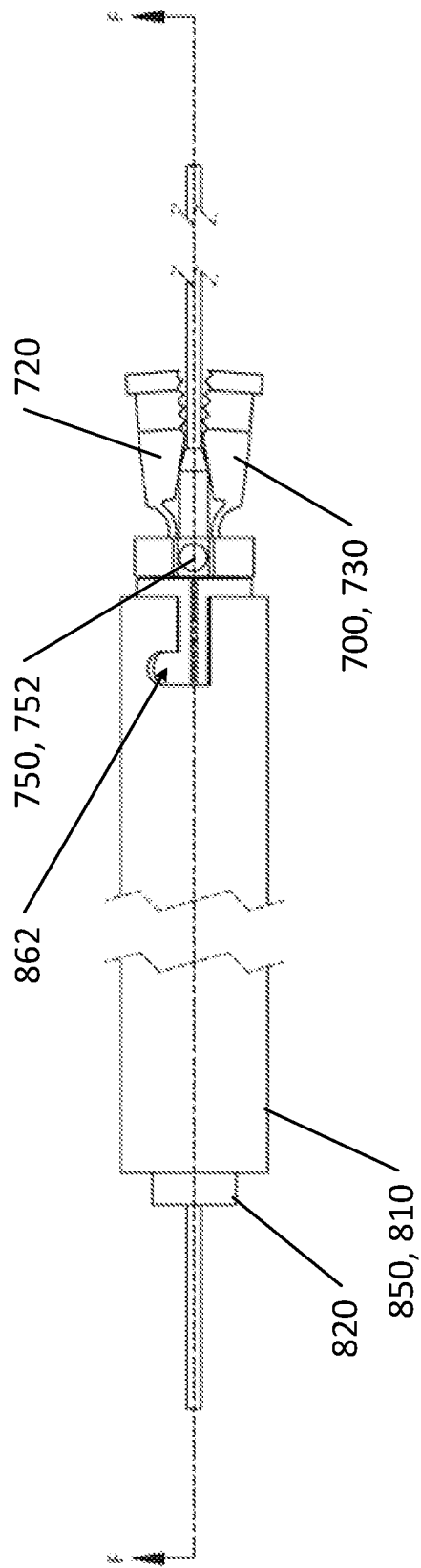
FIG. 21 is a side elevation view of a lock catheter according to example embodiment of the present invention advancing the lock shown in FIG. 18A along a guidewire in an open configuration.

To secure lock 700 to a guidewire and/or tether, lock 700 is advanced in the open configuration along the guidewire and/or tether using a lock catheter (FIGS. 20A-20K). Example embodiments of a lock catheter are shown in FIGS. 20A-20N and 21. Lock catheter 800 (FIGS. 20A-20N) comprises a sleeve tube 810 housing a lock tube 820. Lock tube 820 is configured to engage recess 742 of lock 700 to advance or retract lock 700 along guidewire and/or tether. Lock tube 820 houses a deploying tube 830 for disengaging lock 700 from lock tube 820 by advancing deploying tube 830 towards end 712 of lock 700.

In some embodiment, lock tube 820 comprises at least one cut (not shown) longitudinally extending from a lock engaging end 820a thereof through at least a portion of the lock tube. In some embodiments, deploying tube 830 comprises at least one cut (not shown) longitudinally extending from a lock abutting end 830a thereof through at least a portion of the deploying tube. To deploy lock 700 from catheter 800, a force is applied to deploying tube 830 to advance lock abutting end 830a against end 712 of lock 700. As end 830a abuts against end 712, deploying tube 830 splits open along the at least one cut, increasing the diameter of lock abutting end 830*a*, and forcing end 830*a* against lock tube 820. As end 830*a* abuts against lock tube 820, lock tube 820 splits open along the at least one cut, increasing the diameter of lock engaging end 820*a*, releasing lock tube 820 from recess 742 of lock 700, and deploying lock 700 from catheter 800.

In some embodiments, lock 700 may be retrieved using catheter 800 by forcing lock abutting end 830*a* of deploying tube 830 against lock tube 820 to split open lock tube 820, thereby increasing the diameter of lock engaging end 820*a*. Catheter 800 is advanced to position lock engaging end 820*a* of lock tube 820 with recess 742 of lock 700. To engage lock engaging end 820*a* with recess 742, deploying tube 830 is retracted away from lock engaging end 820*a*. As deploying tube 830 is retracted, the diameter of ends 820*a*, 830*a* decreases and lock engaging end 820 mates with and engages recess 742.

In some embodiments catheter 800 comprises a needle 840 (best shown in FIGS. 20B, 20E, 20H, and 20K) for retaining lock 700 in the open configuration. Needle 840 extends over the guidewire and/or tether through channel 740 and deflects jaws 720, 730 away from the guidewire and/or tether. To secure lock 700 to the guidewire and/or tether, needle 840 may be withdrawn from channel 740 thereby allowing jaws 720, 730 to bias towards one another and biasing lock 700 in the closed configuration.

In some embodiments lock 700 comprises a ring-shaped collar 750 for retaining lock 700 in closed configuration. In the example embodiment shown in FIGS. 19A-19E jaws 720, 730 define recesses 728, 738 shaped concentrically about channel 740 for receiving collar 750 and retaining lock 700 in the locked configuration. Collar 750, positioned in recesses 728, 738, is operable to prevent jaws 720, 730 from deflecting away from one another (FIGS. 20L-20N).

In some embodiments, to move collar 750 along lock 700, collar 750 comprises at least one notch 752. Sleeve tube 810 of catheter 800 defines at least one recess 812 configured to engage notch(es) 752. In the embodiment shown in FIGS. 20A-20N sleeve tube 810 comprises recess 812 configured to engage notch 752 of collar 750. To secure lock 700 to the guidewire/tether, sleeve tube 810 is advanced over lock tube 820 towards collar 750. Sleeve tube 810 is rotated about the guidewire and/or tether to align recess 812 with notch 752. With recess 812 and notch 752 aligned, collar 750 may be moved with sleeve tube 810. Sleeve tube 810 may be advanced across lock tube 820 to push collar 750 towards jaws 720, 730 and position collar 750 within recesses 728, 738. Collar 750 thereby clasps jaws 720, 730 together to close and retain lock 700 in the locked configuration (FIG. 20L-20N). In some embodiments lock 700 is irreversibly locked in the closed configuration once collar 750 is advanced along jaws 720, 730 and positioned within recesses 728, 738. With lock 700 locked in the closed configuration and thereby secured to the guidewire and/or tether, catheter 800 may be withdrawn from the patient.

Many features and components of lock catheter 850 (FIG. 21) are similar to features and components of lock catheter 800, with the same reference numerals being used to indicate similar features and components. Sleeve tube 810 of catheter 850 defines at least one aperture 862 configured to receive at least one notch 752 of lock 700.

In some embodiments, catheter 800 comprises a controller (not shown) for operating the device extravascularly. When catheter 800 is situated intravascularly, as described elsewhere herein, the controller is located external to the patient's body. In some embodiments the controller includes a handle and means for operating catheter 800 and the parts thereof.

In some embodiments, catheter 400 comprises a controller (not shown) for operating the device extravascularly. When catheter 400 is situated intravascularly, as described elsewhere herein, the controller is located external to the patient's body. In some embodiments the controller includes a handle and means for operating catheter 400 and the parts thereof.

Lock 700 and the parts thereof may comprise one or more of medical grade plastic, thermal plastic, stainless steel, metal, a metal alloy (e.g. Nitinol™ or another nickel/titanium alloy), and titanium.

Catheter 800 and the parts thereof may comprise one or more of medical grade plastic, thermal plastic, stainless steel, metal, a metal alloy (e.g. Nitinol™ or another nickel/titanium alloy), and titanium. Persons skilled in the art will recognize that catheter 1000 and/or the parts thereof may be made of any sterilized or sterilisable material conventionally used to manufacture tools used in heart surgery.

FIGS. 22A-22D illustrate an apparatus 900 for repairing a heart valve, such as a mitral valve, according to an example embodiment of the invention. Apparatus 900 includes a radially compressible and radially expandable body 910, an anterior member 920, and a posterior member 930. In the illustrated embodiments, body 910 is a tube. Alternatively, body 910 has a shape similar to body 110 of apparatus 100 as seen in FIG. 4A. A radially compressible and radially expandable ring (not shown), having similar functions and properties as ring 112 discussed elsewhere here, may be arranged on or in body 910 to facilitate the radial compression and expansion thereof. A compressible and expandable ring is not mandatory; body 910 may, for example, be provided in a self-expandable form (e.g., the body is constrained within a delivery device such as within a catheter until positioned and deployed). Body 910 may also be expanded and contracted directly using external means such as an inflatable balloon.

Anterior member 920 is connected to an anterior end 919 of body 910. Posterior member 930 may be attached to a posterior end 918 of body 910. Each member 920, 930 comprises a section 922, 932. Sections 922, 932 may comprise a net-like structure defined by a plurality of cells 902. The plurality of cells 902 extend radially and longitudinally from body 910 to the plurality of positioning cords 924, 934. Cells 902 are hollow spaces that may permit the passage of blood therethrough.

Sections 922, 932 may include a plurality of positioning cords 924, 934 for positioning each member to cover an atrial surface of a mitral leaflet from a lateral commissure to a medial commissure thereof. Cords 924, 934 are spaced laterally across each section 922, 932 and extend from section 922, 932 away from body 910. Cords 924, 934 may be integrally formed with corresponding section 922, 932. Cords 924, 934 each terminate at and connect to a flexible, compressible tube 940, 950. Cords 924, 934 are laterally spaced across tube 940, 950. In some embodiments, cords 924, 934 are evenly spaced across tube 940, 950. Tubes 940, 950 may each comprise an adjustment cord 942, 952 secured to an end of the tube and extending longitudinally through the tube. In the illustrated embodiments, compressible tubes 940, 950 are rounded hollow tubes that are constructed of braided threads. Threads can be made of one or more of polytetrafluoroethylene (PTFE), expanded PTFE, polyethylene, polypropylene, polyethylene terephthalate, an extracellular matrix biomaterial, and a tissue engineered material.

Compressible tubes 940, 950 may however be provided in other suitable forms that are known in the art. Compressible tubes 940, 950 and adjustment cords 942, 952 are similar to tubes 140, 150 and cords 142, 152 respectively, which the latter have been discussed elsewhere here. The functions and properties of compressible tubes 940, 950 and adjustment cords 942, 952 are thus not repeated.

Figure 22A:
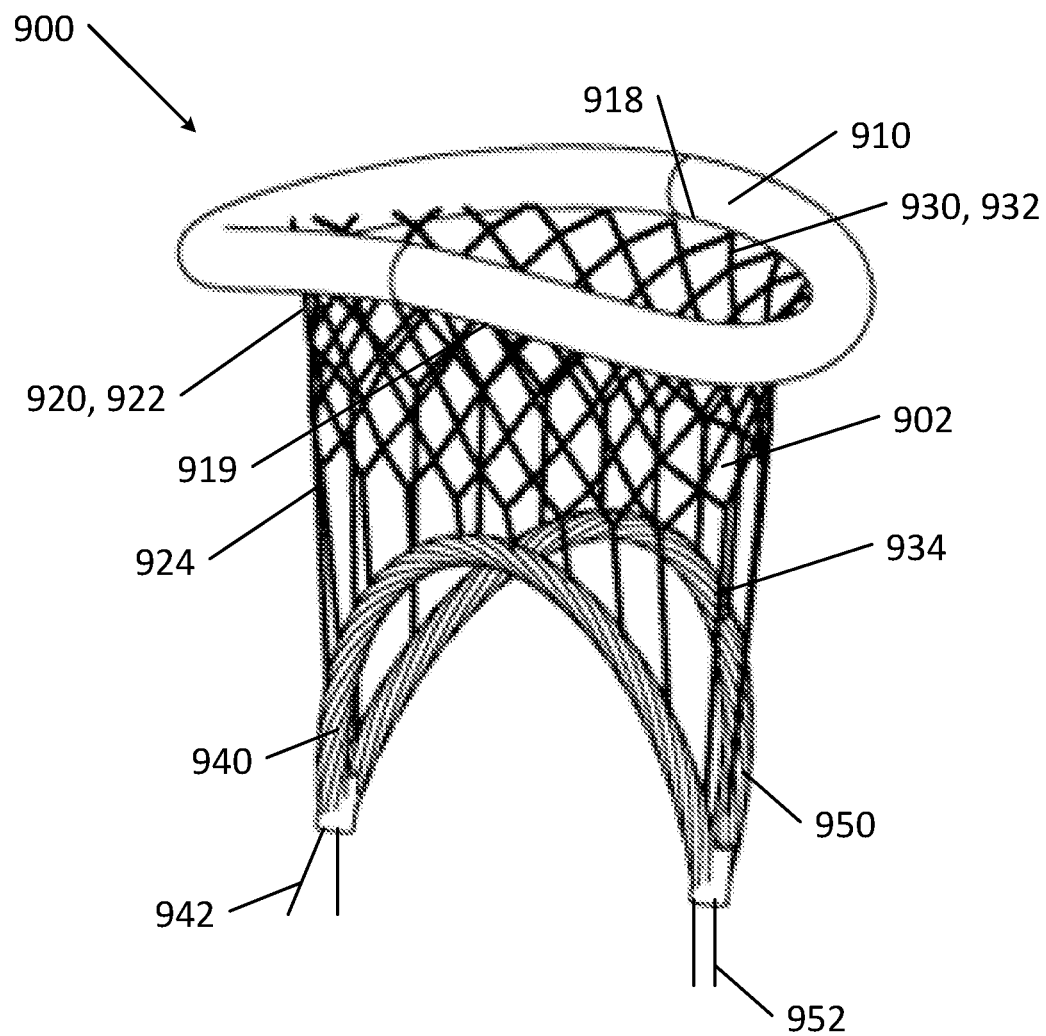
FIG. 22A is an anterior perspective view of an apparatus according to an example embodiment of the present invention.
Figure 22B:
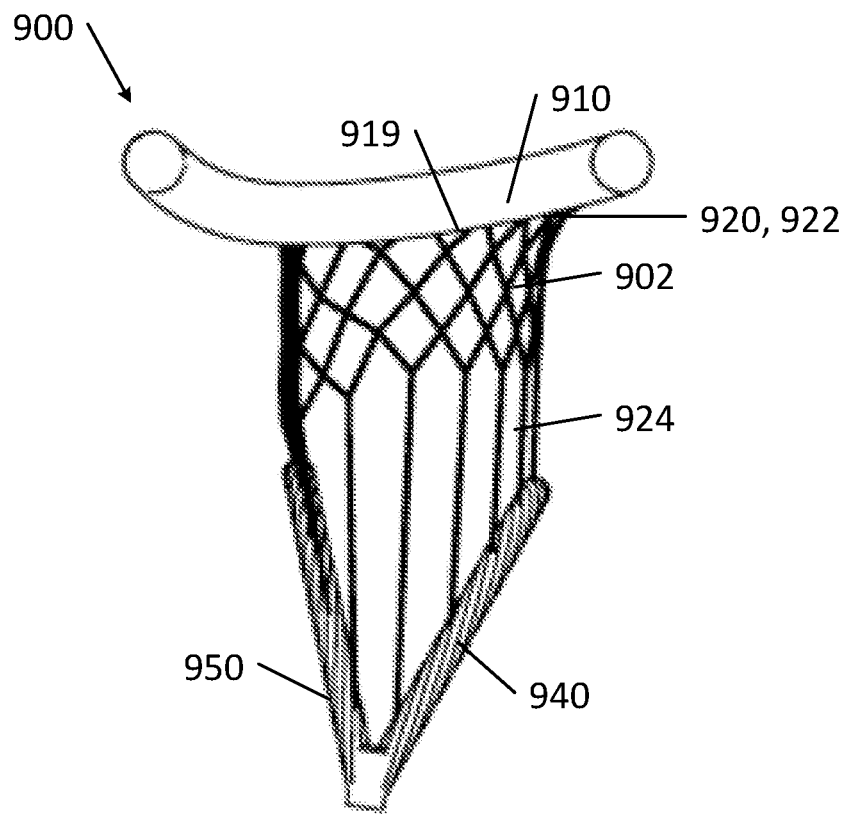
FIG. 22B is a partial side view of the apparatus shown in FIG. 22A.
Figure 22C:
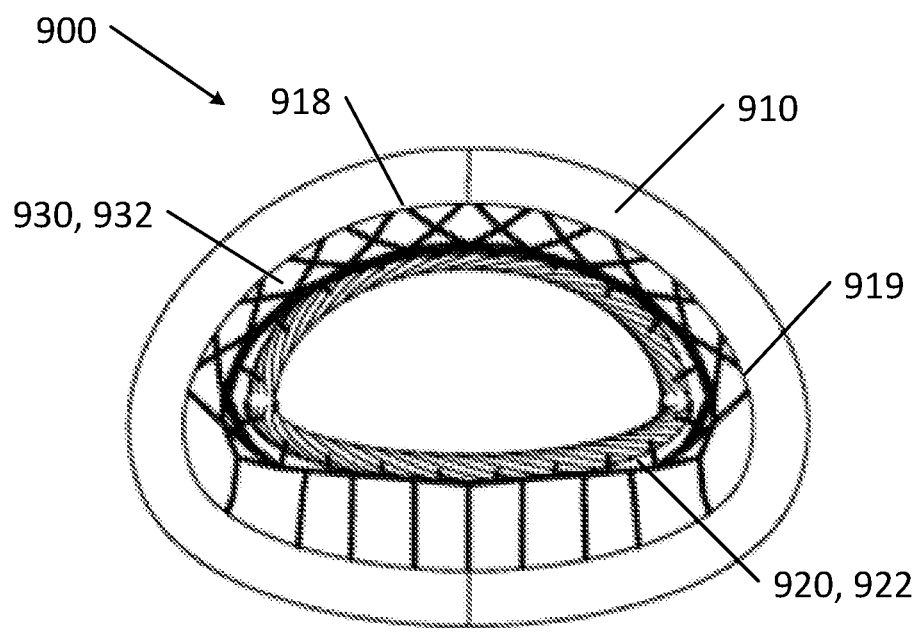
FIG. 22C is a top view of the apparatus shown in FIG. 22A.
Figures 22D, 22E:
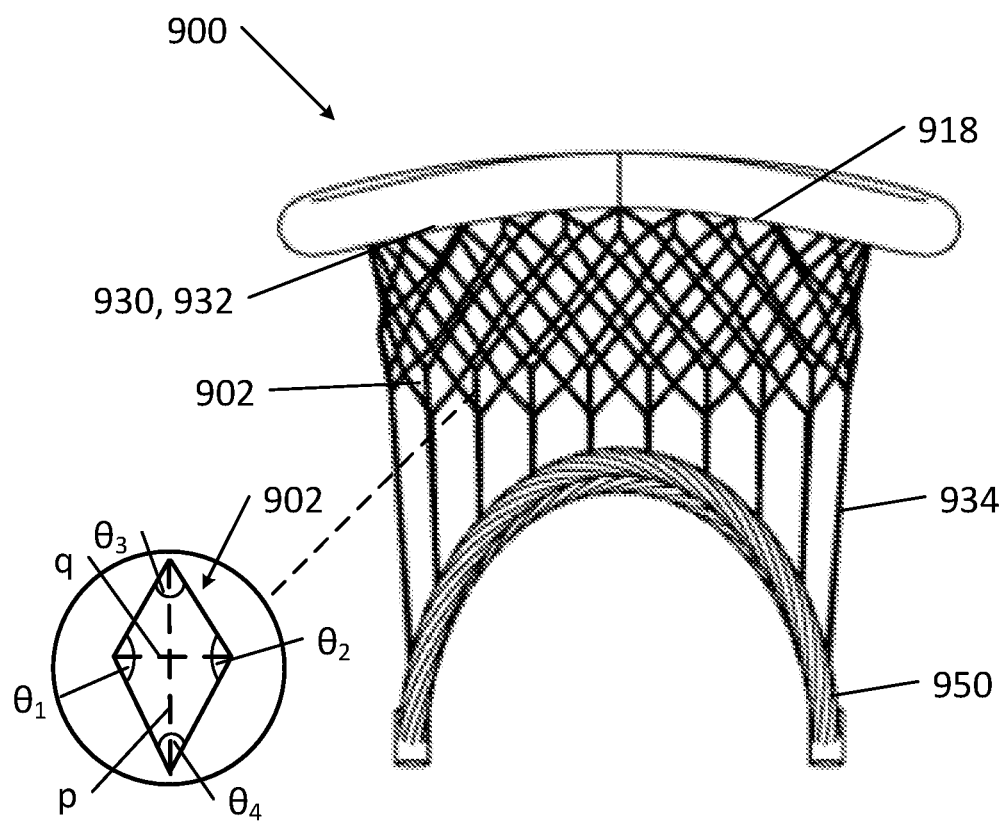
FIG. 22D is a posterior elevation view of the apparatus shown in FIG. 22A.
FIG. 22E is an isolated enlarged view of a cell shown in FIG. 22A.

Cells 902 may be contractable between a relaxed position and an elongated position. Cells 902 may be elongated and/or contracted laterally and/or longitudinally with respect to body 910. In some embodiments, each cell 902 has a diamond shape. A diamond is a quadrilateral having four sides of substantially equal lengths and four vertices with opposite angles that are equal ($\theta_1=\theta_2$ and $\theta_3=\theta_4$), and that one set of angles is greater than the other set ($\theta_1, \theta_2$ is greater than $\theta_3, \theta_4$), a schematic diagram of a diamond-shaped cell 902 is shown in FIG. 22E. In the illustrated embodiments (FIG. 22A-22D), the diamond-shaped cells 902 are aligned such that the vertices with the smaller angles ($\theta_3, \theta_4$) are positioned longitudinally with respect to body 910, and the vertices with the greater angles ($\theta_1, \theta_2$) are positioned laterally with respect to body 910. This is not mandatory; however. In some embodiments, cells 902 may be aligned such that the vertices with the smaller angles ($\theta_3, \theta_4$) are positioned laterally, and the vertices having the greater angles ($\theta_1, \theta_2$) are positioned longitudinally with respect to body 910.

Figure 23A:
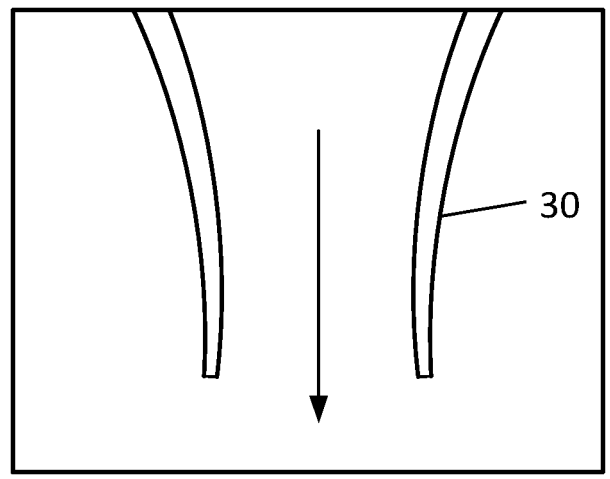
FIG. 23A is a schematic diagram illustrating a mitral valve that is fully open.
Figure 23B:
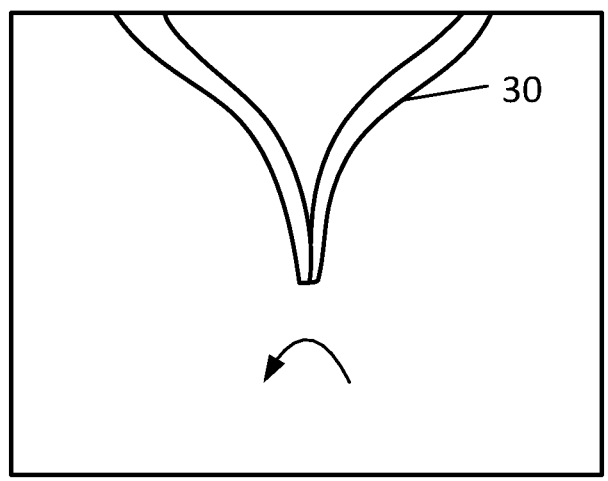
FIG. 23B is a schematic diagram illustrating a mitral valve that is fully closed.

When apparatus 900 is implanted in heart 10, the shape of sections 922, 932 changes in response to the opening and closing of mitral valve 30 during ventricular contraction. Mitral valve 30 changes in shape during the opening and closing of the valve. FIG. 23A is a schematic diagram illustrating a fully opened mitral valve 30. The arrow shows the direction of blood flow through the opened mitral valve 30. As shown in FIG. 23A, a fully opened mitral valve can be defined by a substantially cylindrical shape. A cylindrical shape may be defined by two parallel circular bases connected by a curved surface. FIG. 23A is a schematic diagram illustrating a fully closed mitral valve 30. The arrow shows that blood cannot flow backwards into atrium 20 through mitral valve 30. As shown in FIG. 23B, a fully closed mitral valve can be defined by a substantially hourglass shape. An hourglass shape may be defined by a convex front face that tapers axially towards to a constricted waist bottom.

In some embodiments, sections 922, 932 are transformable between a cylindrical configuration and an hourglass configuration in response to the respective opening and closing of mitral valve 30. Sections 922, 932 conform to the shapes of mitral valve 30 by the transition of cells 902 between the relaxed position and the elongated position. The shapes and sizes of cells 902 change between the relaxed and the elongated positions.

Sections 922, 932 may be in the cylindrical configuration when mitral valve 30 is open. In such embodiments, cells 902 may be in the relaxed position. In the relaxed position, cells 902 may be substantially uniform in size and shape. For example, in embodiments in which cells 902 are diamond shaped, cells 902 have identical or substantially similar diagonal length p (i.e., the distance between opposing longitudinal vertices), and have identical or substantially similar diagonal length q (i.e., the distance between opposing lateral vertices), as shown in the schematic diagram in FIG. 22E.

Sections 922, 932 may be in the hourglass configuration when mitral valve 30 is closed. In such embodiments, some or all of cells 902 may be in the elongated position. In the elongated position, cells 902 may not be uniform in size and shape. In some embodiments, the diagonal length p of cells 902 increases from posterior and anterior ends 918, 919 of body 910 to compressible tubes 940, 950. Diagonal length q of cells 902 may decrease from posterior and anterior ends 918, 919 of body 910 to compressible tubes 940, 950. In these embodiments, cells 902 near compressible tubes 940, 950 are elongated and narrow. The elongated and narrow cells 902 generally conform to the tapered waist bottom of the hourglass-shaped fully closed mitral valve.

Cells 902 that overlap with one another during ventricular contraction is undesirable. Some undesirable results include the occurrence of thrombosis, the prevention of adequate coaptation between the mitral leaflets, and the abrasion of sections 922, 932 which could eventually lead to disruption of apparatus 900 over time. Diamond-shaped cells 902 can conform to and transition between the cylindrical-shaped opened mitral valve 30 and the hourglass-shaped closed mitral valve 30 without cells 902 overlapping with one another during ventricular contraction. As discussed herein, when apparatus 900 is implanted in heart 10, the diamond-shaped cells 902 near or at the tapered waist bottom of the hourglass-shaped closed mitral valve 30 are elongated longitudinally and contracted laterally in response to the closing of mitral valve 30. The elongation and narrowing of the diamond-shaped cells 902 near or at the tapered waist bottom of the hourglass-shaped closed mitral valve 30 avoids the overlapping of cells 902.

It is understood that cells 902 may have other suitable shapes that could provide the elongation and narrowing of cells similar to the diamond shaped cells discussed herein. Other suitable shapes, e.g., other types of polygons such as triangles, quadrilaterals other than diamonds, pentagons, hexagons, etc. For example, in the FIG. 4A-H embodiment, cells 102 of sections 122, 132 have a square shape.

Apparatus 900 is delivered and positioned within the heart using the same methods as described in respect of apparatus 100 elsewhere here.

Interpretation of Terms

Unless the context clearly requires otherwise, throughout the description and the claims:

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof; elements which are integrally formed may be considered to be connected or coupled;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An apparatus for repairing a heart valve, the apparatus comprising:
a radially compressible and expandable body, the body having an anterior end and a posterior end;
an anterior member connected to a posterior member, the anterior and posterior members being attached to the anterior and posterior ends of the body respectively, wherein the anterior and posterior members each comprise a section extending radially around the body, and extending longitudinally from the body to a plurality of positioning cords, wherein each section comprises a net-like structure defined by a plurality of cells, and wherein the plurality of positioning cords are spaced laterally across the respective section, arranged to extend longitudinally away from the body, from the section to a respective end thereof;
an anterior tube and a posterior tube each being attached to the respective plurality of positioning cords at the respective end thereof; and
first and second adjustment cords extending through each of the anterior and posterior tubes, wherein the anterior and posterior tubes are lengthened or shortened by tensioning the respective adjustment cord, wherein the length of each positioning cord is selected to suspend the respective anterior and posterior tube from the respective anterior and posterior member in a parabolic or parabolic-like shape.

2. An apparatus according to claim 1, wherein tensioning the first and second adjustment cords lengthens or shortens the respective anterior and posterior tubes consequently displacing the respective tube towards or away from the body causing corresponding displacement of the respective anterior and posterior members.

3. An apparatus according to claim 1, wherein lengthening the anterior and posterior tube consequently displaces a vertex of the parabolic or parabolic-like shaped respective anterior and posterior tube towards the body, and wherein shortening the anterior and posterior tube consequently displaces the vertex of the parabolic or parabolic-like shaped tube away from the body.

4. An apparatus according to claim 1, wherein the body comprises a plurality of peaks and a plurality of troughs, the peaks and troughs defined interchangeably along a diameter of the body.

5. An apparatus according to claim 4, wherein the body comprises a plurality of ring members, each ring member positioned on a corresponding peak.

6. An apparatus according to claim 5, further comprising an encircling member connectable to the body for radially compressing and/or radially expanding the body, and wherein the encircling member passes through the plurality of ring members.

7. An apparatus according to claim 1, wherein the body defines at least one anchoring site.

8. An apparatus according to claim 1, wherein the body comprises a skirt, and wherein the skirt defines at least one anchoring site.

9. An apparatus according to claim 1, wherein the apparatus is configured to extend from an atrial wall and a mitral annulus to an anterior-lateral papillary muscle and a posterior-medial papillary muscle of the heart valve when the apparatus is implanted in the heart valve.

10. An apparatus according to claim 1, wherein the anterior member is configured to cover an anterior mitral leaflet of the heart valve when the apparatus is implanted in the heart valve.

11. An apparatus according to claim 1, wherein the posterior member is configured to cover a posterior mitral leaflet of the heart valve when the apparatus is implanted in the heart valve.

12. An apparatus according to claim 1, wherein the anterior and posterior members are each formed of a material comprising a biocompatible, blood-permeable material that permits the passage of blood therethrough.

13. An apparatus according to claim 1, wherein the plurality of cells has a diamond shape, a square shape, or a rectangular shape.

14. An apparatus according to claim 13, wherein the diamond-shaped cells are contractable between a relaxed position and an elongated position.

15. An apparatus according to claim 14, wherein the diamond-shaped cells are uniform in shape and size in the relaxed position, and wherein the diamond-shaped cells are heterogeneous in shape and size in the elongated position.

16. An apparatus according to claim 15, wherein the diamond-shaped cells each comprises a first diagonal length extending between longitudinally opposing vertices, and a second diagonal length extending between laterally opposing vertices, the diamond-shaped cells positioned near the body have greater second diagonal lengths than the diamond-shaped cells positioned near the positioning cords.

17. An apparatus according to claim 16, wherein the diamond-shaped cells positioned near the positioning cords have greater first diagonal lengths than the diamond-shaped cells positioned near the body.

* * * * *